US012747450B2

(12) United States Patent
Kessel et al.

(10) Patent No.: US 12,747,450 B2
(45) Date of Patent: Sep. 29, 2026

(54) GENE CONFERRING RESISTANCE TO FUNGAL PATHOGEN

(71) Applicants: KWS SAAT SE & Co. KGaA, Einbeck (DE); University of Zurich, Zurich (CH)

(72) Inventors: Bettina Kessel, Einbeck (DE); Milena Ouzunova, Göttingen (DE); Thomas Presterl, Einbeck (DE); Daniela Scheuermann, Einbeck (DE); Gerhard Herren, Gossau (CH); Beat Keller, Zurich (CH); Simon Krattinger, Bonstetten (CH); Thomas Wicker, Hüttwilen (CH); Ping Yang, Zurich (CH)

(73) Assignees: KWS SAAT SE & Co. KGaA, Einbeck (DE); University of Zurich, Zurich (CH)

( * ) Notice: Subject to any disclaimer, the term of this patent is extended or adjusted under 35 U.S.C. 154(b) by 538 days.

(21) Appl. No.: 16/640,973

(22) PCT Filed: Aug. 22, 2018

(86) PCT No.: PCT/EP2018/072665
§ 371 (c)(1),
(2) Date: Feb. 21, 2020

(87) PCT Pub. No.: WO2019/038326
PCT Pub. Date: Feb. 28, 2019

(65) Prior Publication Data

US 2021/0071194 A1 Mar. 11, 2021

(30) Foreign Application Priority Data

Aug. 22, 2017 (EP) .................................... 17187309
Dec. 8, 2017 (EP) .................................... 17206305

(51) Int. Cl.

| | |
|---|---|
| ***C12N 15/82*** | (2006.01) |
| ***A01H 1/06*** | (2006.01) |
| ***A01H 3/04*** | (2006.01) |
| ***C07K 14/415*** | (2006.01) |
| ***C12Q 1/48*** | (2006.01) |
| ***C12Q 1/6827*** | (2018.01) |
| ***C12Q 1/6869*** | (2018.01) |

(52) U.S. Cl.
CPC ........... *C12N 15/8282* (2013.01); *A01H 1/06* (2013.01); *A01H 3/04* (2013.01); *C07K 14/415* (2013.01); *C12N 15/8216* (2013.01); *C12N 15/8243* (2013.01); *C12Q 1/485* (2013.01); *C12Q 1/6827* (2013.01); *C12Q 1/6869* (2013.01); *C12Y 207/99* (2013.01); *C12Q 2525/204* (2013.01)

(58) Field of Classification Search
None
See application file for complete search history.

(56) References Cited

U.S. PATENT DOCUMENTS

| | | | |
|---|---|---|---|
| 2016/0201080 A1 | 7/2016 | Ouzunova et al. | |
| 2021/0137040 A1 * | 5/2021 | Ouzunova ............ | C07K 14/415 |

FOREIGN PATENT DOCUMENTS

| | | | | |
|---|---|---|---|---|
| CN | 109844121 A | 6/2019 | | |
| WO | 98/40505 A1 | 9/1998 | | |
| WO | 00/29592 | 5/2000 | | |
| WO | 2007/147395 | 12/2007 | | |
| WO | 2010/079430 A1 | 7/2010 | | |
| WO | 2011/072246 | 6/2011 | | |
| WO | WO-2011163590 A1 * | 12/2011 | ............... | A01H 1/04 |
| WO | 2015/032494 | 3/2015 | | |
| WO | 2017066597 A1 | 4/2017 | | |

OTHER PUBLICATIONS

Mazie Genetics and Genomics Database. Chromosome 8, Region 6 (Bin 8.06) (Year: 2022).*
Welz et al. Plant Breeding, 119: 1-14. (Year: 2000).*
International Search Report and Written Opinion mailed on Sep. 24, 2018, issued in corresponding Application No. PCT/EP2018/072688.
Lipps et al., "Interaction of Ht and partial resistance to Exserohilum turcicum in maize", Plant Disease, 1997, vol. 81, pp. 277-282,.
Welz et al., "Genes for resistance to northern corn leaf blight in diverse maize populations", Plant Breeding, 2000, vol. 119, pp. 1-14.
Jordan et al., "Occurrence of Race 2 of Exserohilum turcicum on Corn in the Central and Eastern United States", Plant Disease, 1983, vol. 67, No. 10, pp. 1163-1165.
Thakur et al., "Effects of temperature and light on virulence of Exserohilum turcicum on corn", Phytopathology, 1989, vol. 79, No. 6, pp. 631-635.
Simcox et al., "The use of molecular markers to study Setosphaeria turcica resistance in maize", Phytopathology, 1993, vol. 83, No. 12, pp. 1326-1330.

(Continued)

*Primary Examiner* — David R Byrnes
(74) *Attorney, Agent, or Firm* — Troutman Pepper Locke LLP

(57) ABSTRACT

The present invention relates to a nucleic acid molecule encoding a polypeptide conferring resistance to a plant against a fungal pathogen, such as *Helminthosporium turcicum*. The present invention further relates to a plant (or part thereof) comprising the nucleic acid molecule, and methods involving the nucleic acid molecule.

8 Claims, 12 Drawing Sheets

Specification includes a Sequence Listing.

(56) References Cited

OTHER PUBLICATIONS

Chung et al., "Characterization and fine-mapping of a resistance locus for northern leaf blight in maize bin 8.06", Theoretical and Applied Genetics, 2010, vol. 121, No. 2, pp. 205-227.
Perkins et al., "Disease development and yield losses associated with northern leaf blight on corn", Plant Disease, vol. 71, No. 10, 1987, pp. 940-943.
Wang et al., "Expression of Ht2-related genes in response to the HT-Toxin of Exserohilum turcicum in Maize", Annals of Applied Biology, 2010, vol. 156, pp. 111-120.
Jones et al., "The plant immune system", Nature, vol. 444, Article 7117, 2006, pp. 323-329.
Macho et al., "Plant PRRs and the activation of innate immune signaling", Molecular Cell, 2014, vol. 54, No. 2 ,pp. 263-272.
Hu et al., "Improvement of multiple agronomic traits by a disease resistance gene via cell wall reinforcement", Nature Plants, 2017, vol. 3, Article 17009, 35 pages.
Dardick et al., "Non-arginine aspartate (non-RD) kinases are associated with innate immune receptors that recognize conserved microbial signatures", Current Opinion in Plant Biology, 2012, vol. 15, No. 4, pp. 358-366.
Shl et al., "Marker development, saturation mapping, and high-resolution mapping of the Septoria nodorum blotch susceptibility gene Snn3-B1 in wheat", Molecular Genetics and Genomics, 2016, vol. 291, No. 1, pp. 107-119.
Kohorn et al., "Pectin activation of MAP kinase and gene expression is WAK2 dependent", The Plant Journal, vol. 60, No. 6, 2009, pp. 974-982.
Kanneganti et al., "Wall associated kinases from plants-an overview", Physiology and Molecular Biology of Plants vol. 14, No. 1&2, 2008, pp. 109-118.
Li et al., "A novel wall-associated receptor-like protein kinase gene, OsWAK1, plays important roles in rice blast disease resistance", Plant Molecular Biology, vol. 69, No. 3, 2009, pp. 337-346.
Zuo et al. "A maize wall-associated kinase confers quantitative resistance to head smut", Nature Genetics, vol. 47, No. 2, 2015, pp. 151-157.
Shi et al. "The hijacking of a receptor kinase-driven pathway by a wheat fungal pathogen leads to disease," Science Advances, vol. 2, No. 10, 2016, e1600822, 9 pages.
Hufnagel et al., "Duplicate and conquer: Multiple homologs of Phosphorus-Starvation Tolerance1 enhance phosphorus acquisition and sorghum performance on low-phosphorus soils", Plant Physiology, 2014, vol. 166, No. 2, pp. 659-677.
Kaur et al., "A root-specific wall-associated kinase gene, HvWAK1, regulates root growth and is highly divergent in barley and other cereals", Functional & Integrative Genomics, vol. 13, No. 2, 2013, pp. 167-177.
Wang et al., "The rice wall-associated receptor-like kinase gene OsDEES1 plays a role in female gametophyte development", Plant Physiology, vol. 160, No. 2, 2012, pp. 696-707.
Niemeyer, "Hydroxamic acids derived from 2-hydroxy-2H-1, 4-benzoxazin-3 (4 H)-one: key defense chemicals of cereals", Journal of Agricultural and Food Chemistry, vol. 57, No. 5, 2009, pp. 1677-1696.
Frey et al., "A 2-oxoglutarate-dependent dioxygenase is integrated in DIMBOA-biosynthesis", Phytochemistry, vol. 62, No. 3, 2003, pp. 371-378.
Long et al., "Relationship of hydroxamate concentration in maize and field reaction to Helminthosporium turcicum", Crop Science, vol. 18, No. 4, 1978, pp. 573-575.
Kammerloher et al., "Water channels in the plant plasma membrane cloned by immunoselection from a mammalian expression system", The Plant Journal, vol. 6, No. 2, 1994, pp. 187-199.
Oikawa et al., "Induction of HDMBOA-Glc accumulation and DIMBOA-Gic 4-O-methyltransferase by jasmonic acid in poaceous plants", Phytochemistry, vol. 61, No. 3, 2002, pp. 331-337.
Oikawa et al., "Accumulation of HDMBOA-Glc is induced by biotic stresses prior to the release of MBOA in maize leaves", Phytochemistry, vol. 65, No. 22, 2004, pp. 2995-3001.
Brutus et al., "A domain swap approach reveals a role of the plant wall-associated kinase 1 (WAK1) as a receptor of oligogalacturonides", Proceedings of the National Academy of Sciences, vol. 107, No. 20, 2010, pp. 9452-9457.
Kim et al., "Increasing the genome-targeting scope and precision of base editing with engineered Cas9-cytidine deaminase fusions", Nat. Blotechnol., 2017, vol. 35, No. 4, pp. 371-376.
Gao et al., "Engineered Cpf1 Enzymes with Altered PAM Specificities", BioRxiv, 2016, http://dx.doi.org/10.1101/091611.
Handrick et al., "Biosynthesis of 8-O-methylated benzoxazinold defense compounds in maize", The Plant Cell, vol. 28, No. 7, 2016, pp. 1682-1700.
Fire et al., "Potent and specific genetic interference by double-stranded RNA in Caenorhabditis elegans", Nature, 1998, vol. 391 (6669), pp. 806-811.
Chung et al., "Resistance loci affecting distinct stages of fungal pathogenesis: use of introgression lines for QTL mapping and characterization in the maize—Setosphaeria turcica pathosystem", BMC Plant Biology, vol. 10, No. 1, 2010, Artcile 103, 25 pages.
Du et al., "agriGO: a GO analysis toolkit for the agricultural community", Nucleic Acids Research, 2010, vol. 38, Web Server Issue, W64-W70.
Melhis et al. "Natural variation in maize aphid resistance is associated with 2,4-dihydroxy-7-methoxy-1,4-benzoxazin-3-one glucoside methyltransferase activity", The Plant Cell, vol. 25, No. 6, 2013, pp. 2341-2355.
Ahmad et al., "Benzoxazinoid Metabolites Regulate Innate Immunity against Aphids and Fungi in Maize", Plant Physiology, vol. 157, No. 1, 2011, pp. 317-327.
Hurni et al., "The maize disease resistance gene Htn1 against northern corn leaf blight encodes a wall-associated receptor-like kinase", Proceedings of the National Academy of Sciences of the United States of America, 2015, vol. 112, No. 28, pp. 8780-8785.
Wagner et al., "Wall-Associated Kinases Are Expressed throughout Plant Development and Are Required for Cell Expansion", The Plant Cell, 2001, vol. 13, pp. 303-318.
Arteaga et al., "Genomic variation in recently collected maize landraces from Mexico", Genomics Data, 2016, vol. 7, pp. 38-45.
International Search Report and Written Opinion mailed on Sep. 27, 2018, issued in corresponding Application No. PCT/EP2018/072665.
Yang et al., "Fungal resistance mediated by maize wall-associated kinase ZmWAK-RLK1 correlates with reduced benzoxazinoid content", New Phytologist, 2019, vol. 221, Issue 2, pp. 976-987.
Yang et al., "Alleles of a wall-associated kinase gene account for three of the major northern corn leaf blight resistance loci in maize", The Plant Journal, 2021, vol. 106, Issue 2, pp. 526-535.
Liu et al., "Research development on benzoxazinoids", Plant Protection, 2003, vol. 29, No. 4, pp. 3-7. (with English Abstract and listed on p. 7 of the translation of Office Action Issued in CN Application No. 201880068564 dated Feb. 24, 2023.).
Office Action Issued in CN Application No. 201880068564 dated Feb. 24, 2023.
Moghaddam et al., "Reactions of Isolates from Matings of Races 1 and 23N of Exserohilum turcicum", Plant Disease, 1994, vol. 78, No. 8, pp. 767-771.
Zhang, "Proteomics Identification of Differentially Expressed Leaf Proteins in Response to Setosphaeria turcica Infection in Resistant Maize", Journal of Integrative Agriculture, 2014, vol. 13, No. 4, pp. 789-803.

* cited by examiner

FIG 2 A

```
SEQ_ID_NO:_2        atggctgctcacctaccacgcctccccgtcctcctcctcgtcctcctcgctgcccatgtc
SEQ_ID_NO:_9        atggctgctcaccagcctcacctctccgtcctcctcctcgtcctcctcgctgcccatgtc
SEQ_ID_NO:_11       atggctgctcaccagcctcacctctccgtcctcctcctcgtcctcctcgctgcccatgtc
SEQ_ID_NO:_13       atggctgctcacctaccacgcctccccgtcctcctcctcgtcctcctcgctgctcatgtc
                    *************  ** * **** **************************** ******

SEQ_ID_NO:_2        gtctccacctccgcccatgccgagcctcctcttccgagcccttacagcacctccgcccat
SEQ_ID_NO:_9        gtctccacctccgcccatggcgagcctcctcttccgagcccttacaacacctccgcccat
SEQ_ID_NO:_11       gtctccacctccgcccatggcgagcctcctcttccgagcccttacaacacctccgcccat
SEQ_ID_NO:_13       gtctccacctccgcccatgccgagcctcctcttccgagcccttacagcacctccgcccat
                    ******************* ************************** *************

SEQ_ID_NO:_2        ggcgagcctcctcttccgagcacttacaacgtctccatgtgctcggaatcgttctggtgc
SEQ_ID_NO:_9        ggcgagcctcctcttccgagcacttacaacgcctccatgtgctcgt---cgttctggtgt
SEQ_ID_NO:_11       ggcgagcctcctcttccgagcacttacaacgcctccatgtgctcgt---cgttctggtgt
SEQ_ID_NO:_13       ggcgagcctcctcttccgagcacttacaacgtctccatgtgctcggaatcgttctggtgc
                    ******************************* *************    ********** 

SEQ_ID_NO:_2        ggcggcgtcgaaatccgctacccgttctatcttgccaacgcaaccgccgactacagcggg
SEQ_ID_NO:_9        ggcggcgtcgagatccgctacccgttctatcttgccaacgcaatcgccgactacagcggg
SEQ_ID_NO:_11       ggcggcgtcgagatccgctacccgttctatcttgccaacgcaatcgccgactacagcggg
SEQ_ID_NO:_13       ggcggcgtcgaaatccgctacccgttctatcttgccaacgcaaccgccgactacagcggg
                    *********** ******************************* ****************

SEQ_ID_NO:_2        agctactactcctgcggctacaccgacttgagcgtttcctgcaaactcgaggtcgagggg
SEQ_ID_NO:_9        agctactactcctgcggctacaccgacttgagcgtttcctgcgaactcgaggtcgagggg
SEQ_ID_NO:_11       agctactactcctgcggctacaccgacttgagcgtttcctgcgaactcgaggtcgagggg
SEQ_ID_NO:_13       agctactactcctgcggctacaccgacttgagcgtttcctgcaaactcgaggtcgagggg
                    ****************************************** *****************

SEQ_ID_NO:_2        ccgacgacgacatggacccctaccatccgtctcggcggcgacaactacaccgtcaagaac
SEQ_ID_NO:_9        tcgccgacgacctggacccctaccatccgtctcggcggcggcgactacaccgtcaagaac
SEQ_ID_NO:_11       tcgccgacgacctggacccctaccatccgtctcggcggcggcgactacaccgtcaagaac
SEQ_ID_NO:_13       ccgacgacgacatggacccctaccatccgtctcggcggcgacaactacaccgtcaagaac
                     ** ******* **************************** * *****************

SEQ_ID_NO:_2        atcttgta------cgactatcataccatctcactggcggacagcgatgtgctcggaggc
SEQ_ID_NO:_9        atctcctacctctacgaccagcagaccatctcactggcggacagagatgtgctcggaggc
SEQ_ID_NO:_11       atctcctacctctacgaccagcagaccatctcactggcggacagagatgtgctcggaggc
SEQ_ID_NO:_13       atcttgta------cgactatcataccatctcactggcggacagcgatgtgctcggaggc
                    ****  **      **** * ** ******************** ***************

SEQ_ID_NO:_2        ggcgagtgccccgtcgtccaccacaacgtcagcttcgacgagacgtggctgca------c
SEQ_ID_NO:_9        ggcggctgccccgtcgtccgccacaacgtcagcttcgacgagacgtggctgcacctgcac
SEQ_ID_NO:_11       ggcggctgccccgtcgtccgccacaacgtcagcttcgacgagacgtggctgcacctgcac
SEQ_ID_NO:_13       ggcgagtgccccgtcgtccaccacaacgtcagcttcgacgagacgtggctgca------c
                    ****  ************* *********************************      *

SEQ_ID_NO:_2        aaccccagcgccttcgacaacctcaccttcttcttcggatgccactgggggccacgcgat
SEQ_ID_NO:_9        aacgccagcgccttcgacaacctcaccttcttcttcggatgccactgggggccacggaat
SEQ_ID_NO:_11       aacgccagcgccttcgacaacctcaccttcttcttcggatgccactgggggccacggaat
SEQ_ID_NO:_13       aaccccagcgccttcgacaacctcaccttcttcttcggatgccactgggggccacgcgat
                    *** ****************************************************  **

SEQ_ID_NO:_2        acactgcctgaatttgccggcaacaacatcagctgcgccgggttcagtactccagctatc
SEQ_ID_NO:_9        acaccgcctgaatttgccgactacaacatcagctgcgccgggttcaatactccaactatc
SEQ_ID_NO:_11       acaccgcctgaatttgccgactacaacatcagctgcgccgggttcaatactccaactatc
SEQ_ID_NO:_13       acactgcctgaatttgccggcaacaacatcagctgcgccgggttcagtactccagctatc
                    **** ************** * ************************ ******* *****
```

FIG 2 B

```
SEQ_ID_NO:_2        agcggtggaggctccttcgtgttcaagcctgaagatcttgacgaacatgcggagcaggag
SEQ_ID_NO:_9        agcggtggaaggtccttcgtgttcaagactggagatcttgacgaacaagaggagcaggag
SEQ_ID_NO:_11       agcggtggaaggtccttcgtgttcaagactggagatcttgacgaacaagaggagcaggag
SEQ_ID_NO:_13       agcggtggaggctccttcgtgttcaagcctgaagatcttgacgaacatgcggagcaggag
                    ********* * *************** *** *************** * **********

SEQ_ID_NO:_2        ttggcttcacactgcgacgaggttttctccgtgccagtgagaagcgaggctctgcagcag
SEQ_ID_NO:_9        ttggctttacactgcgacgaggttttctccgtgccagtgagaagagatgctctgcaggcg
SEQ_ID_NO:_11       ttggctttacactgcgacgaggttttctccgtgccagtgagaagagatgctctgcaggcg
SEQ_ID_NO:_13       ttggcttcacactgcgacgaggttttctccgtgccagtgagaagcgaggctctgcagcag
                    ******* ************************************ ** *********  *

SEQ_ID_NO:_2        gcgatcgtcagcaacctcagcctcggggacgggtacggcgagctgcttaggcaggggatc
SEQ_ID_NO:_9        atcgtcagcaacttcagcctcacacgggacgggtacggcgaggtgcttaggcaggggttc
SEQ_ID_NO:_11       atcgtcagcaacttcagcctcacacgggacgggtacggcgaggtgcttaggcaggggttc
SEQ_ID_NO:_13       gcgatcgtcagcaacctcagcctcggggacgggtacggcgagctgcttaggcaggggatc
                        **  ** *  *  *  *    ***************** ************** **

SEQ_ID_NO:_2        gagttggaatggaaacggacatcggaggatcagtgtggccagtgcgaggaatcgggctcc
SEQ_ID_NO:_9        gagttggaatggaatcggacatcggaggatcagtgtggccggtgcgagggatcgggctcc
SEQ_ID_NO:_11       gagttggaatggaatcggacatcggaggatcagtgtggccggtgcgagggatcgggctcc
SEQ_ID_NO:_13       gagttggaatggaaacggacatcggaggatcagtgtggccagtgcgaggaatcgggctcc
                    ************* ************************** ******** **********

SEQ_ID_NO:_2        ggcggacggtgcgcctacagccagaagagagaattccttggctgcttctgcagcggaggg
SEQ_ID_NO:_9        ggcggatggtgcgcctacagccagaagagagaattcctgggctgcttgtgcagcggaggg
SEQ_ID_NO:_11       ggcggatggtgcgcctacagccagaagagagaattcctgggctgcttgtgcagcggaggg
SEQ_ID_NO:_13       ggcggacggtgcgcctacagccagaagagagaattccttggctgcttgtgcagcggaggg
                    ****** ******************************* ******** ************

SEQ_ID_NO:_2        aaggcgggcaacccgttctgcaaaccatcaagatcaacaaaaaggagagaagcagcatct
SEQ_ID_NO:_9        aaggtgggcagcccgttctgcaaaccatcgagatcaaaaa------ggaaagaaggacct
SEQ_ID_NO:_11       aaggtgggcagcccgttctgcaaaccatcgagatcaaaaa------ggaaagaaggacct
SEQ_ID_NO:_13       aaggcgggcaacccgttctgcaaaccatcaagatcaaaaa------ggaaagaagcatct
                    **** ***** ****************** ******* **      *  *** ** * **

SEQ_ID_NO:_2        attgttggtgctgttgccgttgcattcctgtgtctagtcattctcacatgcttcttggct
SEQ_ID_NO:_9        attgttggtgctgttgccgttgcattcctgtgtctagtcattctcacatgcttcttggct
SEQ_ID_NO:_11       attgttggtgctgttgccgttgcattcctgtgtctagtcattctcacatgcttcttggct
SEQ_ID_NO:_13       attgttggtgctgttgccgttgcattcctgtgtctagtcattctcacatgcttcttggct
                    ************************************************************

SEQ_ID_NO:_2        tgtagacattgttcgctgcccttcaaatcgaagaacaaaccagggacaaggattgagtcc
SEQ_ID_NO:_9        tgtagacatggttcgctgcccttcaaatcggagaacaaaccagggacaaggattgagtcc
SEQ_ID_NO:_11       tgtagacatggttcgctgcccttcaaatcggagaacaaaccagggacaaggattgagtcc
SEQ_ID_NO:_13       tgtagacatggttcgctgcccttcaaatcggagaacaaaccagggacaaggattgagtcc
                    ********* ******************** *****************************

SEQ_ID_NO:_2        ttcctacagaagaacgagagtagtatacatccgaaaagatacacctacgcggacgtgaaa
SEQ_ID_NO:_9        ttcctacagaagaacgaga---gtatacatccgaaaagatacacctacgcggacgtgaaa
SEQ_ID_NO:_11       ttcctacagaagaacgaga---gtatacatccgaaaagatacacctacgcggacgtgaaa
SEQ_ID_NO:_13       ttcctacagaagaacgaga---gtatacatccgaaaagatacacctacacggacgtgaaa
                    *******************   ************************** ***********

SEQ_ID_NO:_2        agaatgacaaaatccttcgctgtgaagctaggccaaggtgggtttggtgctgtatacaaa
SEQ_ID_NO:_9        agaatgacaaaatccttcgctgtgaagctaggccaaggtgggtttggtgctgtatacaaa
SEQ_ID_NO:_11       agaatgacaaaatccttcgctgtgaagctaggccaaggtgggtttggtgctgtatacaaa
SEQ_ID_NO:_13       agaatgacaaaatccttcgctgtgaagctaggccaaggtgggtttggtgctgtatacaaa
                    ************************************************************
```

FIG 2 C

```
SEQ_ID_NO:_2        ggcagcctccacgatggccgacaggtagcagtcaagatgctgaaggacacccaaggtgac
SEQ_ID_NO:_9        ggcagcctccacgatggccgacaggtagcagtcaagatgctgaaggacacccaaggtgac
SEQ_ID_NO:_11       ggcagcctccacgatggccgacaggtagcagtcaagatgctgaaggacacccaaggtgac
SEQ_ID_NO:_13       ggcagcctccacgatggccgacaggtagcagtcaagatgctcaaggacacccaaggtgac
                    ***************************************** ******************

SEQ_ID_NO:_2        ggcgaggaattcatgaacgaggtggctagcatcagcaggacttctcatgtcaacgtcgtg
SEQ_ID_NO:_9        ggcgaggaattcatgaacgaggtggctagcatcagcaggacttctcatgtcaacgtcgtg
SEQ_ID_NO:_11       ggcgaggaattcatgaacgaggtggctagcatcagcaggacttctcatgtcaacgtcgtg
SEQ_ID_NO:_13       ggcgaggaattcatgaacgaggtggctagcatcagcaggacttctcatgtcaacgtcgtg
                    ************************************************************

SEQ_ID_NO:_2        acacttctagggttttgcttgcaagggtcgaaaagagcactgatctacgagtacatgccc
SEQ_ID_NO:_9        acacttctagggttttgcttgcaagggtcgaaaagagcactgatctacgagtacatgccc
SEQ_ID_NO:_11       acacttctagggttttgcttgcaagggtcgaaaagagcactgatctacgagtacatgccc
SEQ_ID_NO:_13       acacttctagggttttgcttgcaagggtcgaaaagagcactgatctacgagtacatgccc
                    ************************************************************

SEQ_ID_NO:_2        aatggttcgctcgaaaggtatgccttcaccggtgacatgaacagtgagaatttgctaacc
SEQ_ID_NO:_9        aatggttcgctcgaaaggtatgccttcaccggtgacatgaacagtgagaatttgctaacc
SEQ_ID_NO:_11       aatggttcgctcgaaaggtatgccttcaccggtgacatgaacagtgagaatttgctaacc
SEQ_ID_NO:_13       aatggttcgctcgaaaggtatgccttcaccggtgacatgaacagtgagaatttgctaacc
                    ************************************************************

SEQ_ID_NO:_2        tgggaaagactatttgacatagcgattggcacggccagagggctcgaatacctacaccgg
SEQ_ID_NO:_9        tgggaaaggctatttgacatagcaattggcacggccagagggctcgaatacctacaccgg
SEQ_ID_NO:_11       tgggaaaggctatttgacatagcaattggcacggccagagggctcgaatacctacaccgg
SEQ_ID_NO:_13       tgggaaaggctatttgacatagcaattggcacggccagagggctcgaatacctacaccgg
                    ******** ************** ************************************

SEQ_ID_NO:_2        ggatgcaacactcggatcgtgcattttgacatcaagccacacaacatcctgttagaccag
SEQ_ID_NO:_9        ggatgcaacactcggatcgtgcattttgacatcaagccacacaacatcctgttagaccag
SEQ_ID_NO:_11       ggatgcaacactcggatcgtgcattttgacatcaagccacacaacatcctgttagaccag
SEQ_ID_NO:_13       ggatgcaacactcggatcgtgcattttgacatcaagccacacaacatcctgttagaccag
                    ************************************************************

SEQ_ID_NO:_2        gatttctgccctaagatctctgactttggactggccaagctatgtctgaacaaagagagc
SEQ_ID_NO:_9        gatttctgtcctaagatctctgactttggactggccaagctatgtctgaacaaagagagc
SEQ_ID_NO:_11       gatttctgtcctaagatctctgactttggactggccaagctatgtctgaacaaagagagc
SEQ_ID_NO:_13       gatttctgtcctaagatctctgactttggactggccaagctatgtctgaacaaagagagc
                    ******** ***************************************************

SEQ_ID_NO:_2        gctatctccattgctggcgcaagagggacgatagggtatatcgccccggaggtctactca
SEQ_ID_NO:_9        gctatctccattgctggcgcaagagggacgatagggtatatcgccccggaggtctactca
SEQ_ID_NO:_11       gctatctccattgctggcgcaagagggacgatagggtatatcgccccggaggtctactca
SEQ_ID_NO:_13       gctatctccattgttggcgcaagagggacgatagggtatatcgccccggaggtctactca
                    ************ ***********************************************

SEQ_ID_NO:_2        aagcaatttggaacgatcagcagcaagtctgatgtctatagctatgggatgatggtcctt
SEQ_ID_NO:_9        aagcaatttggaataataagcagcaagtctgatgtctatagctatgggatgatggtcctt
SEQ_ID_NO:_11       aagcaatttggaataataagcagcaagtctgatgtctatagctatgggatgatggtcctt
SEQ_ID_NO:_13       aagcaatttggaacaatcagcagcaagtctgatgtctatagctatgggatgatggtcctt
                    *************  ** ******************************************

SEQ_ID_NO:_2        gagatggttggagcaagggacaggaataca------agcgcagatagtgaccatagcagc
SEQ_ID_NO:_9        gagatggttggagcaagggacaggaataca------agcgcagatagtgaccatagcagc
SEQ_ID_NO:_11       gagatggttggagcaagggacaggaataca------agcgcagatagtgaccatagcagc
SEQ_ID_NO:_13       gagatggttggagcaagggaaaggaatacaagcgcaagcgcagatagtgaccatagcagc
                    ******************** *********      ************************
```

FIG 2 D

```
SEQ_ID_NO:_2        caatatttccctcagtggctttatgaacatttggacgactattgtgttggtgcttccgag
SEQ_ID_NO:_9        caatatttccctcagtggctttatgaacatttggacgactattgtgttggtgcttccgag
SEQ_ID_NO:_11       caatatttccctcagtggctttatgaacatttggacgactattgtgttggtgcttccgag
SEQ_ID_NO:_13       caatatttccctcagtggatttatgaacatttggacgactattgtgttggtgcttccgag
                    ****************** *****************************************

SEQ_ID_NO:_2        attaatggtgagaccacagagctcgtgaggaagatgatagttgtaggtctgtggtgcata
SEQ_ID_NO:_9        attaatggtgagaccacagagctcgtgaggaagatgatagttgtaggtctgtggtgcata
SEQ_ID_NO:_11       attaatggtgagaccacagagctcgtgaggaagatgatagttgtaggtctgtggtgcata
SEQ_ID_NO:_13       attaatggtgagaccacagagctcgtgaggaagatgatagttgtaggtctgtggtgcata
                    ************************************************************

SEQ_ID_NO:_2        caagtgattccgactgatcgaccaacaatgacgagagtcgtcgagatgttggaaggaagc
SEQ_ID_NO:_9        caagtgattccgactgatcgaccaacaatgacgagagtcgtcgagatgttggaagggagc
SEQ_ID_NO:_11       caagtgattccgactgatcgaccaacaatgacgagagtcgtcgagatgttggaagggagc
SEQ_ID_NO:_13       caagtgattccgactgatcgaccaacaatgacgagagtcgtcgagatgttggaagggagc
                    ******************************************************** ***

SEQ_ID_NO:_2        acaagtaatctagagttgccacccagagttctcttgagctga
SEQ_ID_NO:_9        acaagtaatctagagttgccacccagagttctcttgagctga
SEQ_ID_NO:_11       acaagtaatctagagttgccacccagagttctcttgagctga
SEQ_ID_NO:_13       acgagtaatctagagttgccacccagagttctcttgagctga
                    ** ***************************************
```

FIG 3 A

```
Majority             MAAHLPRLPVLLLVLLAAHVVSTSAHAEPPLPSPYSTSAHGEPPLPSTYNVSMCSESFWCGGVEIRYPFYLANATADYSG
                     ---------+---------+---------+---------+---------+---------+---------+---------+
                              10        20        30        40        50        60        70        80
                     ---------+---------+---------+---------+---------+---------+---------+---------+
RLK1_A619HT2_CDS     MAAHLPRLPVLLLVLLAAHVVSTSAHAEPPLPSPYSTSAHGEPPLPSTYNVSMCSESFWCGGVEIRYPFYLANATADYSG
RLK1_A619HT3_CDS     MAAHLPRLPVLLLVLLAAHVVSTSAHAEPPLPSPYSTSAHGEPPLPSTYNVSMCSESFWCGGVEIRYPFYLANATADYSG
RLK1_B37HTN_CDS      MAAHQPHLSVLLLVLLAAHVVSTSAHGEPPLPSPYNTSAHGEPPLPSTYNASMCS-SFWCGGVEIRYPFYLANAIADYSG
RLK1_A619HT2_Exon1   MAAHLPRLPVLLLVLLAAHVVSTSAHAEPPLPSPYSTSAHGEPPLPSTYNVSMCSESFWCGGVEIRYPFYLANATADYSG
RLK1_A619Ht2_Exon2
RLK1_A619Ht2_Exon3

Majority             SYYSCGYTDLSVSCKLEVEGPTTTWTPTIRLGGDNYTVKNI---YDYHTISLADSDVLGGGECPVVHHNVSFDETWLH--
                     ---------+---------+---------+---------+---------+---------+---------+---------+
                              90       100       110       120       130       140       150       160
                     ---------+---------+---------+---------+---------+---------+---------+---------+
RLK1_A619HT2_CDS     SYYSCGYTDLSVSCKLEVEGPTTTWTPTIRLGGDNYTVKNI---YDYHTISLADSDVLGGGECPVVHHNVSFDETWLH--
RLK1_A619HT3_CDS     SYYSCGYTDLSVSCKLEVEGPTTTWTPTIRLGGDNYTVKNI---YDYHTISLADSDVLGGGECPVVHHNVSFDETWLH--
RLK1_B37HTN_CDS      SYYSCGYTDLSVSCELEVEGSPTTWTPTIRLGGGDYTVKNISYLYDQQTISLADRDVLGGGGCPVVRHNVSFDETWLHLH
RLK1_A619HT2_Exon1   SYYSCGYTDLSVSCKLEVEGPTTTWTPTIRLGGDNYTVKNI---YDYHTISLADSDVLGGGECPVVHHNVSFDETWLH--
RLK1_A619Ht2_Exon2
RLK1_A619Ht2_Exon3

Majority             NPSAFDNLTFFFGCHWGPRDTLPEFAGNNISCAGFSTPAISGGGSFVFKPEDLDEHAEQELASHCDEVFSVPVRSEALQQ
                     ---------+---------+---------+---------+---------+---------+---------+---------+
                             170       180       190       200       210       220       230       240
                     ---------+---------+---------+---------+---------+---------+---------+---------+
RLK1_A619HT2_CDS     NPSAFDNLTFFFGCHWGPRDTLPEFAGNNISCAGFSTPAISGGGSFVFKPEDLDEHAEQELASHCDEVFSVPVRSEALQQ
RLK1_A619HT3_CDS     NPSAFDNLTFFFGCHWGPRDTLPEFAGNNISCAGFSTPAISGGGSFVFKPEDLDEHAEQELASHCDEVFSVPVRSEALQQ
RLK1_B37HTN_CDS      NASAFDNLTFFFGCHWGPRNTPPEFADYNISCAGFNTPTISGGRSFVFKTGDLDEQEEQELALHCDEVFSVPVRRDALQ-
RLK1_A619HT2_Exon1   NPSAFDNLTFFFGCHWGPRDTLPEFAGNNISCAGFSTPAISGGGSFVFKPEDLDEHAEQELASHCDEVFSVPVRSEALQQ
RLK1_A619Ht2_Exon2
RLK1_A619Ht2_Exon3

Majority             AIVSNLSL--DGYGELLRQGIELEWKRTSEDQCGQCEESGSGGRCAYSQKREFLGCFCSGGKAGNPFCKPSRSTKRREAA
                     ---------+---------+---------+---------+---------+---------+---------+---------+
                             250       260       270       280       290       300       310       320
                     ---------+---------+---------+---------+---------+---------+---------+---------+
RLK1_A619HT2_CDS     AIVSNLSL--DGYGELLRQGIELEWKRTSEDQCGQCEESGSGGRCAYSQKREFLGCFCSGGKAGNPFCKPSRSTKRREAA
RLK1_A619HT3_CDS     AIVSNLSL--DGYGELLRQGIELEWKRTSEDQCGQCEESGSGGRCAYSQKREFLGCFCSGGKAGNPFCKPSRSTKRREAA
RLK1_B37HTN_CDS      AIVSNFSLTRDGYGEVLRQGFELEWNRTSEDQCGRCEGSGSGGWCAYSQKREFLGCLCSGGKVGSPFCKPSRS-KRKEG-
RLK1_A619HT2_Exon1   AIVSNLSL--DGYGELLRQGIELEWKRTSEDQCGQCEESGSGGRCAYSQKREFLGCFCSGGKAGNPFCKPSR
RLK1_A619Ht2_Exon2                                                                           STKRREAA
RLK1_A619Ht2_Exon3

Majority             SIVGAVAVAFLCLVILTCFLACRHCSLPFKSKNKPGTRIESFLQKNESSIHPKRYTYADVKRMTKSFAVKLGQGGFGAVY
                     ---------+---------+---------+---------+---------+---------+---------+---------+
                             330       340       350       360       370       380       390       400
                     ---------+---------+---------+---------+---------+---------+---------+---------+
RLK1_A619HT2_CDS     SIVGAVAVAFLCLVILTCFLACRHCSLPFKSKNKPGTRIESFLQKNESSIHPKRYTYADVKRMTKSFAVKLGQGGFGAVY
RLK1_A619HT3_CDS     SIVGAVAVAFLCLVILTCFLACRHCSLPFKSKNKPGTRIESFLQKNESSIHPKRYTYADVKRMTKSFAVKLGQGGFGAVY
RLK1_B37HTN_CDS      PIVGAVAVAFLCLVILTCFLACRHGSLPFKSENKPGTRIESFLQKNES--HPKRYTYADVKRMTKSFAVKLGQGGFGAVY
RLK1_A619HT2_Exon1
RLK1_A619Ht2_Exon2   SIVG
RLK1_A619Ht2_Exon3       AVAVAFLCLVILTCFLACRHCSLPFKSKNKPGTRIESFLQKNESSIHPKRYTYADVKRMTKSFAVKLGQGGFGAVY

Majority             KGSLHDGRQVAVKMLKDTQGDGEEFMNEVASISRTSHVNVVTLLGFCLQGSKRALIYEYMPNGSLERYAFTGDMNSENLL
                     ---------+---------+---------+---------+---------+---------+---------+---------+
                             410       420       430       440       450       460       470       480
                     ---------+---------+---------+---------+---------+---------+---------+---------+
RLK1_A619HT2_CDS     KGSLHDGRQVAVKMLKDTQGDGEEFMNEVASISRTSHVNVVTLLGFCLQGSKRALIYEYMPNGSLERYAFTGDMNSENLL
RLK1_A619HT3_CDS     KGSLHDGRQVAVKMLKDTQGDGEEFMNEVASISRTSHVNVVTLLGFCLQGSKRALIYEYMPNGSLERYAFTGDMNSENLL
RLK1_B37HTN_CDS      KGSLHDGRQVAVKMLKDTQGDGEEFMNEVASISRTSHVNVVTLLGFCLQGSKRALIYEYMPNGSLERYAFTGDMNSENLL
RLK1_A619HT2_Exon1
RLK1_A619Ht2_Exon2
RLK1_A619Ht2_Exon3   KGSLHDGRQVAVKMLKDTQGDGEEFMNEVASISRTSHVNVVTLLGFCLQGSKRALIYEYMPNGSLERYAFTGDMNSENLL
```

FIG 3 B

```
Majority             TWERLFDIAIGTARGLEYLHRGCNTRIVHFDIKPHNILLDQDFCPKISDFGLAKLCLNKESAISIAGARGTIGYIAPEVY
                     ---------+---------+---------+---------+---------+---------+---------+---------+
                              490       500       510       520       530       540       550       560
                     ---------+---------+---------+---------+---------+---------+---------+---------+
RLK1_A619HT2_CDS     TWERLFDIAIGTARGLEYLHRGCNTRIVHFDIKPHNILLDQDFCPKISDFGLAKLCLNKESAISIAGARGTIGYIAPEVY
RLK1_A619HT3_CDS     TWERLFDIAIGTARGLEYLHRGCNTRIVHFDIKPHNILLDQDFCPKISDFGLAKLCLNKESAISIAGARGTIGYIAPEVY
RLK1_B37HTN_CDS      TWERLFDIAIGTARGLEYLHRGCNTRIVHFDIKPHNILLDQDFCPKISDFGLAKLCLNKESAISIAGARGTIGYIAPEVY
RLK1_A619HT2_Exon1
RLK1_A619Ht2_Exon2
RLK1_A619Ht2_Exon3   TWERLFDIAIGTARGLEYLHRGCNTRIVHFDIKPHNILLDQDFCPKISDFGLAKLCLNKESAISIAGARGTIGYIAPEVY

Majority             SKQFGTISSKSDVYSYGMMVLEMVGARDRNTSADSDHSSQYFPQWLYEHLDDYCVGASEINGETTELVRKMIVVGLWCIQ
                     ---------+---------+---------+---------+---------+---------+---------+---------+
                              570       580       590       600       610       620       630       640
                     ---------+---------+---------+---------+---------+---------+---------+---------+
RLK1_A619HT2_CDS     SKQFGTISSKSDVYSYGMMVLEMVGARDRNTSADSDHSSQYFPQWLYEHLDDYCVGASEINGETTELVRKMIVVGLWCIQ
RLK1_A619HT3_CDS     SKQFGTISSKSDVYSYGMMVLEMVGARDRNTSADSDHSSQYFPQWLYEHLDDYCVGASEINGETTELVRKMIVVGLWCIQ
RLK1_B37HTN_CDS      SKQFGIISSKSDVYSYGMMVLEMVGARDRNTSADSDHSSQYFPQWLYEHLDDYCVGASEINGETTELVRKMIVVGLWCIQ
RLK1_A619HT2_Exon1
RLK1_A619Ht2_Exon2
RLK1_A619Ht2_Exon3   SKQFGTISSKSDVYSYGMMVLEMVGARDRNTSADSDHSSQYFPQWLYEHLDDYCVGASEINGETTELVRKMIVVGLWCIQ

Majority             VIPTDRPTMTRVVEMLEGSTSNLELPPRVLLS-
                     ---------+---------+---------+---
                              650       660       670
                     ---------+---------+---------+---
RLK1_A619HT2_CDS     VIPTDRPTMTRVVEMLEGSTSNLELPPRVLLS.
RLK1_A619HT3_CDS     VIPTDRPTMTRVVEMLEGSTSNLELPPRVLLS.
RLK1_B37HTN_CDS      VIPTDRPTMTRVVEMLEGSTSNLELPPRVLLS.
RLK1_A619HT2_Exon1
RLK1_A619Ht2_Exon2
RLK1_A619Ht2_Exon3   VIPTDRPTMTRVVEMLEGSTSNLELPPRVLLS.
```

FIG 4 A

```
SEQ ID NO: 2      1 atggctgctcacctaccacgcctccccgtcctcctcctcgtcctcctcgc  50
                    ||||||||||||||||||||||||||||||||||||||||||||||||||
SEQ ID NO: 21     1 atggctgctcacctaccacgcctccccgtcctcctcctcgtcctcctcgc  50

SEQ ID NO: 2     51 tgcccatgtcgtctccacctccgcccatgccgagcctcctcttccgagcc  100
                    ||||||||||||||||||||||||||||||||||||||||||||||||||
SEQ ID NO: 21    51 tgcccatgtcgtctccacctccgcccatgccgagcctcctcttccgagcc  100

SEQ ID NO: 2    101 cttacagcacctccgcccatggcgagcctcctcttccgagcacttacaac  150
                    ||||||||||||||||||||||||||||||||||||||||||||||||||
SEQ ID NO: 21   101 cttacagcacctccgcccatggcgagcctcctcttccgagcacttacaac  150

SEQ ID NO: 2    151 gtctccatgtgctcggaatcgttctggtgcggcggcgtcgaaatccgcta  200
                    |||||||||||||||||||||||||||||||||||||||.||||||||||
SEQ ID NO: 21   151 gtctccatgtgctcggaatcgttctggtgcggcggcgtcnaaatccgcta  200

SEQ ID NO: 2    201 cccgttctatcttgccaacgcaaccgccgactacagcgggagctactact  250
                    ||||||||||||||||||||||||||||||||||||||||||||||||||
SEQ ID NO: 21   201 cccgttctatcttgccaacgcaaccgccgactacagcgggagctactact  250

SEQ ID NO: 2    251 cctgcggctacaccgacttgagcgtttcctgcaaactcgaggtcgagggg  300
                    |||||||||||.||||||||||||||||||||||||||||||||||||||
SEQ ID NO: 21   251 cctgcggctacnccgacttgagcgtttcctgcaaactcgaggtcgagggg  300

SEQ ID NO: 2    301 ccgacgacgacatggacccctaccatccgtctcggcggcgacaactacac  350
                    ||||||||||||||||||||||||||||||||||||||||||||||||||
SEQ ID NO: 21   301 ccgacgacgacatggacccctaccatccgtctcggcggcgacaactacac  350

SEQ ID NO: 2    351 cgtcaagaacatcttgtacgactatcataccatctcactggcggacagcg  400
                    ||||||||||||||||||||||||||||||||||||||||||||||||||
SEQ ID NO: 21   351 cgtcaagaacatcttgtacgactatcataccatctcactggcggacagcg  400

SEQ ID NO: 2    401 atgtgctcggaggcggcgagtgccccgtcgtccaccacaacgtcagcttc  450
                    ||||||||||||||||||||||||||||||||||||||||||||||||||
SEQ ID NO: 21   401 atgtgctcggaggcggcgagtgccccgtcgtccaccacaacgtcagcttc  450

SEQ ID NO: 2    451 gacgagacgtggctgcacaaccccagcgccttcgacaacctcaccttctt  500
                    ||||||||||||||||||||||||||||||||||||||||||||||||||
SEQ ID NO: 21   451 gacgagacgtggctgcacaaccccagcgccttcgacaacctcaccttctt  500

SEQ ID NO: 2    501 cttcggatgccactgggggccacgcgatacactgcctgaatttgccggca  550
                    ||||||||||||||||||||||||||||||||||||||||||||||||||
SEQ ID NO: 21   501 cttcggatgccactgggggccacgcgatacactgcctgaatttgccggca  550

SEQ ID NO: 2    551 acaacatcagctgcgccgggttcagtactccagctatcagcggtggaggc  600
                    ||||||||||||||||||||||||||||||||||||||||||||||||||
SEQ ID NO: 21   551 acaacatcagctgcgccgggttcagtactccagctatcagcggtggaggc  600

SEQ ID NO: 2    601 tccttcgtgttcaagcctgaagatcttgacgaacatgcggagcaggagtt  650
                    ||||||||||||||||||||||||||||||||||||||||||||||||||
SEQ ID NO: 21   601 tccttcgtgttcaagcctgaagatcttgacgaacatgcggagcaggagtt  650

SEQ ID NO: 2    651 ggcttcacactgcgacgaggttttctccgtgccagtgagaagcgaggctc  700
                    ||||||||||||||||||||||||||||||||||||||||||||||||||
SEQ ID NO: 21   651 ggcttcacactgcgacgaggttttctccgtgccagtgagaagcgaggctc  700

SEQ ID NO: 2    701 tgcagcaggcgatcgtcagcaacctcagcctcggggacgggtacggcgag  750
                    ||||||||||||||||||||||||||||||||||||||||||||||||||
SEQ ID NO: 21   701 tgcagcaggcgatcgtcagcaacctcagcctcggggacgggtacggcgag  750

SEQ ID NO: 2    751 ctgcttaggcaggggatcgagttggaatggaaacggacatcggaggatca  800
                    ||||||||||||||||||||||||||||||||||||||||||||||||||
SEQ ID NO: 21   751 ctgcttaggcaggggatcgagttggaatggaaacggacatcggaggatca  800

SEQ ID NO: 2    801 gtgtggccagtgcgaggaatcgggctccggcggacggtgcgcctacagcc  850
                    ||||||||||||||||||||||||||||||||||||||||||||||||||
SEQ ID NO: 21   801 gtgtggccagtgcgaggaatcgggctccggcggacggtgcgcctacagcc  850

SEQ ID NO: 2    851 agaagagagaattccttggctgcttctgcagcggagggaaggcgggcaac  900
                    |||||||||||||||||||||||||.||||||||||||||||||||||||
SEQ ID NO: 21   851 agaagagagaattccttggctgcttgtgcagcggagggaaggcgggcaac  900
```

FIG 4 B

```
SEQ ID NO: 2      901 ccgttctgcaaaccatcaagatcaacaaaaaggagagaagcagcatctat   950
                      ||||||||||||||||||||||||||||||||||||||||||||||||||
SEQ ID NO: 21     901 ccgttctgcaaaccatcaagatcaacaaaaaggagagaagcagcatctat   950

SEQ ID NO: 2      951 tgttggtgctgttgccgttgcattcctgtgtctagtcattctcacatgct  1000
                      ||||||||||||||||||||||||||||||||||||||||||||||||||
SEQ ID NO: 21     951 tgttggtgctgttgccgttgcattcctgtgtctagtcattctcacatgct  1000

SEQ ID NO: 2     1001 tcttggcttgtagacattgttcgctgcccttcaaatcgaagaacaaacca  1050
                      |||||||||||||||||.||||||||||||||||||||.|||||||||||
SEQ ID NO: 21    1001 tcttggcttgtagacatggttcgctgcccttcaaatcggagaacaaacca  1050

SEQ ID NO: 2     1051 gggacaaggattgagtccttcctacagaagaacgagagtagtatacatcc  1100
                      ||||||||||||||||||||||||||||||||||||   |||||||||||
SEQ ID NO: 21    1051 gggacaaggattgagtccttcctacagaagaacgag---agtatacatcc  1097

SEQ ID NO: 2     1101 gaaaagatacacctacgcggacgtgaaaagaatgacaaaatccttcgctg  1150
                      ||||||||||||||||||||||||||||||||||||||||||||||||||
SEQ ID NO: 21    1098 gaaaagatacacctacgcggacgtgaaaagaatgacaaaatccttcgctg  1147

SEQ ID NO: 2     1151 tgaagctaggccaaggtgggtttggtgctgtatacaaaggcagcctccac  1200
                      ||||||||||||||||||||||||||||||||||||||||||||||||||
SEQ ID NO: 21    1148 tgaagctaggccaaggtgggtttggtgctgtatacaaaggcagcctccac  1197

SEQ ID NO: 2     1201 gatggccgacaggtagcagtcaagatgctgaaggacacccaaggtgacgg  1250
                      |||||||||||||||||||||||||||||.||||||||||||||||||||
SEQ ID NO: 21    1198 gatggccgacaggtagcagtcaagatgctcaaggacacccaaggtgacgg  1247

SEQ ID NO: 2     1251 cgaggaattcatgaacgaggtggctagcatcagcaggacttctcatgtca  1300
                      ||||||||||||||||||||||||||||||||||||||||||||||||||
SEQ ID NO: 21    1248 cgaggaattcatgaacgaggtggctagcatcagcaggacttctcatgtca  1297

SEQ ID NO: 2     1301 acgtcgtgacacttctagggttttgcttgcaagggtcgaaaagagcactg  1350
                      ||||||||||||||||||||||||||||||||||||||||||||||||||
SEQ ID NO: 21    1298 acgtcgtgacacttctagggttttgcttgcaagggtcgaaaagagcactg  1347

SEQ ID NO: 2     1351 atctacgagtacatgcccaatggttcgctcgaaaggtatgccttcaccgg  1400
                      ||||||||||||||||||||||||||||||||||||||||||||||||||
SEQ ID NO: 21    1348 atctacgagtacatgcccaatggttcgctcgaaaggtatgccttcaccgg  1397

SEQ ID NO: 2     1401 tgacatgaacagtgagaatttgctaacctgggaaagactatttgacatag  1450
                      ||||||||||||||||||||||||||||||||||||||||||||||||||
SEQ ID NO: 21    1398 tgacatgaacagtgagaatttgctaacctgggaaagactatttgacatag  1447

SEQ ID NO: 2     1451 cgattggcac--ggccagagggctcgaatacctacaccggggatgcaaca  1498
                      |.||||||||  ||||||||||||||||||||||||||||||||||||||
SEQ ID NO: 21    1448 caattggcacacggccagagggctcgaatacctacaccggggatgcaaca  1497

SEQ ID NO: 2     1499 ctcggatcgtgcattttgacatcaagccacacaacatcctgttagaccag  1548
                      ||||||||||||||||||||||||||||||||||||||||||||||||||
SEQ ID NO: 21    1498 ctcggatcgtgcattttgacatcaagccacacaacatcctgttagaccag  1547

SEQ ID NO: 2     1549 gatttctgccctaagatctctgactttggactggccaagctatgtctgaa  1598
                      ||||||||||||||||||||||||||||||||||||||||||||||||||
SEQ ID NO: 21    1548 gatttctgccctaagatctctgactttggactggccaagctatgtctgaa  1597

SEQ ID NO: 2     1599 caaagagagcgctatctccattgctggcgcaagagggacgatagggtata  1648
                      ||||||||||||||||||||||||||||||||||||||||||||||||||
SEQ ID NO: 21    1598 caaagagagcgctatctccattgctggcgcaagagggacgatagggtata  1647

SEQ ID NO: 2     1649 tcgccccggaggtctactcaaagcaatttggaacgatcagcagcaagtct  1698
                      ||||||||||||||||||||||||||||||||||.||.||||||||||||
SEQ ID NO: 21    1648 tcgccccggaggtctactcaaagcaatttggaacaataagcagcaagtct  1697

SEQ ID NO: 2     1699 gatgtctatagctatgggatgatggtccttgagatggttggagcaaggga  1748
                      ||||||||||||||||||||||||||||||||||||||||||||||||||
SEQ ID NO: 21    1698 gatgtctatagctatgggatgatggtccttgagatggttggagcaaggga  1747

SEQ ID NO: 2     1749 caggaatacaagcgcagatagtgaccatagcagccaatatttccctcagt  1798
                      ||||||||||||||||||||||||||||||||||||||||||||||||||
SEQ ID NO: 21    1748 caggaatacaagcgcagatagtgaccatagcagccaatatttccctcagt  1797
```

FIG 4 C

```
SEQ ID NO: 2          1799 ggctttatgaacatttggacgactattgtgttggtgcttccgagattaat   1848
                           ||||||||||.|||||||||||||||||||||||||||||||||||||||
SEQ ID NO: 21         1798 ggctttatgagcatttggacgactattgtgttggtgcttccgagattaat   1847

SEQ ID NO: 2          1849 ggtgagaccacagagctcgtgaggaagatgatagttgtaggtctgtggtg   1898
                           ||||||||||||||||||||||||||||||||||||||||||||||||||
SEQ ID NO: 21         1848 ggtgagaccacagagctcgtgaggaagatgatagttgtaggtctgtggtg   1897

SEQ ID NO: 2          1899 catacaagtgattccgactgatcgaccaacaatgacgagagtcgtcgaga   1948
                           ||||||||||||||||||||||||||||||||||||||||||||||||||
SEQ ID NO: 21         1898 catacaagtgattccgactgatcgaccaacaatgacgagagtcgtcgaga   1947

SEQ ID NO: 2          1949 tgttggaaggaagcacaagtaatctagagttgccacccagagttctcttg   1998
                           ||||||||||||||||||||||||||||||||||||||||||||||||||
SEQ ID NO: 21         1948 tgttggaaggaagcacaagtaatctagagttgccacccagagttctcttg   1997

SEQ ID NO: 2          1999 agctga   2004
                           ||||||
SEQ ID NO: 21         1998 agctga   2003
```

FIG 5

```
SEQ_ID_NO:_3      1 MAAHLPRLPVLLLVLLAAHVVSTSAHAEPPLPSPYSTSAHGEPPLPSTYN   50
                    ||||||||||||||||||||||||||||||||||||||||||||||||||
SEQ_ID_NO:_24     1 MAAHLPRLPVLLLVLLAAHVVSTSAHAEPPLPSPYSTSAHGEPPLPSTYN   50

SEQ_ID_NO:_3     51 VSMCSESFWCGGVEIRYPFYLANATADYSGSYYSCGYTDLSVSCKLEVEG  100
                    |||||||||||||.|||||||||||||||||||||||.||||||||||||
SEQ_ID_NO:_24    51 VSMCSESFWCGGVXIRYPFYLANATADYSGSYYSCGYXDLSVSCKLEVEG  100

SEQ_ID_NO:_3    101 PTTTWTPTIRLGGDNYTVKNILYDYHTISLADSDVLGGGECPVVHHNVSF  150
                    ||||||||||||||||||||||||||||||||||||||||||||||||||
SEQ_ID_NO:_24   101 PTTTWTPTIRLGGDNYTVKNILYDYHTISLADSDVLGGGECPVVHHNVSF  150

SEQ_ID_NO:_3    151 DETWLHNPSAFDNLTFFFGCHWGPRDTLPEFAGNNISCAGFSTPAISGGG  200
                    ||||||||||||||||||||||||||||||||||||||||||||||||||
SEQ_ID_NO:_24   151 DETWLHNPSAFDNLTFFFGCHWGPRDTLPEFAGNNISCAGFSTPAISGGG  200

SEQ_ID_NO:_3    201 SFVFKPEDLDEHAEQELASHCDEVFSVPVRSEALQQAIVSNLSLGDGYGE  250
                    ||||||||||||||||||||||||||||||||||||||||||||||||||
SEQ_ID_NO:_24   201 SFVFKPEDLDEHAEQELASHCDEVFSVPVRSEALQQAIVSNLSLGDGYGE  250

SEQ_ID_NO:_3    251 LLRQGIELEWKRTSEDQCGQCEESGSGGRCAYSQKREFLGCFCSGGKAGN  300
                    |||||||||||||||||||||||||||||||||||||||||.||||||||
SEQ_ID_NO:_24   251 LLRQGIELEWKRTSEDQCGQCEESGSGGRCAYSQKREFLGCLCSGGKAGN  300

SEQ_ID_NO:_3    301 PFCKPSRSTKRREAASIVGAVAVAFLCLVILTCFLACRHCSLPFKSKNKP  350
                    |||||||||||||||||||||||||||||||||||||||.||||||:|||
SEQ_ID_NO:_24   301 PFCKPSRSTKRREAASIVGAVAVAFLCLVILTCFLACRHGSLPFKSENKP  350

SEQ_ID_NO:_3    351 GTRIESFLQKNESSIHPKRYTYADVKRMTKSFAVKLGQGGFGAVYKGSLH  400
                    |||||||||||| |||||||||||||||||||||||||||||||||||||
SEQ_ID_NO:_24   351 GTRIESFLQKNE-SIHPKRYTYADVKRMTKSFAVKLGQGGFGAVYKGSLH  399

SEQ_ID_NO:_3    401 DGRQVAVKMLKDTQGDGEEFMNEVASISRTSHVNVVTLLGFCLQGSKRAL  450
                    ||||||||||||||||||||||||||||||||||||||||||||||||||
SEQ_ID_NO:_24   400 DGRQVAVKMLKDTQGDGEEFMNEVASISRTSHVNVVTLLGFCLQGSKRAL  449

SEQ_ID_NO:_3    451 IYEYMPNGSLERYAFTGDMNSENLLTWERLFDIAIGTARGLEYLHRGCNT  500
                    ||||||||||||||||||||||||||||||||||||||||||||||||||
SEQ_ID_NO:_24   450 IYEYMPNGSLERYAFTGDMNSENLLTWERLFDIAIGTARGLEYLHRGCNT  499

SEQ_ID_NO:_3    501 RIVHFDIKPHNILLDQDFCPKISDFGLAKLCLNKESAISIAGARGTIGYI  550
                    ||||||||||||||||||||||||||||||||||||||||||||||||||
SEQ_ID_NO:_24   500 RIVHFDIKPHNILLDQDFCPKISDFGLAKLCLNKESAISIAGARGTIGYI  549

SEQ_ID_NO:_3    551 APEVYSKQFGTISSKSDVYSYGMMVLEMVGARDRNTSADSDHSSQYFPQW  600
                    ||||||||||||||||||||||||||||||||||||||||||||||||||
SEQ_ID_NO:_24   550 APEVYSKQFGTISSKSDVYSYGMMVLEMVGARDRNTSADSDHSSQYFPQW  599

SEQ_ID_NO:_3    601 LYEHLDDYCVGASEINGETTELVRKMIVVGLWCIQVIPTDRPTMTRVVEM  650
                    ||||||||||||||||||||||||||||||||||||||||||||||||||
SEQ_ID_NO:_24   600 LYEHLDDYCVGASEINGETTELVRKMIVVGLWCIQVIPTDRPTMTRVVEM  649

SEQ_ID_NO:_3    651 LEGSTSNLELPPRVLLS    667
                    |||||||||||||||||
SEQ_ID_NO:_24   650 LEGSTSNLELPPRVLLS    666
```

GENE CONFERRING RESISTANCE TO FUNGAL PATHOGEN

CROSS-REFERENCE TO RELATED APPLICATIONS

This application is a U.S. National Phase of International Patent Application No. PCT/EP2018/072665, filed on Aug. 22, 2018, which claims priority to European Patent application Ser. Nos. 17/187,309.4, filed on Aug. 22, 2017 and 17206305.9, filed on Dec. 8, 2017. The entire contents of these applications are incorporated herein by reference in their entirety.

FIELD OF THE INVENTION

The present invention relates to a nucleic acid molecule encoding a polypeptide conferring resistance to a plant against a fungal pathogen, such as *Helminthosporium turcicum*. The present invention further relates to a plant (or part thereof) comprising the nucleic acid molecule, and methods involving the nucleic acid molecule.

BACKGROUND OF THE INVENTION

In maize (*Zea mays* L.), there are many fungal pathogens which cause leaf diseases. The fungus which can cause by far the most damage under tropical and also under temperate climatic conditions, such as those in large parts of Europe and North America as well as in Africa and India, is known as *Helminthosporium turcicum* or synonymously as *Exserohilum turcicum* (teleomorph: *Setosphaeria turcica*). *H. turcicum* is the cause of the leaf spot disease known as "Northern Corn Leaf Blight" (NCLB), which can occur in epidemic proportions during wet years, attacking vulnerable maize varieties and causing a great deal of damage and considerable losses of yield of 30% and more over wide areas. Since the 1970s, then, natural resistance in genetic material has been sought. Currently, quantitative and qualitative resistances, even if incomplete, are known. While the oligo- or polygenically inherited quantitative resistance appears incomplete and non-specific as regards race in the phenotype and is influenced by additional and partially dominant genes, qualitative resistance seems to be typically race-specific and can be inherited through individual, mostly dominant genes at loci like HT1, HT2, HT3, Htm1 or HTN1 (Lipps et al., 1997, "Interaction of Ht and partial resistance to *Exserohilum turcicum* in maize." *Plant Disease* 81: 277-282; Welz & Geiger, 2000, "Genes for resistance to northern corn leaf blight in diverse maize populations." *Plant Breeding* 119: 1-14). Backcrosses in many frequently used inbred maize lines such as W22, A619, B37 or B73 have successfully brought about introgression of the HT loci, where they exhibit a partial dominance and expression as a function of the respective genetic background (Welz, 1998, "Genetics and epidemiology of the pathosystem *Zea mays/Setosphaeria turcica*" Habilitationsschrift, Institut für Pflanzenzüchtung, Saatgutforschung und Populations-genetik, Universität Hohenheim).

Despite this complex genetic architecture of NCLB resistance in maize, until now, principally, the use of the HT1 gene located on the long arm of chromosome 2 together with a partial quantitative resistance has been sufficient to control helminthosporiosis in maize (Welz, 1998). The basis for this is that globally, races 0 and 1 of *H. turcicum* are most prevalent (approximately 55%) (Lipps et al., 1997), while other races such as 2N and 23N are only rare and even in geographically restricted areas (Welz, 1998). This race 0 is avirulent with regard to a maize plant with HT1 (see also Table 1), so that when provided with a suitable quantitative resistance, it exhibits a sufficient general resistance to NCLB. However, many studies have reported an increasing dissemination of the less common races (Jordan et al., 1983, "Occurrence of race 2 of *Exserohilum turcicum* on corn in the central and eastern United States." *Plant Disease* 67: 1163-1165; Welz, 1998). The reasons for this are linked to the population dynamic of a pathogen which allows changes in pathogen virulence by new mutations in avirulence genes and new combinations of available virulence genes. This can lead to the occurrence of new, sometimes more aggressive pathogenic races. In Brazil, for example, the *H. turcicum* population already appears to be substantially more diverse with regard to the race composition than, for example, in North America. Already in the 1990s it has been reported that *H. turcicum* races had broken the resistance conferred by the HT1 gene. In addition, there is the instability of the resistance genes to certain environmental factors such as temperature and light intensity in some climate zones (Thakur et al., 1989, "Effects of temperature and light on virulence of *Exserohilum turcicum* on corn." Phytopathology 1989, 79: 631-635). As a consequence, the use of novel HT resistance genes for the production of commercial maize plants in order to target a broader and more long-lasting resistance to *H. turcicum* in maize is growing in importance.

TABLE 1

Overview of resistance (R) and susceptibility (S) of resistance loci against different *Helminthosporium turcicum* races:

| Pathogen | Host (Ht) reaction to each race | | | |
|---|---|---|---|---|
| Ht Race Designation | HT1 locus | HT2 locus | HT3 locus | HTN1 gene |
| 0 | R | R | R | R |
| 1 | S | R | R | R |
| 2 | R | S | R | R |
| 3 | R | R | S | R |
| N | R | R | R | S |
| 12 | S | S | R | R |
| 23 | R | S | S | R |
| 2N | R | S | R | S |
| 12N | S | S | R | S |
| 23N | R | S | S | S |
| 123N | S | S | S | S |

One source of monogenic HTN1 resistance is the Mexican landrace "Pepitilla" (Gevers, 1975, "A new major gene for resistance to *Helminthosporium turcicum* leaf blight of maize." *Plant Dis Rep* 59: 296-300). HTN1 introgression lines exhibit a gene mapping on the long arm of chromosome 8. In contrast to the usual HT resistance genes, HTN1 confers resistance by delaying the onset of sporulation, and thus combats the development of lesions. As a result, fewer, smaller lesions as well as reduced sporulation zones are formed (Simcox & Bennetzen, 1993, "The use of molecular markers to study *Setospaeria turcica* resistance in maize." Phytopathology 83: 1326-1330). Chlorotic-necrotic lesions such as those which occur with HT1, HT2 or HT3-conferred resistance, are not formed (Gevers, 1975). WO2015/032494 discloses the identification of the causative gene, RLK1, conferring the "Pepitilla" resistance phenotype on bin 8.06 in corn and describes molecular markers which are suitable to benefit from this resistance locus without close-linked, undesired linkage drag leading to a negative impact on the yield potential.

In WO2011/163590 the genotypes PH99N and PH26N have been discloses as alternative sources for NCLB resistance on chromosome 8 bin 5.

With the intention of identifying a resistance gene for NCLB from the maize hybrid DK888, in 2010, Chung et al. published a study for fine mapping the bin 8.06 resistance locus (Chung et al. 2010 "Characterization and fine-mapping of a resistance locus for northern leaf blight in maize bin 8.06" Theoretical and Applied Genetics 121(2): 205-227). Investigations on *Helminthosporium* race specificity initially made it clear that functionally, the resistance locus was closely linked with the HT2 and HTN1 genes. Genome annotations of a 0.46 Mb-sized chromosome fragment using B73 reference hinted at several putative open reading frames; however, the causative gene has not been identified and a functional verification was not described.

It is thus an objective of the present invention to identify and/or further characterize plant resistance genes encoding polypeptides conferring or increasing resistance against a fungal pathogen, such as *Helminthosporium turcicum.*

SUMMARY OF THE INVENTION

The present invention provides a nucleic acid molecule comprising or consisting of a nucleotide sequence having the nucleotide sequence set forth in SEQ ID NO: 1 or SEQ ID NO: 2. Also provided is a nucleic acid molecule comprising or consisting of a nucleotide sequence encoding the amino acid sequence set forth in SEQ ID NO: 3.

Further provided is a nucleic acid molecule comprising or consisting of a nucleotide sequence having at least 96% identity to the nucleotide sequence set forth in SEQ ID NO: 1 or SEQ ID NO: 2 and a nucleic acid molecule comprising or consisting of a nucleotide sequence encoding an amino acid sequence having at least 92% identity to the amino acid sequence set forth in SEQ ID NO: 3.

Also provided is a nucleic acid molecule comprising or consisting of a nucleotide sequence hybridizing with the complementary strand of the nucleotide sequence set forth in SEQ ID NO: 1 or SEQ ID NO: 2 or hybridizing with the complementary strand of the nucleotide sequence encoding the amino acid sequence set forth in SEQ ID NO: 3 under stringent hybridization conditions.

Moreover, provided is a nucleic acid molecule comprising or consisting of a nucleotide sequence encoding a protein, said protein being derived from the amino acid sequence encoded by the nucleotide sequence of SEQ ID NO: 1 or SEQ ID NO: 2 or from the amino acid sequence set forth in SEQ ID NO: 3 by way of substitution, deletion and/or addition of one or more amino acid(s).

The nucleic acid molecule according to the present invention encodes a polypeptide which is a wall associated receptor-like kinases 1 (WAK RLK1) or functionally belongs to the family of wall associated receptor-like kinases.

The nucleic acid molecule of the invention is encoding a polypeptide capable of conferring (or increasing) resistance to a plant disease caused by fungal pathogen, in particular by *Helminthosporium turcicum*, preferably by *Helminthosporium turcicum* races 0, 1 and/or N in a plant, preferably in a plant of the species *Zea mays*, in which the polypeptide is expressed.

In another aspect, provided is a vector or expression cassette comprising the nucleic acid molecule of the present invention. Preferably, in the vector or expression cassette, the nucleotide sequence of the invention is operably linked to a regulatory element allowing expression of the nucleotide sequence in a plant cell.

Further provided is a host cell comprising the nucleic acid molecule of the invention or the vector or expression cassette of the invention.

In another aspect, a polypeptide encoded by the nucleic acid molecule of the invention is provided. The polypeptide is a wall associated receptor-like kinases 1 (WAK RLK1) or functionally belongs to the family of wall associated receptor-like kinases 1. Preferably, the polypeptide is capable of conferring (or increasing) resistance to a plant disease caused by *Helminthosporium turcicum*, preferably by *Helminthosporium turcicum* races 0, 1 and/or N in a plant, preferably in a plant of the species *Zea mays*, in which the polypeptide is expressed.

Additionally, the polypeptide may not be capable of conferring or increasing resistance to a plant disease caused by *Helminthosporium turcicum* races 2 and/or 3 in a plant, preferably a plant of the species *Zea mays*, in which the polypeptide is expressed. The plant may show a susceptible response to infection with *Helminthosporium turcicum* races 2 and/or 3.

Furthermore, provided is a plant, preferably a plant of the species *Zea mays*, comprising the nucleic acid molecule of the invention transgenically (as transgene) or endogenously (as endogenous gene), the vector of the invention, the expression cassette of the invention, or the polypeptide of the invention. Preferably, the plant is resistant to a plant disease caused by *Helminthosporium turcicum*, in particular by *Helminthosporium turcicum* races 0, 1 and/or N. The plant may show a susceptible response to infection with *Helminthosporium turcicum* races 2 and/or 3. The plant may be a transgenic plant or a genetically edited plant. The plant may be a plant comprising the nucleic acid molecule of the invention endogenously, wherein the genomic flanking regions does not contain an A619HT2 or A619HT3 derived interval located between alleles of marker SYN14136 and marker MA0021 or an A619HT2 or A619HT3 derived interval located between alleles of marker MA0022 and marker SYN4196. A part of the plant of the invention, plant cell of the plant of the invention and seed of the plant of the invention is also provided, wherein the seed comprising the nucleic acid molecule of the invention transgenically (as transgene) or endogenously (as endogenous gene), the vector of the invention, the expression cassette of the invention, or the polypeptide of the invention.

According to another aspect, provided is a method or process of identifying or selecting a plant, preferably a plant of the species *Zea mays*, having increased resistance to a plant disease caused by fungal pathogen, preferably by *Helminthosporium turcicum*, more preferably by *Helmintosporium turcicum* races 0, 1 and/or N, or a part, a cell or a seed thereof, comprising the following steps: (a) detecting in the plant, or part, cell or seed thereof (or in a sample of the plant, or part, cell or seed thereof), the presence of the nucleic acid molecule of the present invention as described above or a nucleic acid molecule comprising or consisting of a nucleotide sequence selected from the group consisting of: (i) a nucleotide sequence having at least 60% identity to the nucleotide sequence set forth in SEQ ID NO: 1 or SEQ ID NO: 2, (ii) a nucleotide sequence encoding an amino acid sequence having at least 60% identity to the amino acid sequence set forth in SEQ ID NO: 3, (iii) a nucleotide sequence having at least 85% identity to nucleotide positions 1-920 of the nucleotide sequence set forth in SEQ ID NO: 1 or SEQ ID NO: 2 (Exon 1: SEQ ID NO: 6) and/or having at least 60% identity to nucleotide positions 23252-23288 of the nucleotide sequence set forth in SEQ ID NO: 1 (Exon 2; SEQ ID NO: 7) or to nucleotide positions 921-957 of the nucleotide sequence set forth in SEQ ID NO: 2 (Exon 2; SEQ ID NO: 7) and/or having at least 98% identity to nucleotide positions 23586-24632 of the nucleotide sequence set forth in SEQ ID NO: 1 (Exon 3; SEQ ID NO: 8) or to nucleotide positions 958-2004 of the nucleotide sequence set forth in SEQ ID NO: 2 (Exon 3; SEQ ID NO: 8), (iv) a nucleotide sequence encoding an amino acid sequence having at least 75% identity to the positions 1-306 of amino acid sequence set forth in SEQ ID NO: 3 and/or having at least 60% identity to positions 307-319 of amino acid sequence set forth in SEQ ID NO: 3 and/or having at least 98% identity to positions 320-668 of amino acid sequence set forth in SEQ ID NO: 3, wherein the nucleic acid molecule of any one of (i) to (iv) is encoding a polypeptide capable of conferring or increasing resistance to a plant disease caused by fungal pathogen, preferably by *Helminthosporium turcicum*, more preferably by *Helminthosporium turcicum* races 0, 1 and/or N, in a plant, preferably a plant of the species *Zea mays*, in which the polypeptide is expressed, and wherein preferably the nucleic acid molecule of any one of (i) to (iv) encodes a polypeptide which is or belongs functionally to the family of wall associated receptor-like kinases 1 (WAK RLK1); and (b) identifying or selecting the plant in which or in whose part, cell or seed the nucleic acid molecule as defined in (a) is present, as having a resistance or an increased resistance to a plant disease caused by a fungal pathogen, preferably by *Helminthosporium turcicum*, more preferably by *Helminthosporium turcicum* races 0, 1 and/or N.

Further provided is, a method or process of identifying a plant, preferably a plant of the species *Zea mays*, which is resistant to a plant disease caused by *Helminthosporium turcicum*, in particular by *Helminthosporium turcicum* races 0, 1 and/or N and comprises the nucleic acid molecule of the invention endogenously, the method or process comprising detecting in the plant alleles of at least two markers, wherein at least one of said markers is on or within the chromosomal interval between SYN14136 and the nucleic acid molecule of the invention, and at least one of said markers is on or within the chromosomal interval between the nucleic acid molecule of the invention and SYN4196.

In another aspect, provided is a plant identified or selected by the method or process of identifying or selecting according to the present invention, or progeny thereof.

In another aspect, provided is a method of identifying an allele of a resistance gene conferring or increasing resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, in *Zea mays* and preferably encoding a polypeptide which is or belongs functionally to the family of wall associated receptor-like kinases 1 (WAK RLK1), wherein the method comprises the following steps: (a) conducting sequence comparison using (i) at least one coding nucleotide sequence originating or derived from a *Zea mays* genotype, wherein the nucleotide sequence preferably maps to bin 8.05 resistance locus or to bin 8.06 resistance locus, and (ii) as reference sequence, a nucleotide sequence of the invention, preferably the nucleotide sequence set forth in SEQ ID NO: 1 or SEQ ID NO: 2 or the nucleotide sequence encoding the amino acid sequence set forth in SEQ ID NO: 3, or a part thereof, or a consensus sequence derived from a set of at least two nucleotide sequences wherein one nucleotide sequence is the nucleotide sequence of the invention, preferably the nucleotide sequence set forth in SEQ ID NO: 1 or SEQ ID NO: 2 or the nucleotide sequence encoding the amino acid sequence set forth in SEQ ID NO: 3, or a part thereof, and wherein each nucleotide sequence of the set of at least two nucleotide sequences encodes a polypeptide capable of conferring or increasing resistance to a plant disease caused by fungal pathogen, preferably by *Helminthosporium turcicum*, more preferably by *Helminthosporium turcicum* races 0, 1 and/or N, in *Zea mays* in which the polypeptide is expressed, and preferably maps to bin 8.05 resistance locus or to bin 8.06 resistance locus and preferably encoding a polypeptide which is or belongs functionally to the family of wall associated receptor-like kinases 1 (WAK RLK1); and (b) identifying the allele, if the sequence comparison reveals (i) a sequence identity on nucleotide level of at least 85% identity to nucleotide positions 1-920 of the nucleotide sequence set forth in SEQ ID NO: 1 or SEQ ID NO: 2 and/or of at least 60% identity to nucleotide positions 23252-23288 of the nucleotide sequence set forth in SEQ ID NO: 1 or to nucleotide positions 921-957 of the nucleotide sequence set forth in SEQ ID NO: 2 and/or of at least 98% identity to nucleotide positions 23586-24632 of the nucleotide sequence set forth in SEQ ID NO: 1 or to nucleotide positions 958-2004 of the nucleotide sequence set forth in SEQ ID NO: 2, and/or (ii) a sequence identity of encoded amino acid level of at least 75% identity to the positions 1-306 of amino acid sequence set forth in SEQ ID NO: 3 and/or of at least 60% identity to positions 307-319 of amino acid sequence set forth in SEQ ID NO: 3 and/or of at least 98% identity to positions 320-668 of amino acid sequence set forth in SEQ ID NO: 3.

Further provided is a nucleic acid molecule comprising or consisting of a nucleotide sequence of the allele of a resistance gene identified by the method of identifying an allele of a resistance gene.

In another aspect, provided is a method for conferring or increasing resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, in a plant, preferably a plant of the species *Zea mays*, comprising the following steps: (a) introducing into at least one cell of the plant the nucleic acid molecule of the present invention, including for example a nucleic acid molecule comprising or consisting of a nucleotide sequence of the identified allele, the expression cassette of the invention or the vector of the invention, (b) regenerating the plant from the at least one cell, and (c) causing expression of the nucleic acid molecule in the plant.

Further provided is a method for increasing resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, in a plant of the invention, comprising the step of reducing the level of expression of the nucleic acid molecule of the present invention, including for example a nucleic acid molecule comprising or consisting of a nucleotide sequence of the identified allele, the expression cassette of the invention or the vector of the invention, in the plant or at least one cell of the plant, preferably compared to the expression level of the endogenous gene in a resistant wild type plant.

In a further aspect, provided is a method for producing a plant, preferably a plant of the species *Zea mays*, having (increased) resistance to a plant disease caused by fungal pathogen, preferably by *Helminthosporium turcicum*, more preferably by *Helminthosporium turcicum* races 0, 1, 2, 3, N, 12, 23, 2N, 12N, 23N and/or 123N, or a part, a cell or a seed thereof, comprising the following steps: (a) introducing into the plant or at least one cell of the plant the nucleic acid molecule of the present invention, including for example a nucleic acid molecule comprising or consisting of a nucleotide sequence of the identified allele, the expression cassette of the invention or the vector of the invention, (b) optionally, regenerating the plant from the at least one cell, and (c) causing expression of the nucleic acid molecule in the plant.

In another aspect, provided is a plant produced by the methods for producing a plant according to the present invention, or progeny thereof.

Further provided is a method for controlling infestation of a fungal pathogen, preferably *Helminthosporium turcicum*, more preferably *Helminthosporium turcicum* races 0, 1, 2, 3, N, 12, 23, 2N, 12N, 23N and/or 123N, in a population of plants, preferably plants of the species *Zea mays*, comprising the following steps: (a) growing plants of the present invention on agricultural and horticultural fields, and (b) causing expression of the nucleic acid molecule of the present invention, including for example a nucleic acid molecule comprising or consisting of a nucleotide sequence of the identified allele, the expression cassette of the invention or the vector of the invention, in the plants.

Another aspect of the invention is an oligonucleotide having a length of at least 15, 16, 17, 18, 19 or 20, preferably at least 21, 22, 23, 24 or 25, more preferred at least 30, 35, 40, 45, 50, 100, 200, 300 or 500 nucleotides, wherein the oligonucleotide is able to hybridize or anneal to (i) the nucleic acid molecule of the invention, (ii) the nucleic acid molecule comprising the nucleotide sequence of SEQ ID NO: 4 or SEQ ID NO: 5, or (iii) nucleic acid molecule complementary to (i) or (ii).

Further provided is a pair of oligonucleotides or a kit comprising said oligonucleotides, wherein the oligonucleotides are suitable to anneal as forward primer and reverse primer to a region in the plant genome, preferably the *Zea mays* genome, which shows a cosegregation, preferably a perfect cosegregation, with the nucleic acid molecule of the invention.

In a further aspect, provided is the use of at least one oligonucleotide as a molecular marker or part thereof in the method of identifying or selecting a plant, preferably a plant of the species *Zea mays*, having increased resistance to a plant disease caused by fungal pathogen, preferably by *Helminthosporium turcicum*, more preferably by *Helmintthosporium turcicum* races 0, 1 and/or N, or a part, a cell or a seed thereof, or in the method of identifying an allele of a resistance gene conferring or increasing resistance to a plant disease caused by a fungal pathogen, preferably by *Helminthosporium turcicum*, more preferably by *Helminthosporium turcicum* races 0, 1 and/or N, in *Zea mays*, wherein the molecular marker is able to detect at least one single nucleotide polymorphism, deletion or insertion diagnostic for the nucleic acid molecule of the present invention and/or comprises the oligonucleotide as described above and/or is the pair of oligonucleotides or the kit as described above.

In one aspect, provided is the use of at least one or at least two oligonucleotide(s) as a molecular marker or part thereof in method or process of identifying a plant as described above or in a method or process for the elimination of linkage drag close linked to the nucleic acid molecule of the invention for detecting the presence or absence of an A619HT2 or A619HT3 derived interval located between alleles of marker SYN14136 and marker MA0021 or an A619HT2 or A619HT3 derived interval located between alleles of marker MA0022 and marker SYN4196.

In another aspect, provided is a method for detecting the presence or absence of the nucleic acid molecule of the invention, including for example a nucleic acid molecule comprising or consisting of a nucleotide sequence of the identified allele, in a plant, preferably a plant of the species *Zea mays*, comprising the following steps: (a) isolating DNA from at least one cell of the plant, and (b) using a molecular marker to detect the presence or absence of the nucleic acid molecule of the invention, wherein the molecular marker is able to detect at least one single nucleotide polymorphism, deletion or insertion diagnostic for the nucleic acid molecule of the present invention and/or comprises the oligonucleotide as described above and/or is the pair of oligonucleotides or the kit as described above.

BRIEF DESCRIPTION OF THE DRAWINGS

FIG. 2 A-D: shows a CLUSTAL O (1.2.4) multiple sequence alignment of the RLK1 alleles HT2 (SEQ ID NO: 2), HTN1 (SEQ ID NO: 9), PH99N (SEQ ID NO: 11) and PH26N (SEQ ID NO: 13). Position with sequence differences are indicated by missing asterisk in the lowest line of each block.

FIGS. 3 A and B: shows a ClustalV (PAM250) multiple sequence alignment of RLK1 polypeptides: RLK1_A619HT2_CDS.seq (SEQ ID NO: 3), RLK1_A619HT3_CDS.seq (identical with SEQ ID NO: 3), RLK1_B37HTN_CDS.seq (SEQ ID NO: 10), RLK1_A619HT2_Exon1.seq (SEQ ID NO: 6), RLK1_A619HT2_Exon2.seq (SEQ ID NO: 7), and RLK1_A619HT2_Exon3.seq (SEQ ID NO: 8).

FIG. 4 A-C: shows sequence alignment of the cDNA of HT2 (SEQ ID NO: 2) and the cDNA of the RLK1 allele derived from genotype A188. At position 1458 to 1459 of the A188 allele a 2 bp insertion "AC" (white letters on black background) which causes an early stop codon (bold and underlined) has been identified.

FIG. 5: shows sequence alignment of amino acids of A619HT2 and modified A188 RLK1. Modified A188 RLK is 99.1% identical to A619HT2.

DETAILED DESCRIPTION OF THE INVENTION

Figure 1:
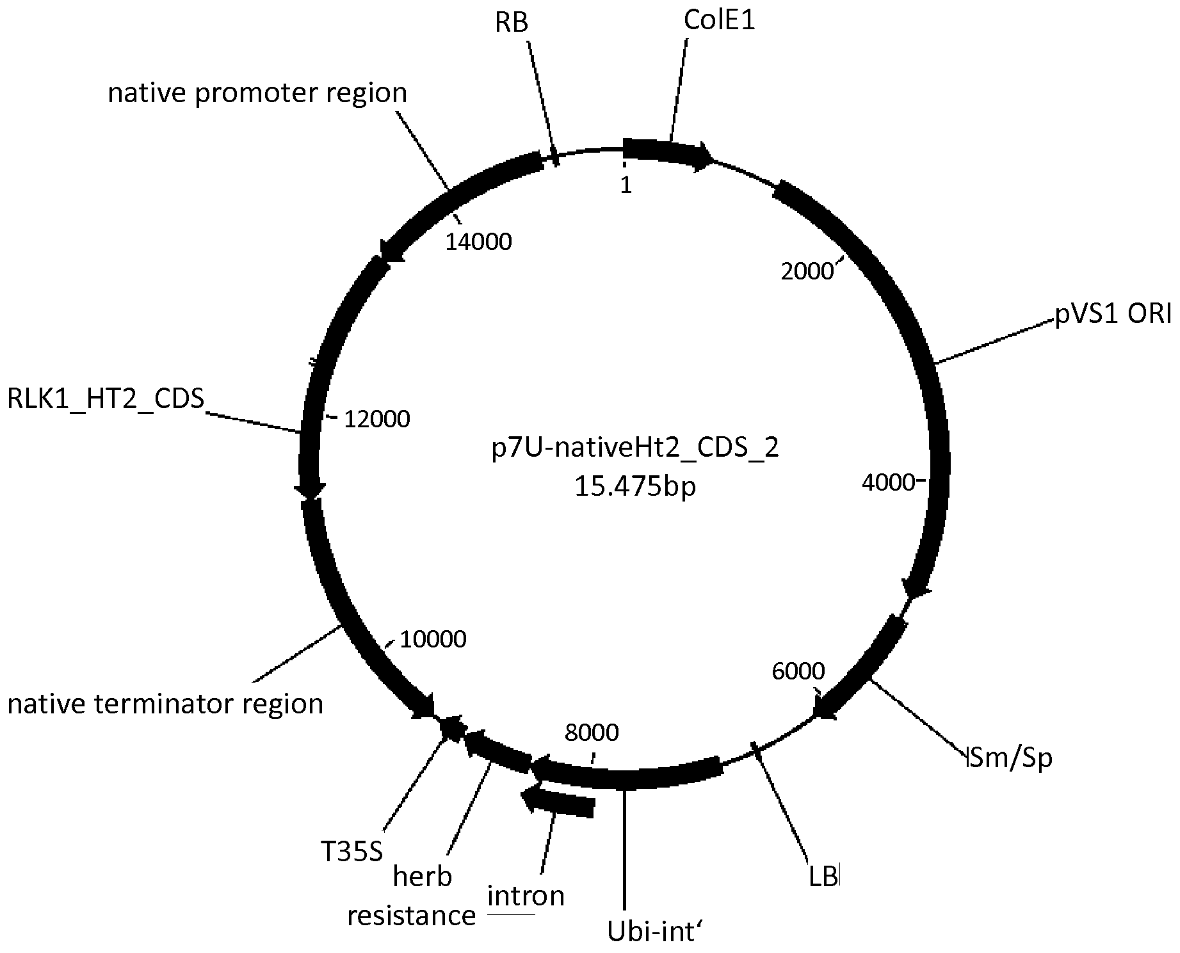
FIG. 1: shows vector p7U-nativeHT2_CDS_2 which can be used to transform *Zea mays* plants. The expression cassette containing the cDNA of HT2 gene (SEQ ID NO: 2) under control of the native promoter (SEQ ID NO: 4) and terminator (SEQ ID NO: 5) was transformed into a binary vector containing for instance a herbicide gene (e.g.: BASTA resistance, glyphosate resistance or ALS inhibitor resistance) for subsequent transformation into *Agrobacterium tumefaciens* for *Agrobacterium* mediated plant transformation into maize (*Zea mays*) genotype A188.

The present invention is based on the identification of the HT2 gene which encodes a polypeptide conferring (or increasing) resistance to a plant against a fungal pathogen, such as *Helminthosporium turcicum*.

Accordingly, in one aspect of the present invention, provided is a nucleic acid molecule comprising or consisting of a nucleotide sequence encoding said HT2 gene. In one embodiment, the nucleic acid molecule of the invention is comprising or consisting of a nucleotide sequence having the nucleotide sequence set forth in SEQ ID NO: 1 (genomic DNA of HT2) or SEQ ID NO: 2 (cDNA of HT2). Also provided is a nucleic acid molecule comprising or consisting of a nucleotide sequence encoding the amino acid sequence set forth in SEQ ID NO: 3 (HT2 protein).

Further provided is a nucleic acid molecule comprising or consisting of a nucleotide sequence having at least 96% identity to the nucleotide sequence set forth in SEQ ID NO: 1 or SEQ ID NO: 2, preferably over the full length. Preferably, the nucleotide sequence having at least 97%, 98%, 99% or 99.5% identity to the nucleotide sequence set forth in SEQ ID NO: 1 or SEQ ID NO: 2, preferably over the full length. Also provided is a nucleic acid molecule comprising or consisting of a nucleotide sequence encoding an amino acid sequence having at least 92% identity to the amino acid sequence set forth in SEQ ID NO: 2, preferably over the full length. Preferably, the nucleic acid molecule comprises or consists of a nucleotide sequence encoding an amino acid sequence having at least 93%, 94%, 95%, 96%, 97%, 98%, 99% or 99.5% identity to the amino acid sequence set forth in SEQ ID NO: 3, preferably over the full length.

In another embodiment, provided is a nucleic acid molecule comprising or consisting of a nucleotide sequence hybridizing with the complementary strand of the nucleotide sequence set forth in SEQ ID NO: 1 or SEQ ID NO: 2 or the nucleotide sequence encoding the amino acid sequence set forth in SEQ ID NO: 3 under stringent hybridization conditions.

Moreover, provided is a nucleic acid molecule comprising or consisting of a nucleotide sequence encoding a protein derived from the protein encoded by the nucleotide sequence of SEQ ID NO: 1 or SEQ ID NO: 2, or derived from the amino acid sequence set forth in SEQ ID NO: 3 by way of substitution, deletion and/or addition of one or more amino acid(s).

Deletion, substitution, or addition of amino acid(s) can be carried out by a technique known in the art. Mutagenesis in a nucleotide sequence can be caused by a known method such as the Kunkel method, the gapped duplex method, or a method similar to such a known method. For instance, mutagenesis can be caused with the use of a mutagenesis kit (e.g., Mutant-K or Mutant-G (product name, TAKARA Bio)) based on a site-directed mutagenesis method, an LA PCR in vitro Mutagenesis series kit (product name, TAKARA Bio), or the like. Alternatively, a mutagenesis method may be a method using a chemical mutagen represented by EMS (ethyl methanesulfonate), 5-bromouracil, 2-aminopurine, hydroxylamine, N-methyl-N'-nitro-N-nitrosoguanidine, or a different carcinogenic compound, a method comprising radiation treatment using radioactive rays such as X-rays, alpha-rays, beta-rays, gamma-rays, or an ion beam, or a method comprising ultraviolet treatment.

When an amino acid residue is altered, the amino acid is preferably mutated for a different amino acid(s) that conserves the properties of the amino acid. Examples of amino acid properties are: hydrophobic amino acids (A, I, L, M, F, P, W, Y, and V), hydrophilic amino acids (R, D, N, C, E, Q, G, H, K, S, and T), amino acids containing aliphatic side chains (G, A, V, L, I, and P), amino acids containing hydroxyl group-containing side chains (S, T, and Y), amino acids containing sulfur-containing side chains (C and M), amino acids containing carboxylic acid- and amide-containing side chains (D, N, E, and Q), amino acids containing basic side chains (R, K, and H), and amino acids containing aromatic side chains (H, F, Y, and W) (amino acids are represented by one-letter codes in parentheses). Amino acid substitutions within each group are called conservative substitutions. Conservative substitutions are preferred.

Preferably, the nucleic acid molecule of the invention is encoding a polypeptide capable of conferring (or increasing) resistance to a plant disease caused by a fungal pathogen in a plant in which the polypeptide is expressed.

Additionally, the nucleic acid molecule of the invention is encoding a polypeptide which may not be capable of conferring resistance to a plant disease caused by *Helminthosporium turcicum* races 2 and/or 3 in a plant, preferably a plant of the species *Zea mays*, in which the polypeptide is expressed. The plant may show a susceptible response to infection with *Helminthosporium turcicum* races 2 and/or 3.

A further example of the nucleic acid molecule of the invention may be a nucleic acid molecule comprises or consists of the nucleotide sequence set forth in SEQ ID NO: 23, or a nucleic acid molecule comprising or consisting of a nucleotide sequence encoding the amino acid sequence set forth in SEQ ID NO: 24.

In one embodiment, the fungal pathogen belongs to the division of Ascomycota or Basidiomycota. The fungal pathogen may belong to family Pleosporaceae, Pucciniaceae or Botryosphaeriaceae. Preferably, the fungal pathogen belongs to the genus of *Setosphaeria, Bipolaris, Puccinia* or *Diplodia*, more preferably is the species of *Helminthosporium turcicum, Setosphaeria rostrata, Setosphaeria glycinea, Setosphaeria holmii, Setosphaeria khartoumensis, Setosphaeria minor, Setosphaeria monoceras, Setosphaeria pedicellata, Setosphaeria prolata, Bipolaris australis, Bipolaris brizae, Bipolaris buchloës, Bipolaris cactivora, Bipolaris clavata, Bipolaris coicis, Bipolaris colocasiae, Bipolaris crotonis, Bipolaris crustacean, Bipolaris cylindrical, Bipolaris euchlaenae, Bipolaris halepensis, Bipolaris heveae, Bipolaris incurvata, Bipolaris indica, Bipolaris iridis, Bipolaris Ieersiae, Bipolaris micropus, Bipolaris miyakei, Bipolaris multiformis, Bipolaris nicotiae, Bipolaris novaezelandiae, Bipolaris ovariicola, Bipolaris panici-miliacei, Bipolaris papendorfii, Bipolaris sacchari, Bipolaris sakadehensis, Bipolaris sorghicola, Bipolaris subpapendorfii, Bipolaris tropicalis, Bipolaris urochloae, Bipolaris zeae, Puccinia asparagi, Puccinia graminis, Puccinia horiana, Puccinia mariae-wilsoniae, Puccinia poarum, Puccinia psidii, Puccinia recondite, Puccinia sessilis, Puccinia sorghi, Puccinia striiformis, Puccinia triticina, Diplodia maydis, Diplodia seriata* or *Stenocarpella* (*Diplodia*) *macrospora*, most preferably is *Helminthosporium turcicum, Puccinia sorghi, Diplodia macrospora* or *Bipolaris maydis.*

In one embodiment, the plant disease is a fungal disease. In a preferred embodiment, the plant disease is selected from the group consisting of Northern Corn Leaf Blight (caused by *Helminthosporium turcicum*), Southern Corn Leaf Blight (caused by *Bipolaris maydis*), Common Rust (caused by *Puccinia sorghi*), and *Diplodia* Leaf Streak (caused by *Diplodia macrospora*, also called *Stenocarpella macrospora*). Most preferably, the plant disease is Northern Corn Leaf Blight (NCLB).

In a preferred embodiment, the nucleic acid molecule of the invention is encoding a polypeptide capable of conferring to a plant (or increasing in a plant) resistance against Northern Corn Leave Blight (NCLB), i.e. resistance against *Helminthosporium turcicum*, in particular resistance against *Helminthosporium turcicum* races 0, 1, 2, 3, N, 12, 23, 2N, 12N, 23N and/or 123N, or resistance against *Helminthosporium turcicum* races 0, 1 and/or N.

In one embodiment, the plant according to the invention is *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Triticum durum, Secale cereale, Triticale,*

*Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Helianthus annuus, Helianthus tuberosus* and *Allium tuberosum*, or any variety or subspecies belonging to one of the aforementioned plants, more preferably *Hordeum vulgare, Hordeum bulbusom, Sorghum bicolor, Zea mays, Setaria italica, Oryza minuta, Oriza sativa, Oryza australiensis, Oryza alta, Triticum aestivum, Triticum durum, Secale cereale, Triticale, Hordeum marinum, Aegilops tauschii*, or any variety or subspecies belonging to one of the aforementioned plants, or most preferably *Hordeum vulgare, Sorghum bicolor, Zea mays, Triticum aestivum, Secale cereale*, or any variety or subspecies belonging to one of the aforementioned plants.

In a preferred embodiment, the plant according to the invention is *Zea mays*.

Preferably, the nucleic acid molecule according to the present invention encodes a polypeptide which is a wall associated receptor-like kinases 1 (WAK RLK1) or functionally belongs to the family of wall associated receptor-like kinases 1.

In another aspect, provided is a vector comprising the nucleic acid molecule of the present invention. The vector may be a plasmid, a cosmid, a phage or an expression vector, a transformation vector, shuttle vector or cloning vector, it may be double or single stranded, linear or circular, or it may be a prokaryotic or eukaryotic host, either by integration into its genome or transforming extrachromosomally.

Also provided is an expression cassette comprising the nucleic acid molecule of the invention.

In one embodiment, in the vector or expression cassette, the nucleotide sequence of the invention is operably linked to regulatory element allowing expression of the nucleotide sequence in a plant cell. The plant cell may be infectable by a fungal pathogen or infected by a fungal pathogen. In a preferred embodiment, the plant cell is located in a leaf or a leaf tissue. The regulatory element may be a promoter (native, synthetic, core promoter or chimeric promoter), a terminator, an enhancer or a cis-acting element. Furthermore, the regulatory element may be heterologous to the nucleotide sequence operably linked to regulatory element.

Preferably, the nucleotide sequence of the invention is operably linked in an expression vector to one or more regulatory sequences which allow transcription and optionally expression in a prokaryotic or eukaryotic host cell. As an example, the nucleotide sequence may be under the control of a suitable promoter or a terminator. Suitable promoters may be promoters which are constitutively induced (see, for example, the 35S promoter from the "cauliflower mosaic virus" (Odell J T, Nagy F, Chua N-H (1985) "Identification of DNA sequences required for activity of the cauliflower mosaic virus 35S promoter." Nature 313, 810-812 1985); other examples are the Actin promoter of *Oryza sativa* (SEQ ID NO: 43) or the EF1 promoter of *Brachypodium distachyon* (SEQ ID NO: 44). Particularly suitable promoters are those promoters which are pathogen-inducible (see, for example, the PR1 promoter from parsley (Rushton P J, Torres J T, Parniske M, Wernert P, Hahlbrock K und Somssich I E (1996) Interaction of elicitor-induced DNA-binding proteins with elicitor response elements in the promoters of parsley PR1 genes. EMBO J. 15(20): 5690-5700). Particularly suitable pathogen-inducible promoters are synthetic or chimeric promoters which do not occur in nature, are composed of several elements and contain a minimum promoter as well as, upstream of the minimum promoter, at least one cis-regulatory element which act as the binding site for special transcription factors. Chimeric promoters are custom-designed and are induced by various factors or re-primed. Examples of such promoters can be found in WO2000/29592 and WO2007/147395. An example of a suitable terminator is the nos-terminator (Depicker A, Stachel S, Dhaese P, Zambryski P, Goodman H M (1982) Nopaline synthase: transcript mapping and DNA sequence. J Mol Appl Genet. 1(6): 561-73).

Further provided is a host cell comprising the nucleic acid molecule of the invention, or the vector of the invention, or the expression cassette of the invention.

The vector or the expression cassette may, for example, be introduced into the host cell by conjugation, mobilization, biolistic transformation, *agrobacterium*-conferred transformation, transfection, transduction, vacuum infiltration or electroporation. Methods of this type as well as methods for the preparation of the vectors described are familiar to the person skilled in the art (Sambrook et al., Molecular Cloning, Cold Spring Harbor Laboratory, 3rd Ed., 2001).

In one embodiment, the host cell may be a prokaryotic cell (for example, a bacterial cell). In another embodiment, the host cell may be a eukaryotic cell (for example, a plant cell or a yeast cell). Particularly preferred bacterial host cells are *Agrobacterium tumefaciens, A. rhizogenes*, and *E. coli.*

In another aspect, provided is a protein encoded by the nucleic acid molecule of the invention.

In yet another aspect, provided is a plant comprising the nucleic acid molecule of the invention, the vector of the invention, the expression cassette of the invention, or the protein of the invention. The plant may be a transgenic plant or a genetically edited plant. A part of the plant of the invention, plant cell of the plant of the invention and seed of the plant of the invention is also provided, wherein the seed comprising the nucleic acid molecule of the invention transgenically or endogenously, the vector of the invention, the expression cassette of the invention, or the polypeptide of the invention.

Figure 6:
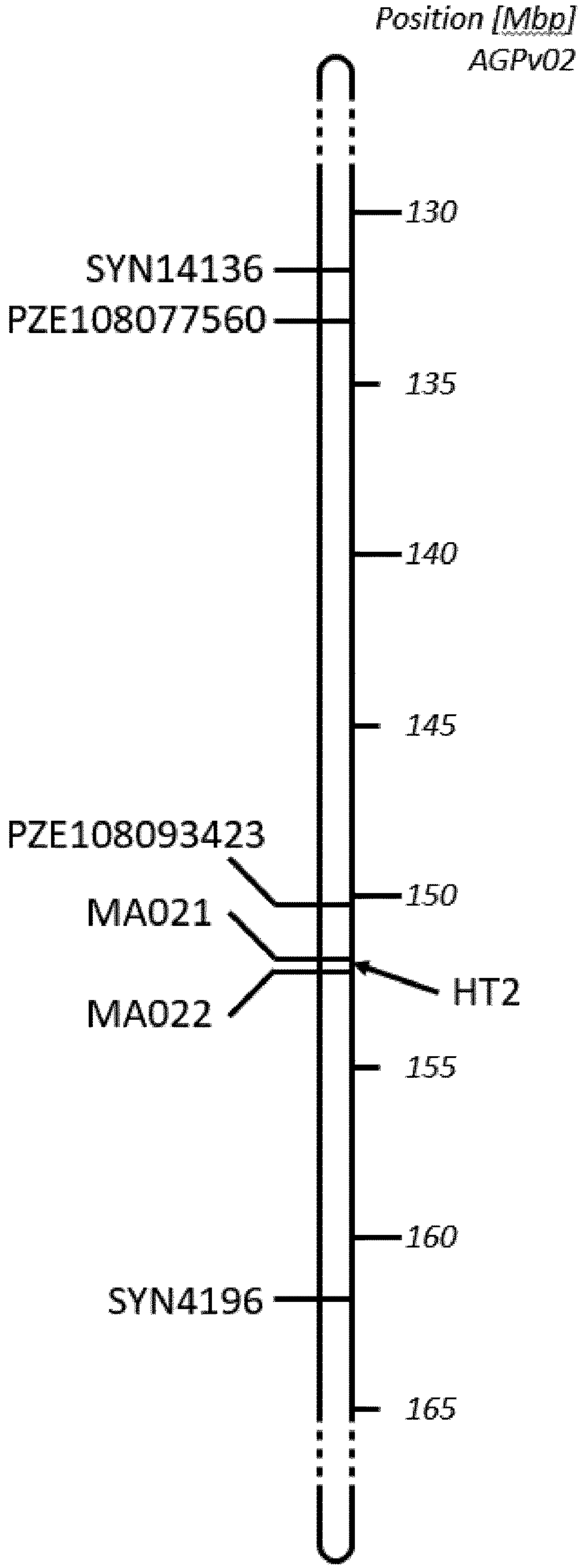
FIG. 6: shows a map of marker positions with reference to the marker positions of AGPv02.

From WO2015/032494 which investigated and used introgression lines with Htn1 from Pepitilla, it is known that this restance locus is closely linked to genomic regions carrying linkage drag resulting in negative effects on one or more agronomic features. First investigation of the flanking region of HT2 indicated that this or similar linkage drag is not only present in Pepitilla donor for HtN1 introgression, but also in other donors for this *Helminthosporium* resistance locus like A619. Inter alia the linkage drag as part of the HT2 introgression can effect a difference in the flowering time, which is an important agronomic characteristic. It can directly and substantially influence the yield potential of a *Zea mays* plant. A delayed flowering time usually results in a reduced yield. Further linkage drag affecting the yield potential, in particular the silage yield potential, may be found distal and/or proximal of the *Helminthosporium* resistance locus on bin 8.06 in *Zea mays*. Flanking regions, closely linked to this resistance locus, might be carrier of the known linkage drag, however, these regions can be limited to an interval located between alleles of marker SYN14136 and marker MA0021 and/or an interval located between alleles of marker MA0022 and marker SYN4196 (FIG. 6). Thus, the plant of the invention may be a plant of the species *Zea mays* comprising the nucleic acid molecule of the invention endogenously, wherein the flanking regions in the genome does not contain an A619HT2 or A619HT3 derived interval located between alleles of marker SYN14136 and marker MA0021 or an A619HT2 or A619HT3 derived interval located between alleles of marker MA0022 and marker SYN4196. In a preferred embodiment, the plant is a plant of the species *Zea mays* comprising the nucleic acid molecule of the invention endogenously, wherein the flanking regions in the genome does not contain an A619HT2 or A619HT3 derived interval located between alleles of marker SYN14136 and marker PZE108077560, an A619HT2 or A619HT3 derived interval located between alleles of marker PZE108093423 and marker MA0021, or an A619HT2 or A619HT3 derived interval located between alleles of marker MA0022 and marker SYN4196.

TABLE 2

KASP marker primer sequences and assignment to donor alleles (allele X and allele Y: describe the biallelic values of the SNPs)

| SNP marker | Marker position AGPv02 [bp] | Primer alleles X(5'-3') [SEQ ID NO] | Primer alleles Y(5'-3') [SEQ ID NO] | Common primer (5'-3') [SEQ ID NO] | A619HT2 donor alleles (SNP) |
|---|---|---|---|---|---|
| SYN14136 | 131681497 | 25 | 26 | 27 | A |
| PZE-108077560 | 133189880 | 28 | 29 | 30 | A |
| PZE-108093423 | 150279048 | 31 | 32 | 33 | A |
| MA0021 | 151907173 | 34 | 35 | 36 | G |
| MA0022 | 152046529 | 37 | 38 | 39 | A |
| SYN4196 | 161766769 | 40 | 41 | 42 | C |

As an example, removal of linkage drag may be carried out by genetic recombination during a crossing process between two maize plants, wherein one parent maize plant carries the HT2-resistance locus. In addition to the use of conventional breeding techniques to produce a genetic recombination which has the result of replacing at least one of the donor intervals with linkage drag identified above with genomic sequences of the recurrent parent which are preferably free from unwanted genes, modern biotechnology offers the person skilled in the art many tools which can enable precise genetic engineering to be carried out. Examples of known tools are meganucleases (Silva et al., 2011), homing endonucleases (Chevalier 2002), zinc finger nucleases, TALE nucleases (WO 2010/079430; WO 2011/072246) or CRISPR systems (Gaj et al., 2013). These are artificial nuclease fusion proteins which are capable of cleaving double stranded nucleic acid molecules such as plant DNA and thus of producing double strand breaks at desired positions in the genome. By exploiting the cells own mechanisms for repairing induced double strand breaks, a homologous recombination or a "non-homologous end joining" can be carried out, which could lead to the removal of the intervals of the donor carrying linkage drag. Suitable target sequences in the genome for the recognition domain nucleases may be taken, for example, from the sequence information of the SNP markers (Table 2). However, a person skilled in the art is also able to identify other sequences, preferably within the defined flanking regions described above, which are suitable as target sequences for the recognition domains of the nucleases.

In another aspect, provided is a genetically edited or transgenic plant comprising the nucleic acid molecule of the invention, the vector of the invention or the expression cassette of the invention. The nucleic acid molecule may be a transgene or a modified/edited endogenous gene. A promoter may be operably linked to the nucleic acid molecule or nucleotide sequence for expression.

Also provided is a part or seed of the plant of the invention comprising the nucleic acid molecule of the invention, the vector of the invention or the expression cassette of the invention, wherein the seed comprises the nucleic acid molecule of the invention, the vector of the invention, the expression cassette of the invention. The nucleic acid molecule may be a transgene or a modified/edited endogenous gene.

According to another aspect, provided a method of identifying or selecting a plant, preferably a plant of the species *Zea mays*, having increased resistance to a plant disease caused by fungal pathogen, preferably by *Helminthosporium turcicum*, more preferably by *Helminthosporium turcicum* races 0, 1 and/or N, or a part, a cell or a seed thereof, comprising the following steps: (a) detecting in the plant, or part, cell or seed thereof (or in a sample of the plant, or part, cell or seed thereof), the presence of the nucleic acid molecule of the present invention as described above or a nucleotide sequence selected from the group consisting of: (i) a nucleotide sequence having at least 60%, 65%, 70%, 75%, 80%, 85%, 90%, 92%, 94%, 96%, 98%, 99% or 99.5% identity to the nucleotide sequence set forth in SEQ ID NO: 1 or SEQ ID NO: 2, preferably over the full length, (ii) a nucleotide sequence encoding an amino acid sequence having at least 60%, 65%, 70%, 75%, 80%, 85%, 90%, 92%, 94%, 96%, 98%, 99% or 99.5% identity to the amino acid sequence set forth in SEQ ID NO: 3, preferably over the full length, (iii) a nucleotide sequence having at least 85%, 90%, 92%, 94%, 96%, 98%, 99% or 99.5% identity to nucleotide positions 1-920 of the nucleotide sequence set forth in SEQ ID NO: 1 or SEQ ID NO: 2 (Exon 1; SEQ ID NO: 6), preferably over the full length, and/or having at least 60%, 65%, 70%, 75%, 80%, 85%, 90%, 92%, 94%, 96%, 98%, 99% or 99.5% identity to nucleotide positions 23252-23288 of the nucleotide sequence set forth in SEQ ID NO: 1 (Exon 2; SEQ ID NO: 7) or to nucleotide positions 921-957 of the nucleotide sequence set forth in SEQ ID NO: 2 (Exon 2; SEQ ID NO: 7), preferably over the full length, and/or having at least 98%, 98.5%, 99% or 99.5% identity to nucleotide positions 23586-24632 of the nucleotide sequence set forth in SEQ ID NO: 1 (Exon 3; SEQ ID NO: 8) or to nucleotide positions 958-2004 of the nucleotide sequence set forth in SEQ ID NO: 2 (Exon 3; SEQ ID NO: 8), preferably over the full length, (iv) a nucleotide sequence encoding an amino acid sequence having at least 75%, 80%, 85%, 90%, 92%, 94%, 96%, 98%, 99% or 99.5% identity to the positions 1-306 of amino acid sequence set forth in SEQ ID NO: 3, preferably over the full length, and/or having at least 60%, 65%, 70%, 75%, 80%, 85%, 90%, 92%, 94%, 96%, 98%, 99% or 99.5% identity to positions 307-319 of amino acid sequence set forth in SEQ ID NO: 3, preferably over the full length, and/or having at least 98%, 98.5%, 99% or 99.5% identity to positions 320-668 of amino acid sequence set forth in SEQ ID NO: 3, preferably over the full length, wherein the nucleic acid molecule of any one of (i) to (iv) is encoding a polypeptide capable of conferring or increasing resistance to a plant disease caused by fungal pathogen, preferably by *Helminthosporium turcicum*, more preferably by *Helminthosporium turcicum* races 0, 1 and/or N, in a plant, preferably a plant of the species *Zea mays*, in which the polypeptide is expressed, and wherein preferably the nucleic acid molecule of any one of (i) to (iv) encodes a polypeptide which is or belongs functionally to the family of wall associated receptor-like kinases 1 (WAK RLK1); or detecting in the plant, or part, cell or seed thereof (or in a sample of the plant, or part, cell or seed thereof), the presence of polypeptide encoded by the nucleic acid molecule of the present invention as described above or a nucleotide sequence of any one of (i) to (iv), and (b) identifying or selecting the plant in which or in whose part, cell or seed the nucleic acid molecule as defined in (a) is present, as having a resistance or an increased resistance to a plant disease caused by a fungal pathogen, preferably by *Helminthosporium turcicum*, more preferably by *Helmint-hosporium turcicum* races 0, 1 and/or N.

The method may comprise the additional step of obtaining a nucleic acid sample from the plant or part, cell or seed and detecting the sequence in the sample. For example, the step of obtaining the nucleic acid sample from the plant, or part or seed thereof, may be carried out prior to the detection step (a).

The detection of a nucleotide sequence may be carried out by a hybridization method, using an oligonucleotide probe. The conditions of hybridization can appropriately be selected depending on factors such as the Tm value of the probe used and the CG content of the target DNA. Known hybridization methods are described, for example, in Sambrook et al., 2001.

Alternatively, the detection of a gene may be carried out by means of a DNA amplification method, such as PCR, using respective primers. When the detection is carried out by PCR method, PCR conditions can appropriately be selected depending on the factors such as the Tm value of the primer used and the length of the amplified region to be detected. The detection can be carried out by amplifying the target by PCR and confirming the presence or absence of a PCR-amplified product. The method for confirming the presence or absence of an amplification product is not particularly limited. For example, the amplification product can be confirmed by subjecting a reaction mixture of nucleic acid amplification to agarose gel electrophoresis; thereafter, staining the gel with an appropriate nucleic acid staining reagent such as ethidium bromide, SYBER Green I or the like; and detecting the presence or absence of the bands resulting from irradiation with ultraviolet rays. The bands may be detected by visual observation, or they may be detected by using, for example, a fluorescent image analyzer, or the like.

Further provided is, a method or process of identifying a plant, preferably a plant of the species *Zea mays*, having increased resistance to a plant disease caused by fungal pathogen, *Helminthosporium turcicum*, more preferably by *Helminthosporium turcicum* races 0, 1 and/or N, or a part, having increased resistance to a plant disease caused by *Helminthosporium turcicum*, preferably by *Helminthosporium turcicum* races 0, 1 and/or N and comprises the nucleic acid molecule of the invention endogenously, a cell or a seed thereof, the method or process comprising detecting in the plant alleles of at least two markers, wherein at least one of said markers is on or within the chromosomal interval between SYN14136 and the nucleic acid molecule of the invention, and at least one of said markers is on or within the chromosomal interval between the nucleic acid molecule of the invention and SYN4196. In a preferred embodiment, the method or process comprising detecting in the plant alleles of at least two markers, wherein at least one of said markers is on or within the chromosomal interval between PZE108093423 and the nucleic acid molecule of the invention, and at least one of said markers is on or within the chromosomal interval between the nucleic acid molecule of the invention and SYN4196.

In another aspect, provided is a method of identifying an allele of a resistance gene conferring or increasing resistance to a plant disease caused by a fungal pathogen, preferably by *Helminthosporium turcicum*, more preferably by *Helmint-hosporium turcicum* races 0, 1, 2, 3, N, 12, 23, 2N, 12N, 23N and/or 123N, in *Zea mays* and preferably encoding a polypeptide which is or belongs functionally to the family of wall associated receptor-like kinases 1 (WAK RLK1), wherein the method comprises the following steps: (a) conducting sequence comparison using (i) at least one coding nucleotide sequence isolated from a *Zea mays* genotype, wherein the nucleotide sequence preferably maps to bin 8.05 resistance locus or to bin 8.06 resistance locus, and (ii) as reference sequence, a nucleotide sequence of the invention, preferably the nucleotide sequence set forth in SEQ ID NO: 1 or SEQ ID NO: 2 or the nucleotide sequence encoding the amino acid sequence set forth in SEQ ID NO: 3, or a part thereof, or a consensus sequence derived from a set of at least two nucleotide sequences wherein one nucleotide sequence is the nucleotide sequence of the invention, preferably the nucleotide sequence set forth in SEQ ID NO: 1 or SEQ ID NO: 2 or the nucleotide sequence encoding the amino acid sequence set forth in SEQ ID NO: 3, or a part thereof, and wherein each nucleotide sequence of the set of at least two nucleotide sequences encodes a polypeptide capable of conferring or increasing resistance to a plant disease caused by fungal pathogen, preferably by *Helminthosporium turcicum*, more preferably by *Helminthosporium turcicum* races 0, 1 and/or N, in *Zea mays* in which the polypeptide is expressed, and preferably maps to bin 8.05 resistance locus or to bin 8.06 resistance locus and preferably encoding a polypeptide which is or belongs functionally to the family of wall associated receptor-like kinases 1 (WAK RLK1); and (b) identifying the allele, if the sequence comparison reveals (i) a sequence identity on nucleotide level of at least 85%, 90%, 92%, 94%, 96%, 98%, 99% or 99.5% identity to nucleotide positions 1-920 of the nucleotide sequence set forth in SEQ ID NO: 1 or SEQ ID NO: 2, preferably over the full length, and/or of at least 60%, 65%, 70%, 75%, 80%, 85%, 90%, 92%, 94%, 96%, 98%, 99% or 99.5% identity to nucleotide positions 23252-23288 of the nucleotide sequence set forth in SEQ ID NO: 1 or to nucleotide positions 921-957 of the nucleotide sequence set forth in SEQ ID NO: 2, preferably over the full length, and/or of at least 98%, 98.5%, 99% or 99.5% identity to nucleotide positions 23586-24632 of the nucleotide sequence set forth in SEQ ID NO: 1 or to nucleotide positions 958-2004 of the nucleotide sequence set forth in SEQ ID NO: 2, preferably over the full length, and/or (ii) a sequence identity of encoded amino acid level of at least 75%, 80%, 85%, 90%, 92%, 94%, 96%, 98%, 99% or 99.5% identity to the positions 1-306 of amino acid sequence set forth in SEQ ID NO: 3, preferably over the full length, and/or of at least 60%, 65%, 70%, 75%, 80%, 85%, 90%, 92%, 94%, 96%, 98%, 99% or 99.5% identity to positions 307-319 of amino acid sequence set forth in SEQ ID NO: 3, preferably over the full length, and/or of at least 98%, 98.5%, 99% or 99.5% identity to positions 320-668 of amino acid sequence set forth in SEQ ID NO: 3, preferably over the full length.

Preferably, the consensus sequence is derived from a set of at least two nucleotide sequences wherein one nucleotide sequence is the nucleotide sequence of the invention, preferably the nucleotide sequence set forth in SEQ ID NO: 1 or SEQ ID NO: 2 or the nucleotide sequence encoding the amino acid sequence set forth in SEQ ID NO: 3, or a part thereof, and wherein a further nucleotide sequence is selected from the group consisting of the nucleotide sequence set forth in SEQ ID NO: 9 or a part thereof, the nucleotide sequence set forth in SEQ ID NO: 11 or a part thereof, the nucleotide sequence set forth in SEQ ID NO: 13 or a part thereof, the nucleotide sequence set forth in SEQ ID NO: 23 or a part thereof, a nucleotide sequence encoding the amino acid sequence set forth in SEQ ID NO: 10 or a part thereof, a nucleotide sequence encoding the amino acid sequence set forth in SEQ ID NO: 12 or a part thereof, a nucleotide sequence encoding the amino acid sequence set forth in SEQ ID NO: 14 or a part thereof, or a nucleotide sequence encoding the amino acid sequence set forth in SEQ ID NO: 24 or a part thereof.

The at least one coding nucleotide sequence isolated from a *Zea mays* genotype of step (a) (i) can be derived from a plant sequence database or from a gene bank where seed samples of various *Zea mays* genotype are deposited. Plant sequence databases or gene banks are known in the art.

The method of identifying a (new) allele of a resistance gene (or a potential new allele of a resistance gene) conferring resistance or increased resistance to a plant disease caused by a fungal pathogen may further comprise, e.g. as step (c), the step of determining the resistance level of the plant against the fungal pathogen caused by the identified allele.

A nucleic acid molecule comprising or consisting of a nucleotide sequence encoding an allele of a resistance gene (or potential new allele) identified by the method of identifying described above is also provided. Said allele may be used in a method of producing a plant, preferably a plant of the species *Zea mays*, or in a method for conferring/increasing resistance to a plant disease which is caused by a fungal pathogen such as *Helminthosporium turcicum*, preferably by *Helminthosporium turcicum* races 0, 1, 2, 3, N, 12, 23, 2N, 12N, 23N and/or 123N. In one embodiment, the method according to the invention of producing a plant or the method according to the invention for conferring/increasing resistance to a plant disease further comprises in step (a) the introduction of at least one nucleic acid molecule comprising or consisting of a nucleotide sequence encoding the new resistance gene into the at least one cell of the plant.

In another aspect, provided is a method for conferring or increasing resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, in a plant, preferably a plant of the species *Zea mays*, comprising the following steps: (a) introducing into at least one cell of the plant the nucleic acid molecule of the present invention, including for example a nucleic acid molecule comprising or consisting of a nucleotide sequence of the identified allele, the expression cassette of the invention or the vector of the invention, (b) regenerating the plant from the at least one cell, and (c) causing expression of the nucleic acid molecule in the plant.

In a preferred embodiment of the method for conferring or increasing resistance to a plant disease caused by a fungal pathogen, step (a) results in the modification of an endogenous nucleic acid molecule conferring susceptibility to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, preferably mapping to bin 8.05 resistance locus or to bin 8.06 resistance locus on chromosome 8 of *Zea mays*, and preferably encoding a polypeptide which is or belongs functionally to the family of wall associated receptor-like kinases 1 (WAK RLK1), wherein the modification converts the endogenous nucleic acid molecule into the nucleic acid molecule of the present invention conferring resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, if expressed.

In another preferred embodiment of the method for conferring or increasing resistance to a plant disease caused by a fungal pathogen, step (a) results in the modification of an endogenous nucleic acid molecule conferring resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, preferably mapping to bin 8.05 resistance locus or to bin 8.06 resistance locus on chromosome 8 of *Zea mays*, and preferably encoding a polypeptide which is or belongs functionally to the family of wall associated receptor-like kinases 1 (WAK RLK1), wherein the modification converts the endogenous nucleic acid molecule into the nucleic acid molecule of the present invention conferring increased resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, if expressed.

Further provided is a method for increasing resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, in a plant of the invention, comprising the steps of reducing the level of expression of the nucleic acid molecule of the present invention, including for example a nucleic acid molecule comprising or consisting of a nucleotide sequence of the identified allele, the expression cassette of the invention or the vector of the invention, in the plant or at least one cell of the plant, preferably compared to the expression level of the endogenous gene in a resistant wild type plant. Such resistant wild type plant is for instances selected from the lines A619HT2, B37HT2 or B73HT2. Reducing can be conducted transiently or durably, preferably as preventive measure if infestation by the fungal pathogen in expected e.g. due to particular environmental conditions which drives the distribution of the fungal pathogen. A person skilled in the art is knowing very well various methodologies to reduce the expression of gene in plant. Durable reduction of expression level can be achieved e.g. by modulating the promoter or other regulatory elements by means of random or targeted mutagenesis or by stable integration of an expression cassette allowing the expression of double-stranded RNA, single-stranded antisense RNA or a hairpin DNA, which are able to silence as interfering RNA the mRNA encoded by the nucleic acid molecule of the invention. Such inhibitory RNA molecule, preferably in form of siRNA molecules, can also be used for transient reduction of the level of expression if applied to the plants as spray and taken up actively or passively by the plant cells, preferably cells of leaves.

In another aspect, provided is a method for producing a plant (or part, cell or seed thereof), preferably a plant of the species *Zea mays*, having (increased) resistance to a plant disease caused by fungal pathogen, preferably by *Helminthosporium turcicum*, more preferably by *Helminthosporium turcicum* races 0, 1, 2, 3, N, 12, 23, 2N, 12N, 23N and/or 123N, or a part, a cell or a seed thereof, comprising the following steps: (a) introducing into the plant or at least one cell of the plant the nucleic acid molecule of the present invention, including for example a nucleic acid molecule comprising or consisting of a nucleotide sequence of the identified allele, the expression cassette of the invention or the vector of the invention, (b) optionally, regenerating the plant from the at least one cell, and (c) causing expression of the nucleic acid molecule in the plant or part thereof.

In a preferred embodiment of the method for producing a plant (or part, cell or seed thereof) of the species *Zea mays*, step (a) results in the modification of an endogenous nucleic acid molecule conferring susceptibility to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, preferably mapping to bin 8.05 resistance locus or to bin 8.06 resistance locus on chromosome 8 of *Zea mays*, and preferably encoding a polypeptide which is or belongs functionally to the family of wall associated receptor-like kinases 1 (WAK RLK1), wherein the modification converts the endogenous nucleic acid molecule into the nucleic acid molecule of the present invention conferring resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, if expressed.

In another preferred embodiment of the method for producing a plant (or part, cell or seed thereof) of the species *Zea mays*, step (a) results in the modification of an endogenous nucleic acid molecule conferring resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, preferably mapping to bin 8.05 resistance locus or to bin 8.06 resistance locus on chromosome 8 of *Zea mays*, and preferably encoding a polypeptide which is or belongs functionally to the family of wall associated receptor-like kinases 1 (WAK RLK1), wherein the modification converts the endogenous nucleic acid molecule into the nucleic acid molecule of the present invention conferring increased resistance to a plant disease caused by a fungal pathogen, preferably by *Helminthosporium turcicum*, more preferably by *Helminthosporium turcicum* races 0, 1, 2, 3, N, 12, 23, 2N, 12N, 23N and/or 123N, if expressed.

Preferably, the method is for producing a plant (or part, cell or seed thereof) having increased resistance to a plant disease caused by fungal pathogen, such as *Helminthosporium turcicum*, preferably by *Helminthosporium turcicum* races 0, 1, 2, 3, N, 12, 23, 2N, 12N, 23N and/or 123N. Accordingly, the method may comprise the additional step (d) of selecting a plant that has increased resistance compared to a reference plant.

Preferably, the reference plant is a plant of the same species, more preferably the reference plant is a wild-type plant of the same species or a plant isogenic to the plant selected in step (d), expect for the nucleic acid molecule of the present invention that has introduced in step (a) or modified during step (a) as described above.

Preferably, in the methods of the invention, the nucleic acid molecule of the invention is expressed in the plant or part thereof in an amount and/or period sufficient to increase or confer resistance to a plant disease caused by a fungal pathogen in the plant.

In another aspect, provided is a plant produced by the methods of the invention, or progeny, fruit, or seed thereof. Preferably, the plant or progeny, fruit, or seed thereof comprises the nucleic acid molecule of the invention, or the vector of the invention, or the protein of the invention, and/or the cell of the invention.

In another aspect, provided is the use of at least one nucleic acid molecule of the invention, including for example a nucleic acid molecule comprising or consisting of a nucleotide sequence of the identified new allele of a resistance gene, in the production of a plant having increased resistance to a plant disease caused by a fungal pathogen, preferably *Helminthosporium turcicum*, more preferably *Helminthosporium turcicum* races 0, 1, 2, 3, N, 12, 23, 2N, 12N, 23N and/or 123N. The plant produced may be a genetically edited or a transgenic plant.

Further provided is a method for controlling infestation of a fungal pathogen, preferably *Helminthosporium turcicum*, more preferably *Helminthosporium turcicum* races 0, 1, 2, 3, N, 12, 23, 2N, 12N, 23N and/or 123N, comprising the following steps: (a) growing plants of the present invention on agricultural and horticultural fields, and (b) causing expression of the nucleic acid molecule of the present invention, including for example a nucleic acid molecule comprising or consisting of a nucleotide sequence of the identified allele, the expression cassette of the invention or the vector of the invention, in the plants.

Another aspect of the invention is an oligonucleotide having a length of at least 15, 16, 17, 18, 19 or 20, preferably at least 21, 22, 23, 24 or 25, more preferred at least 30, 35, 40, 45, 50, 100, 200, 300 or 500 nucleotides, wherein the oligonucleotide is able to hybridize or anneal to (i) the nucleic acid molecule of the invention, (ii) the nucleic acid molecule comprising the nucleotide sequence of SEQ ID NO: 4 or SEQ ID NO: 5, or (iii) nucleic acid molecule complementary to (i) or (ii). Preferably, the oligonucleotide comprises a nucleotide sequence having an identity of at least 90%, 92%, 94%, 95%, 96%, 97%, 98%, 98.5%, 99%, 99.5% or 100% to the nucleotide sequence of the nucleic acid molecule of (i), (ii) or (iii) to which the oligonucleotide is able to hybridize or anneal.

Further provided is a pair of oligonucleotides or a kit comprising said oligonucleotides, wherein the oligonucleotides are suitable to anneal as forward primer and reverse primer to a region in the plant genome, preferably the *Zea mays* genome, which shows a cosegregation, preferably a perfect cosegregation, with the nucleic acid molecule of the invention. Preferably, the pair comprises one or two oligonucleotides of the invention.

Preferably, the kit comprises one, two or more oligonucleotides of the invention In a further aspect, provided is the use of at least one oligonucleotide as a molecular marker or part thereof in the method of identifying or selecting a plant, preferably a plant of the species *Zea mays*, having increased resistance to a plant disease caused by fungal pathogen, preferably by *Helminthosporium turcicum*, more preferably by *Helminthosporium turcicum* races 0, 1 and/or N, or a part, a cell or a seed thereof, or in the method of identifying an allele of a resistance gene conferring or increasing resistance to a plant disease caused by a fungal pathogen, preferably by *Helminthosporium turcicum*, more preferably by *Helminthosporium turcicum* races 0, 1 and/or N, in *Zea mays*, wherein the molecular marker is able to detect at least one single nucleotide polymorphism, deletion or insertion diagnostic for the nucleic acid molecule of the present invention and/or comprises the oligonucleotide as described above and/or is the pair of oligonucleotides or the kit as described above. Such single nucleotide polymorphism, deletion or insertion can be directly derived from the sequence alignment shown in FIG. 2. Preferably, the at least one single nucleotide polymorphism, deletion or insertion results in the exchange, deletion or insertion of at least one amino acid. Characteristic amino acid exchanges, deletion or insertions from a comparison between the polypeptide having the amino acid sequence set forth in SEQ ID NO: 3 and RLK1 polypeptide (SEQ ID NO: 10) conferring the "Pepitilla" resistance phenotype as disclosed in WO2015/032494 are shown in Table 2.

In another aspect, provided is a method for detecting the presence or absence of the nucleic acid molecule of the invention, including for example a nucleic acid molecule comprising or consisting of a nucleotide sequence of the identified allele, in a plant, preferably a plant of the species *Zea mays*, comprising the following steps: (a) isolating DNA from at least one cell of the plant, and (b) using a molecular marker to detect the presence or absence of the nucleic acid molecule of the invention, wherein the molecular marker is able to detect at least one single nucleotide polymorphism, deletion or insertion diagnostic for the nucleic acid molecule of the present invention and/or comprises the oligonucleotide as described above and/or is the pair of oligonucleotides or the kit as described above.

In one aspect, provided is the use of at least one or at least two oligonucleotide(s) as a molecular marker or part thereof in method or process of identifying a plant as described above in a method or process for the elimination of linkage drag close linked to the nucleic acid molecule of the invention for detecting the presence or absence of an A619HT2 or A619HT3 derived interval located between alleles of marker SYN14136 and marker MA0021 or an A619HT2 or A619HT3 derived interval located between alleles of marker MA0022 and marker SYN4196. In a preferred embodiment, at least one oligonucleotide is used as molecular marker or part thereof in a method or process for the elimination of linkage drag close linked to the nucleic acid molecule of the invention for detecting the presence or absence of an A619HT2 or A619HT3 derived interval located between alleles of marker SYN14136 and marker PZE108077560, an A619HT2 or A619HT3 derived interval located between alleles of marker PZE108093423 and marker MA0021, and/or an A619HT2 or A619HT3 derived interval located between alleles of marker MA0022 and marker SYN4196.

In another aspect, provided is a method for detecting the presence of the nucleic acid molecule of the invention, including for example a nucleic acid molecule comprising or consisting of a nucleotide sequence of the identified allele, in a plant, preferably a plant of the species *Zea mays*, comprising the following steps: (a) isolating DNA from at least one cell of the plant, and (b) using a molecular marker to detect the presence or absence of the nucleic acid molecule of the invention, wherein the molecular marker is able to detect at least one single nucleotide polymorphism, deletion or insertion diagnostic for the nucleic acid molecule of the present invention and/or comprises the oligonucleotide as described above and/or is the pair of oligonucleotides or the kit as described above. Such single nucleotide polymorphism, deletion or insertion can be directly derived from the sequence alignment shown in FIG. 2. Preferably, the at least one single nucleotide polymorphism, deletion or insertion results in the exchange, deletion or insertion of at least one amino acid. Characteristic amino acid exchanges, deletion or insertions from a comparison between the polypeptide having the amino acid sequence set forth in SEQ ID NO: 3 and RLK1 polypeptide conferring the "Pepitilla" resistance phenotype (SEQ ID NO: 10) as disclosed in WO2015/032494 are shown in Table 3.

TABLE 3

Characteristic amino acid exchanges, deletion or insertions from a comparison between the polypeptide having the amino acid sequence set forth in SEQ ID NO: 3 and RLK1 polypeptide (SEQ ID NO: 10) conferring the "Pepitilla" resistance phenotype as disclosed in WO2015/032494 (see also FIG. 3).

| Position | HTN | HT2 | effect | Exon |
|---|---|---|---|---|
| 5 | Q | L | strong | Exon 1 |
| 7 | H | R | weak | Exon 1 |
| 9 | S | P | weak | Exon 1 |
| 27 | G | A | weak | Exon 1 |
| 36 | N | S | weak | Exon 1 |
| 51 | A | V | strong | Exon 1 |
| 56 | | E | | Exon 1 |
| 75 | I | T | strong | Exon 1 |
| 95 | E | K | weak | Exon 1 |
| 101 | S | P | weak | Exon 1 |
| 102 | P | T | weak | Exon 1 |
| 114 | G | D | strong | Exon 1 |
| 115 | D | N | weak | Exon 1 |
| 122 | S | | | Exon 1 |
| 123 | Y | | | Exon 1 |
| 127 | Q | Y | weak | Exon 1 |
| 128 | Q | H | moderate | Exon 1 |
| 135 | R | S | moderate | Exon 1 |
| 142 | G | E | strong | Exon 1 |
| 147 | R | H | moderate | Exon 1 |
| 157 | L | | | Exon 1 |
| 158 | H | | | Exon 1 |
| 162 | A | P | moderate | Exon 1 |
| 180 | N | D | weak | Exon 1 |
| 182 | P | L | strong | Exon 1 |
| 187 | D | G | strong | Exon 1 |
| 188 | Y | N | weak | Exon 1 |
| 196 | N | S | weak | Exon 1 |
| 199 | T | A | moderate | Exon 1 |
| 204 | R | G | strong | Exon 1 |
| 210 | T | P | weak | Exon 1 |
| 211 | G | E | moderate | Exon 1 |
| 216 | Q | H | weak | Exon 1 |
| 217 | E | A | strong | Exon 1 |
| 223 | L | S | strong | Exon 1 |
| 235 | R | S | weak | Exon 1 |
| 236 | D | E | weak | Exon 1 |
| 239 | | Q | | Exon 1 |
| 246 | F | L | weak | Exon 1 |
| 249 | T | G | moderate | Exon 1 |
| 250 | R | | | Exon 1 |
| 256 | V | L | moderate | Exon 1 |
| 261 | F | I | strong | Exon 1 |
| 266 | N | K | weak | Exon 1 |
| 275 | R | Q | weak | Exon 1 |
| 278 | G | E | moderate | Exon 1 |
| 284 | W | R | strong | Exon 1 |
| 297 | L | F | weak | Exon 1 |
| 303 | V | A | strong | Exon 1 |
| 305 | S | N | weak | Exon 1 |
| 314 | | T | | Exon 2 |
| 315 | | K | | Exon 2 |
| 316 | K | R | weak | Exon 2 |
| 318 | K | E | weak | Exon 2 |
| 319 | E | A | strong | Exon 2 |
| 320 | G | A | weak | Exon 2 |
| 321 | P | S | weak | Exon 2 |
| 345 | G | C | strong | Exon 3 |
| 352 | E | K | weak | Exon 3 |
| 368 | | S | | Exon 3 |
| 566 | I | T | strong | Exon 3 |

Definitions

The term "resistance" or "resistant" as regards a pathogen should be understood to mean the ability of a plant, plant tissue or plant cell to resist the damaging effects of the pathogen and extends from a delay in the development of disease to complete suppression of the development of the disease. The resistance may be complete or partial and may be specific or non-specific to the pathogen race. A conferred resistance may be a newly inherited resistance or an increase in a partial resistance which is already extant.

Resistance may be quantified by methods known in the art. For example, resistance to *Helminthosporium turcicum* may be quantified by determining classification scores using phenotyping experiments in accordance with the scheme shown in the Table 4 below. For example, a *Helminthosporium turcicum*-resistant maize plant in the meaning of the invention exhibits an "increased resistance" to *H. turcicum* by at least 1 classification score, preferably by at least 2 classification scores or at least 3 classification scores, and most preferably by at least 4 classification scores. Preferably, a maize plant in accordance with the invention exhibits resistance to at least one race of *Helminthosporium turcicum* which does not correspond to the known race specificity known in the prior art. In a particularly preferred embodiment, a maize plant in accordance with the invention is resistant to all known races of *Helminthosporium turcicum*, i.e. the conferred resistance is not race-specific and may be particularly advantageous in the formation of a broad resistance to *Helminthosporium turcicum*.

TABLE 4

Classification score scheme for phenotyping experiments in field trials at various locations with natural and artificial *H. turcicum* inoculation (from the Deutsche Maiskomitee (DMK, German maize committee); AG variety 27.02.02; (DMK J. Rath; RP Freiburg H.J. Imgraben)

| Classification score | Phenotype |
|---|---|
| 1 | Plants exhibit no symptoms of disease, 0% |
| 2 | Beginning of infestation, first small spots (less than 2 cm) visible. Less than 5% of leaf surface affected. |
| 3 | Some spots have developed on a leaf stage. Between 5-10% of leaf surface affected. |
| 4 | 10-20% of leaf surface affected. Clearly visible spots on several leaf stages. |
| 5 | 20-40% of leaf surface affected. Spots start to coalesce. |
| 6 | 40-60% of leaf surface affected. Systematic infestation visible on leaves. |
| 7 | 60-80% of leaf surface affected. Approximately half of leaves destroyed or dried out because of fungal infestation. |
| 8 | 80-90% of leaf surface affected. More than half of leaves destroyed or dried out because of fungal infestation. |
| 9 | 90-100% of leaf surface affected. The plants are almost completely dried out. |

The term "hybridize" or "hybridization" should be understood to mean a procedure in which a single stranded nucleic acid molecule agglomerates with a nucleic acid strand which is as complementary as possible, i.e. base-pairs with it. Examples of standard methods for hybridization have been described in 2001 by Sambrook et al. Preferably, this should be understood to mean that at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule undergo base pairing with the nucleic acid strand which is as complementary as possible. The possibility of such agglomeration depends on the stringency of the hybridization conditions. The term "stringency" refers to the hybridization conditions. High stringency is when base pairing is more difficult, low stringency is when base pairing is easier. The stringency of the hybridization conditions depends, for example, on the salt concentration or ionic strength and the temperature. In general, the stringency can be increased by raising the temperature and/or by reducing the salt content. The term "stringent hybridization conditions" should be understood to mean those conditions under which a hybridization takes place primarily only between homologous nucleic acid molecules. The term "hybridization conditions" in this respect refers not only to the actual conditions prevailing during actual agglomeration of the nucleic acids, but also to the conditions prevailing during the subsequent washing steps. Examples of high stringent hybridization conditions are conditions under which primarily only those nucleic acid molecules that have at least 90% or at least 95% sequence identity undergo hybridization. Such high stringent hybridization conditions are, for example: 4×SSC at 65° C. and subsequent multiple washes in 0.1×SSC at 65° C. for approximately 1 hour. The term "high stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions. Less stringent hybridization conditions are, for example: hybridizing in 4×SSC at 37° C. and subsequent multiple washing in 1×SSC at room temperature.

The present invention encompasses nucleic acid molecules comprising or consisting of a nucleotide sequence encoding a protein, said protein being derived from the amino acid sequence encoded by the nucleotide sequence of SEQ ID NO: 1 or SEQ ID NO: 2 or from the amino acid sequence set forth in SEQ ID NO: 3 by way of substitution, deletion and/or addition of one or more amino acid(s). Herein, the term "one or more amino acid(s)" refers to, for example, 1 to 50, 1 to 40, 1 to 30, or 1 to 20, preferably 1 to 10, more preferably 1 to 7, further preferably 1 to 5, and particularly preferably 1, 2, or 3 amino acids.

"Operably linked" means linked in a common nucleic acid molecule in a manner such that the linked elements are positioned and orientated with respect to each other such that transcription of the nucleic acid molecule can take place. A DNA which is operably linked with a promoter is under the transcriptional control of this promoter.

"Introducing" in the meaning of the present invention includes stable integration by means of transformation including *Agrobacterium*-mediated transformation, transfection, microinjection, biolistic bombardment, insertion using gene editing technology like CRISPR systems (e.g. CRISPR/Cas, in particular CRISPR/Cas9 or CRISPR/Cpf1), CRISPR/CasX, or CRISPR/CasY), TALENs, zinc finger nucleases or meganucleases, homologous recombination optionally by means of one of the above mentioned gene editing technology including preferably a repair template, modification of endogenous gene using random or targeted mutagenesis like TILLING or above mentioned gene editing technology, etc. The term "introducing" may or may not encompass the introgression using conventional breeding.

The term "transgenic", "transgenical" or "transgene" is understood to mean that the respective gene is an exogenous gene that was introduced into the plant. The exogenous gene may be derived from a species other than the plant species into which it is introduced. Alternatively, the respective gene may be a gene already present in the plant species into which it is introduced, so that one or more additional copies of said gene are present as a result introducing the transgene. A "transgenic plant" is a plant into the genome of which at least one polynucleotide, preferably a heterologous polynucleotide, has been integrated. Preferably, the polynucleotide has been integrated in a stable manner, which means that the integrated polynucleotide remains stable in the plant, is expressed and can also be stably inherited to descendants. The term "heterologous" means that the introduced polynucleotide originates, for example, from a cell or an organism with another genetic background of the same species or from another species, or is homologous with the prokaryotic or eukaryotic host cell, but then is localized in a different genetic environment and thus is different from any possible corresponding naturally occurring polynucleotide. A heterologous polynucleotide can be present in addition to a corresponding endogenous gene.

Plant "organs" are leaves, plant stems, stems, roots, vegetative buds, meristems, embryos, anthers, ovulae or fruit. Plant "parts" can mean a fusion of several organs, for example a flower or a seed or a part of an organ, for example a cross segment from the stem. Examples of plant "tissues" are callus tissue, storage tissue, meristematic tissue, embryogenic tissue, leaf tissue, bud tissue, root tissue, plant tumour tissue or reproductive tissue. The term "cells" should be understood to mean isolated plant cells with a cell wall or aggregates thereof or protoplasts, for example.

The term "genetically edited" means that an endogenous gene is modified e.g. by means of random mutagenesis, TILLING or gene editing technology. For example, according to the invention, the endogenous gene of a plant may be modified to confer resistance (or increased resistance) to a plant disease caused by a fungal pathogen. Genetic modification may, for example, be achieved using methods of random or targeted mutagenesis (such as gene editing), or homologous recombination (optionally, supported by gene editing tools) or combinations thereof.

As used herein, "a modification", means that the genetic sequence has changed by at least one nucleotide. This can occur by replacement of at least one nucleotide and/or a deletion of at least one nucleotide and/or an insertion of at least one nucleotide, as long as it results in a total change of at least one nucleotide compared to the nucleotide sequence before modification, thereby allowing the identification of the modification, e.g. by techniques such as sequencing or PCR analysis and the like, of which the skilled person will be well aware.

The term "allele" refers to one or two or more nucleotide sequences at a specific locus in the genome. A first allele is on one chromosome, a second allele on the sister chromosome at the same position. If the two alleles are different, they are heterozygous, and if they are the same, they are homozygous. Various alleles of a gene (gene alleles) differ in at least one SNP. Various alleles of a resistance gene may either confer resistance, possibly different level of resistance to a plant against a fungal pathogen, i.e. causes differ types of phenotypes of the plant in response to infestation with fungal pathogen, or constitute a variant of the gene which is not able to confer resistance, i.e. the resulting plant phenotype is susceptible to a fungal pathogen.

According to the present invention, the term "regulatory sequence" means a nucleotide sequence which influences the specificity and/or strength of expression, for example insofar as the regulatory sequence confers a specific tissue specificity. A regulatory sequence of this type may be localized upstream of the transcription initiation point of a minimum promoter, but also downstream thereof, for example in a transcribed but not translated leader sequence or within an intron.

A "molecular marker" or "marker" is a nucleotide sequence which is used as a reference or orientation point. A marker for recognizing a recombination event should be suitable for monitoring differences or polymorphisms in a plant population. For markers, these differences are on a DNA level and, for example, are polynucleotide sequence differences such as, for example, SSRs (simple sequence repeats), RFLPs (restriction fragment length polymorphisms), FLPs (fragment length polymorphisms) or SNPs (single nucleotide polymorphisms). The markers may be derived from genomic or expressed nucleic acids such as spliced RNA, cDNA or ESTs and may be based on nucleic acids which are used as probes or primer pairs and as such are suitable for amplifying a sequence fragment using PCR-based methods. Markers which concern genetic polymorphisms between parts of a population can be detected using established methods from the prior art (An Introduction to Genetic Analysis. 7th Edition, Griffiths, Miller, Suzuki et al., 2000). These include, for example: DNA sequencing, PCR-based, sequence-specific amplification, assaying of RFLPs, assaying of KASP, assaying of polynucleotide polymorphisms using allele-specific hybridization (ASH), detection of SSRs, SNPs or AFLPs. Methods for detecting ESTs (expressed sequence tags) and RAPD (randomly amplified polymorphic DNA) are also known. Depending on the context, the term "marker" in the description may also mean a specific chromosome position in the genome of a species where a specific marker (for example SNP) can be found.

The terms "distal" and "proximal" describe the position of a chromosomal interval or a genetic segment in relation to a specific reference point (for example a specific polynucleotide, another chromosomal interval or a gene) on a whole chromosome; "distal" means that the interval or the segment is localized on the side of the reference point distant from the chromosome centromere, and "proximal" means that the interval or the segment is localized on the side of the reference point close to the chromosome centromere.

"closely linked" means two loci, two intervals, two genetic segments (e.g. resistance gene and flanking regions) or two markers (marker loci) which are less than 15 cM, less than 12 cM, less than 10 cM, less than 8 cM, less than 7 cM, less than 6 cM, less than 5 cM, less than 4 cM, less than 3 cM, less than 2 cM, less than 1 cM, less than 0.5 cM, less than 0.2 cM, less than 0.1 cM distant from each other, established using the IBM2 neighbors 4 genetic map which is publicly available on the Maize GDB website, or which are less than 50 Mbp (mega base pairs), less than 40 Mbp, less than 30 Mbp, less than 25 Mbp, less than 20 Mbp, less than 15 Mbp, or less than 10 Mbp distant from each other.

The term "interval" or "chromosomal interval" means a continuous linear segment on a genomic DNA which is present in an individual chromosome in a plant or on a chromosome fragment and which is usually defined through two markers which represent the end points of the interval on the distal and proximal side. In this regard, the markers which define the ends of the interval may themselves also be a part of the interval. Furthermore, two different intervals might overlap. In the description, an interval is specified by the statement "between marker A and marker B". An end marker of an interval may also be localized in a defined marker region to one side of the interval. A marker region is then defined by providing two flanking markers and constitutes a chromosomal segment on which more markers might be located, in addition to the flanking markers. Flanking markers determine the end points of a marker region and are themselves still a part of the marker region. If both end markers of an interval are markers in different marker regions on both sides of an interval, the description specifies an interval by stating "between a marker in a marker region X which is flanked by the markers C and D and a marker in a marker region Y which is flanked by markers E and F". A marker region may extend over up to 500 000 base pairs (bp), and can preferably be between 100 000 and 400 000 bp in size, or can particularly preferably be between 140 000 and 315 000 bp in size.

The term "introgression" as used in connection with the present invention means the transfer of at least one desired gene allele on a genetic locus of a genetic background into another. As an example, an introgression of a desired gene allele at a specific locus may be transferred to a descendant by sexual crossing between two parents of the same species. Alternatively, for example, the transfer of a gene allele may also occur by recombination between two donor genomes in a fused protoplast, wherein at least one donor protoplast carries the desired gene allele in its genome. In each case the descendants, which then comprise the desired gene allele, can then be backcrossed again with a line which comprises a preferred genetic background and can be selected for the desired gene allele. The result is fixing of the desired gene allele in a selected genetic background.

A "Locus" is a position on a chromosome where one or more genes are found which cause an agronomic feature or influence one. In particular, "locus" as used here means the HT2-resistance locus which confers resistance against the pathogen *Helminthosporium turcicum* or at least against a race of *Helminthosporium turcicum*.

The term "allele" refers to one or two or more nucleotide sequences at a specific locus in the genome. A first allele is on a chromosome, a second on a second chromosome at the same position. If the two alleles are different, they are heterozygous, and if they are the same, they are homozygous. Various alleles of a gene (gene alleles) differ in at least one SNP. Depending on the context of the description, an allele also means a single SNP which, for example, allows for a distinction between the resistance donor and recurrent parent.

EXAMPLES

The following examples, including the experiments conducted and the results achieved, are provided for illustrative purposes only and are not construed as limiting the present invention.

1. Cloning and Functional Validation of the Resistance Gene HT2 and HT3 a. QTL Mapping and Development of Recombinants

The donor line A619HT2 was crossed and backcrossed with the line RP1 to create a near isogenic line (NIL, RP1HT2A) with the main fragment of the original donor A619HT2 on chromosome 8 and very few other small donor regions. This NIL RP1HT2A was crossed with its recurrent parent RP1 to build up a F2 population. The same was done for RP2×RP2HT3A (original donor was here A619HT3). The recurrent parents RP1 and RP2 were susceptible to NCLB (Scores 7-9; cf. Table 4), while the donor lines A619HT2 and A619HT3 are resistant (scores 1-3). The scores of NILs RP1HT2A and RP2HT3A are 2-3 and 1-2, respectively.

The F2 populations were planted in the field with 720 individuals at the location Pocking, Germany. QTL mapping resulted in a peak (LOD value for population with RP2HT3A=168.77; LOD value for population with RP1HT2A=44.02) for both populations on chromosome 8 (1.1 cM and 3.5 Mbp frame). No other significant peak was detected. Recombinant plants (No. total~2000) were developed in several generations until F11 status. QTL mapping in F2 and further fine mapping with recombinants narrowed down the chromosomal region down to a physical interval of 490 kbp (genetic interval=0.2 cM). This interval includes the RLK1 gene.

b. Molecular Analysis of Target Region

From the lines RP1HT2A and RP2HT3A non-gridded BAC libraries were developed and screened with 7 probes from the target locus. For the RLK1 candidate gene region a contiguous BAC contig could be developed for both donor lines. Sequence analysis revealed that the donor line A619HT2 and A619HT3 are identical for the target region (in 1 Mbp). The candidate gene RLK1 cDNA sequence shows 97 polymorphisms (DNA level; incl. SNPs and Indels/Deletions) and 61 amino acid changes (protein level) between the lines harboring the HTN1 of WO 2015/032494 A2 and the HT2 allele. Out of the 97 polymorphisms, only 14 single nucleotide polymorphisms (SNPs) result in silent amino acid exchanges which probably do not influence the activity of the resistance gene. All other polymorphisms change the structure of the protein significantly by substitution, addition or deletion. Table 3 shows 15 amino acid exchanges for which a strong effect on the protein structure is predicted. Among these, multiple genotype specific additional amino acids have been identified. Compared to RLK1 cDNA sequences set forth in SEQ ID NO: 11 and 13 from the donor line disclosed in WO 2011/163590 A1, A619HT2 and A619HT3 differ in 31 nucleotides and 12 amino acids.

c. Functional Validation of the HT2 Allele of RLK1

(i) Functional Validation Using EMS Mutagenesis:

An EMS-mutagenized population from RP2HT3A was developed. The exonic regions 1 and 3 from RLK1 were screened and 3 positive mutants harbouring an amino acid change were detected (SEQ ID NOs: 16, 18, 20, 46, 48, 50, 52, 54, 56 and 58). In RLK cDNA of Mutant WVE16-92125-001 G at position 1625 replaced by A (see also SEQ ID NO: 15), leading to an amino acid exchange from Gly to Asp at position 542 (see also SEQ ID NO: 16); in RLK cDNA of Mutant WVE16-92149-012 C at position 95 replaced by T (see also SEQ ID NO: 17), leading to an amino acid exchange from Pro to Leu at position 32 (see also SEQ ID NO: 18); in RLK cDNA of Mutant WVE16-92168-005 G at position 115 replaced by A (see also SEQ ID NO: 19), leading to an amino acid exchange from Ala to Thr at position 39 (see also SEQ ID NO: 20); in RLK cDNA of Mutant WVE16-92168-024_WVE17-68687-013 G at position 73 replaced by A (see also SEQ ID NO: 45), leading to an amino acid exchange from Ala to Thr at position 25 (see also SEQ ID NO: 46); in RLK cDNA of Mutant WVE17-68655-008 C at position 301 replaced by T (see also SEQ ID NO: 47), leading to an amino acid exchange from Pro to Ser at position 101 (see also SEQ ID NO: 48); in RLK cDNA of Mutant WVE17-68625-014 G at position 715 replaced by A (see also SEQ ID NO: 49), leading to an amino acid exchange from Val to Ile at position 239 (see also SEQ ID NO: 50); in RLK cDNA of Mutant WVE17-68611-006 T at position 862 replaced by A (see also SEQ ID NO: 51), leading to an amino acid exchange from Phe to Ile at position 288 (see also SEQ ID NO: 52); in RLK cDNA of Mutant WVE17-68696-002 A at position 929 replaced by G (see also SEQ ID NO: 53), leading to an amino acid exchange from Lys to Arg at position 310 (see also SEQ ID NO: 54); in RLK cDNA of Mutant WVE17-68656-011 C at position 1289 replaced by T (see also SEQ ID NO: 55), leading to an amino acid exchange from Thr to Ile at position 430 (see also SEQ ID NO: 56); in RLK cDNA of Mutant WVE17-68630-001 G at position 1826 replaced by A (see also SEQ ID NO: 57), leading to an amino acid exchange from Cys to Tyr at position 609 (see also SEQ ID NO: 58). After selfing of these mutants, they have been evaluated in the field and greenhouse.

d. Expression Analysis:

The expression analysis of RLK1 in RP1, RP1HT2A, RP2 and RP2HT3A in non-infected and infected leaf material showed a similar expression in the NILs RP1HT2A and RP2HT3A. The expression is down-regulated in the infected leaf material. This response to infection could also be shown for the HTN1 allele of RLK1.

2. RLK1 Allelic Series and Identification of the Relevant Region for the Resistance Reaction In order to identify a relevant region for the resistance reaction to the pathogen *Helminthosporium turcicum*, the following analysis are carried out: Bioinformatic analysis of re-sequencing of the RLK1 gene in different donor lines and recurrent parents reveals the amino acid region relevant for the resistance reaction. Therefore, genomic sequence primer pairs for RLK1 have been developed to cover the exonic regions. Exon 1 could only be covered partially, and Exon 2 and 3 completely. The developed amplicons were amplified and sequenced in 96 genotypes with the PACBio-sequencing technique. The sequences were assembled to consensus sequences per genotype. For some genotypes, multiple consensus-sequences were obtained. The consensus sequence with the highest amount of sequencing reads was chosen for an assembly of all 96 genotypes. The haplotypes were determined according to the exonic region/parts. For Exon 1, 12 different haplotypes; for Exon 2, 7 different haplotypes; and for Exon 3, 9 different haplotypes were detected. The genetic distance was calculated within the software Lasergene MegAlign (DNASTAR, Inc.). The different haplotypes were assembled on DNA and Protein sequence level (see Table 5). As a result, the Exon 1 and 2 regions seems to be highly variable for the gene and harbor the WAK-associated domains. This protein part is located in the intercellular space and could interact with fungal proteins. Variances in these two exons are interesting candidate base pairs for this interaction. On this basis, it is possible to identify haplotypes of Exon 1 and 2 in new alleles of RLK1 which are able to confer or increase resistance at least to the pathogen *Helminthosporium turcicum*.

Furthermore, phenotyping of different donor lines, near isogenic lines and recurrent parents and haplotype analysis of the RLK1 locus as well as expression analysis of RLK1 in different donor lines, near isogenic lines and recurrent parents combined with the phenotypic analysis are carried out for identification of relevant region for the resistance reaction and finally for identification of new allelic variants of the resistance gene. Evaluating all described datasets should narrow down the relevant region for the resistance reaction.

TABLE 5

| Genetic distances [%] between different exon-based haplotypes | |
|---|---|
| Homology on DNA level<br>Total sequence: >60% | Homology on protein level<br>Total sequence: >60% |
| Exon 1: >85%<br>Exon 2: >60%<br>Exon 3: >98% | Exon 1: >75%<br>Exon 2: >60%<br>Exon 3: >98% |

3. Resistance Reaction to Other Pathogens

A set of genotypes harboring the different RLK1 alleles have been inoculated with other plant pathogens like Southern corn leaf blight (*Bipolaris maydis*), Common rust (*Puccinia sorghi*) and *Diplodia macrospora* (*Stenocarpella macrospora*). A common feature of these pathogens is that the infection relies on a very similar biology of the fungi and on the fact that they penetrate the host via leaf tissue. A first experiment with Southern corn leaf blight (*Bipolaris maydis*) indicates also a resistance reaction of the HT2- and HTN-allele of RLK1.

4. Introducing Resistance to NCLB Caused by *Helminthosporium turcicum* into a Susceptible Genotype Via *Agrobacterium*-Mediated Transformation Three different constructs with the HT2 cDNA sequence (SEQ ID NO: 2) under promoters with different activity have been transformed into the susceptible maize genotype A188: Construct A with the HT2 cDNA sequence (SEQ ID NO: 2), the native promoter region of ~1980 bp (SEQ ID NO: 4) and terminator region (SEQ ID NO: 5) (vector p7U, see FIG. 1), contruct B with the HT2 cDNA sequence (SEQ ID NO: 2), the Actin promoter of *Oryza sativa* (SEQ ID NO: 43) and terminator region (SEQ ID NO: 5), and construct C with the HT2 cDNA sequence (SEQ ID NO: 2), the EF1 promoter of *Brachypodium distachyon* (SEQ ID NO: 44) and terminator region (SEQ ID NO: 5). To produce for example the vector p7U-nativeHT2_CDS_2, the expression cassette containing the HT2 gene under control of the native promoter and terminator was transformed into a binary vector containing an herbicide gene (e.g.: BASTA resistance, glyphosate resistance or ALS inhibitor resistance) for subsequent transformation into *Agrobacterium tumefaciens* for *Agrobacterium* mediated plant transformation into maize (*Zea mays*) genotype A188. TO plants stably transformed with the different constructs have been multiplied and progenies grown in greenhouse are tested for resistance to NCLB. Transgenic plants with all different constructs showed an increase in resistance to NCLB, however to different degrees dependent on the location of integration and the promoter strength.

5. Introducing Resistance to NCLB Caused by *Helminthosporium turcicum* into a Susceptible Genotype Via Gene Editing The allele of RLK1 in susceptible maize genotype A188 has been identified, sequenced and a cDNA predicted (SEQ ID NO: 21). A comparison between the cDNA of this A188 allele and cDNA of HT2 shows that the sequences show a sequence identity of 99% (FIG. 4). However, there is at a position of 1458 to 1459 of the A188 allele a 2 bp insertion "AC" which causes an early stop codon after a Cysteine at position 513 (SEQ ID NO: 22). By elimination of this 2 bp insertion using gene editing based in TALENS or CRISPR systems, the HT2 resistance could be restored in the genotype A188. FIG. 5 shows in the alignment between the RLK1 protein derived from the modified RLK1 allele of A188 (SEQ ID NO: 24) and the HT2 allele the high level of identity on amino acid sequence. The cDNA of the modified RLK1 allele from A188 is shown in SEQ ID NO: 23.

The invention claimed is:

1. A method of identifying or selecting a *Zea mays* plant having increased resistance to Northern Corn Leaf Blight caused by *Helminthosporium turcicum* races 0, 1 and N and having a susceptible response to Northern Corn Leaf Blight caused by *Helminthosporium turcicum* races 2 and/or 3, or a part, a cell or seed thereof, comprising the following steps:

(a) detecting the presence of a nucleic acid molecule in the *Zea mays* plant, or part, cell or seed thereof; and (b) identifying the *Zea mays* plant in which or in whose part, cell or seed the nucleic acid molecule is present, as having a resistance or an increased resistance to Northern Corn Leaf Blight caused by *Helminthosporium turcicum* races 0, 1 and N and having a susceptible response to Northern Corn Leaf Blight caused by *Helminthosporium turcicum* races 2 and/or 3; or (c) selecting the *Zea mays* plant in which or in whose part, cell or seed the nucleic acid molecule is present, wherein the nucleic acid molecule comprises a nucleotide sequence selected from the group consisting of:

(a) the nucleotide sequence set forth in SEQ ID NO: 1 or SEQ ID NO: 2; and (b) a nucleotide sequence encoding the amino acid sequence set forth in SEQ ID NO: 3 or an amino acid sequence with one conservative substitution relative to the amino acid sequence set forth in SEQ ID NO: 3.

2. A method for detecting the presence or absence of a nucleic acid molecule in a *Zea mays* plant comprising the following steps:

(a) isolating DNA from at least one cell of the *Zea mays* plant, and (b) using a molecular marker to detect the presence or absence of the nucleic acid molecule, wherein the molecular marker is able to detect at least one single nucleotide polymorphism, deletion or insertion diagnostic for the nucleic acid molecule and/or comprises at least one oligonucleotide suitable to anneal as a forward primer or a reverse primer to a region in a genome of the *Zea mays* plant which shows a cosegregation with the nucleic acid molecule, wherein the nucleic acid molecule comprises a nucleotide sequence selected from the group consisting of:

(a) the nucleotide sequence set forth in SEQ ID NO: 1 or SEQ ID NO: 2; and (b) a nucleotide sequence encoding the amino acid sequence set forth in SEQ ID NO: 3 or an amino acid sequence with one conservative substitution relative to the amino acid sequence set forth in SEQ ID NO: 3, wherein genomic flanking regions closely linked to the nucleic acid molecule do not contain an A619HT2- or A619HT3-derived interval located between alleles of marker SYN14136 and marker MA0021, or an A619HT2- or A619HT3-derived interval located between alleles of marker MA0022 and marker SYN4196, wherein the marker SYN14136 is at position 131681497 in reference genome AGPv02 and is detectable using primers comprising the nucleic acid sequences of SEQ ID NOs: 25-27, the marker SYN4196 is at position 161766769 in reference genome AGPv02 and is detectable using primers comprising the nucleic acid sequences of SEQ ID NOs: 40-42, the marker MA0021 is at position 151907173 in reference genome AGPv02 and is detectable using primers comprising the nucleic acid sequences of SEQ ID NOs: 34-36, the marker MA0022 is at position 152046529 in reference genome AGPv02 and is detectable using primers comprising the nucleic acid sequences of SEQ ID NOs: 37-39, and the A619HT2- or A619HT3-derived interval comprises the amino acid sequence of SEQ ID NO: 3, and wherein the nucleic acid molecule encodes a polypeptide capable of conferring or increasing resistance to Northern Corn Leaf Blight caused by *Helminthosporium turcicum* races 0, 1 and N and conferring a susceptible response to Northern Corn Leaf Blight caused by *Helminthosporium turcicum* races 2 and/or 3 in a *Zea mays* plant in which the polypeptide is expressed.

3. A method for identifying the *Zea mays* plant using the method of claim 2, the *Zea mays* plant having an increased resistance to Northern Corn Leaf Blight caused by *Helminthosporium turcicum* races 0, 1 and N and having a susceptible response to Northern Corn Leaf Blight caused by *Helminthosporium turcicum* races 2 and/or 3, and comprising the nucleic acid molecule endogenously, the method comprising detecting in the *Zea mays* plant alleles of at least two markers, wherein at least one of said markers is within the chromosomal interval between SYN14136 and the nucleic acid molecule, and at least one of said markers is within the chromosomal interval between the nucleic acid molecule and SYN4196, and wherein the marker SYN14136 is at position 131681497 in reference genome AGPv02 and detectable using primers comprising the nucleic acid sequences of SEQ ID NOs: 25 to 27, and the marker SYN4196 is at position 161766769 in reference genome AGPv02 and detectable using primers comprising the nucleic acid sequences of SEQ ID NOs: 40 to 42.

4. A method for increasing resistance to a Northern Com Leaf Blight caused by *Helminthosporium turcicum* races 0, 1 and N and having a susceptible response to Northern Com Leaf Blight caused by *Helminthosporium turcicum* races 2 and/or 3 in a *Zea mays* plant, comprising the step of reducing a level of expression of a nucleic acid molecule, wherein the nucleic acid molecule comprises a nucleotide sequence selected from the group consisting of:

(a) the nucleotide sequence set forth in SEQ ID NO: 1 or SEQ ID NO: 2; and (b) a nucleotide sequence encoding the amino acid sequence set forth in SEQ ID NO: 3 or an amino acid sequence with one conservative substitution relative to the amino acid sequence set forth in SEQ ID NO: 3, wherein the level of expression of the nucleic acid molecule is compared to the expression level of the endogenous gene in a resistant wild type plant.

5. The method of claim 1, wherein the nucleic acid molecule comprises the nucleotide sequence encoding the amino acid sequence set forth in SEQ ID NO: 3.

6. The method of claim 2, wherein the nucleic acid molecule comprises the nucleotide sequence encoding the amino acid sequence set forth in SEQ ID NO: 3.

7. The method of claim 3, wherein the nucleic acid molecule comprises the nucleotide sequence encoding the amino acid sequence set forth in SEQ ID NO: 3.

8. The method of claim 4, wherein the nucleic acid molecule comprises the nucleotide sequence encoding the amino acid sequence set forth in SEQ ID NO: 3.

* * * * *

SEQUENCE LISTING

<160> NUMBER OF SEQ ID NOS: 58

<210> SEQ ID NO 1
<211> LENGTH: 24632
<212> TYPE: DNA
<213> ORGANISM: Zea mays

<400> SEQUENCE: 1
atggctgctc acctaccacg cctccccgtc ctcctcctcg tcctcctcgc tgcccatgtc 60
gtctccacct ccgcccatgc cgagcctcct cttccgagcc cttacagcac ctccgcccat 120
ggcgagcctc ctcttccgag cacttacaac gtctccatgt gctcggaatc gttctggtgc 180
ggcggcgtcg aaatccgcta cccgttctat cttgccaacg caaccgccga ctacagcggg 240
agctactact cctgcggcta caccgacttg agcgtttcct gcaaactcga ggtcgagggg 300
ccgacgacga catggacccc taccatccgt ctcggcggcg acaactacac cgtcaagaac 360
atcttgtacg actatcatac catctcactg gcggacagcg atgtgctcgg aggcggcgag 420
tgccccgtcg tccaccacaa cgtcagcttc gacgagacgt ggctgcacaa ccccagcgcc 480
ttcgacaacc tcaccttctt cttcggatgc cactgggggc cacgcgatac actgcctgaa 540
tttgccggca acaacatcag ctgcgccggg ttcagtactc cagctatcag cggtggaggc 600
tccttcgtgt tcaagcctga agatcttgac gaacatgcgg agcaggagtt ggcttcacac 660
tgcgacgagg ttttctccgt gccagtgaga agcgaggctc tgcagcaggc gatcgtcagc 720
aacctcagcc tcggggacgg gtacggcgag ctgcttaggc aggggatcga gttggaatgg 780
aaacggacat cggaggatca gtgtggccag tgcgaggaat cgggctccgg cggacggtgc 840
gcctacagcc agaagagaga attccttggc tgcttctgca gcggagggaa ggcgggcaac 900
ccgttctgca aaccatcaag taaagtcctg aaccgaccct cccttatttt tttttcattt 960
tttgcaatca ccagagcacg catcggttgc gtcagtatct tgcaacctcg tagctagccc 1020
cgcagtgtcc cctgtgtgcg agtaccgcgc tgctccagct tgcctcctgc taacgcctaa 1080
cggtgaatgc ttcatgcttg acatgatcta gctagtctac actttgcttg ggtttgcct 1140 gggagctgga aattctggct cctgtttgca tcactcgaca aggacgcttt cagacttgcg 1200
actctcgttc tgcttttgca ccaaatccgt gttttttcat ttcgtgatcg agattaatct 1260
agcgtagaga tgtcaatggg tatccgaaac tcgaaacccg atggattttt actctattag 1320
gtacaagttt gaatcaattt tcatatcata gatttgttaa taggcacaaa tctatatcca 1380
acaggttcat agatacgggt ttgttcctac agtaatcaaa tccgtaaacc catgagtttt 1440
ttagacccga ccaaacctag cgtatattgt cattttattt tataaacgaa caacaaaatt 1500
attatctctc tatttacttc ctattttttt atcggttggt gaatgtataa gtagttggtg 1560
agagtgttgc ttgcttgcta ttataatatt tagttattta ctagtgttat atatgtggtg 1620
gatggataac ttattgaaaa ggtcacttga ttatacaact tattatttgt attcattctt 1680
tctactaata atttttatat caaatcatga actcggtgtt tatcatataa attttggacc 1740
atgatcttat taatcatcac gatagttatt aattatgaga aaaacaaata tattggagat 1800
aaaaccctcg gctaacccgt taacccgatg ggcacgggtt tgaacaaaat ttcaaattta 1860
ttatgaatac aagtttttta acaaatatag atatgtttca tggatagagt ttgagatgac 1920
aaaatccaac ggatttgtat ccgttgccat ctctatccgg cggcccttac cgtgctccac 1980
gagcagaggt cgtatcgtcc ctcttcccgt gtcgcctgct tcgcgttgcc gaacggagac 2040
gtttggtagc gttggccggc tctagcagtc gggtcaattt ttttgttgtt gttttcgatg 2100
ttgttggatt tttgttccgt ataagccatg ttttggtaat ttatttagtc cagccgaatc 2160
cgaagacgtg tttgctgggt tggagacttt ggagttgcta gtcatgatat gctttctact 2220
cggtttgatt tcaacccagt taggctatat ttgatactct agtatttatt ccaatataaa 2280
tggtttgaaa gggattaaga tataaattag tttaatttat atctttaatt tctcttaacc 2340
catatgtatt gggctgaata ctaagtatca aaacaagccc ttatttaaga tgcattttct 2400
ttacagttac acgtggccac tattgtgtgg ggtaggccga tcctacttgt cagtgctcat 2460
tcgagagcaa agataccgaa ggagattaga gagactaaaa gctttttact atttaaaatt 2520
agataataag acgatttaat cccgttccat atctttgctc taaacaaacc ctcaatgatc 2580
atatatctcg gaagatccgg ccggctgttc tttatttatc aagtgatgac tgctgaccgc 2640
ttatagaata tatattttaa agcaaaattt cttctacatc agtaaaagga ctagacgaaa 2700
caatgatgca tttctctaac aaaagaaagt agaattatca agcggagagc caagaccaaa 2760
agccttacat ctatgggcgt caaccaatga taccgcgaac caccccagct ggtctatact 2820
gtctgtcacg acccagcgag taaccgtgtg gctacgctgt tagcttagga ttgaatgaaa 2880
tgctcggttc attaataaat cagctcacga gttaaatgat ttattatata acgaaactat 2940
atgcatatta tttaccaggg tgacgacagg gggcataggt gggcaatatc caccctaatg 3000
ctcctctaat tctataggga ttgttaattt atttagctaa ttatcatgta aacgatataa 3060
aaaatgtttc taacagcccc acggtccacc ctaatcttag accctagctt cgcctgttac 3120
gataaatatg ttatacatgt gtagtgtcta tgtcctatga attaaactaa tgattgatga 3180
actgtgctta tatattaaat tggtctatgc gaatataact atgtgttaaa ctgatgaaca 3240
tgtgtgtgaa ttgtgaattg ataagtgatg agttgtgtct aatttagtgt tatattgatg 3300
tgttttgtga aactatgagt ataattaata ttttctataa ttaaatttgt ttaaaattaa 3360
ctagaaattg attattatat atatatattg tttttctgct ctaattcgca agctaaacaa 3420
gcaagctcaa gctcgtaaac gagccgaacc gagctgactc tgtggctcat taacttaaca 3480
acccgagccg gaccaacttg ttagcttaac gagccagctc gaatacggac gagttgagcc 3540
gagctggcat gatatccagc cctaattagg ctcgtaccag tgcaacatat ccctctcgcc 3600
tttgtcacgt ccagacatgt caatgggccc cgattcccgc aaggaattcc tctattaagg 3660
gatgatgatg agaaagtttc tcccccacgg aaaaattctc tcctgacgca taaacgggga 3720
caacactcca catccccatt cctcgtgggg acctattaaa cttacatatg gtgatgtttt 3780
catgtaaaag ttaatgataa aaataaataa ttacgttgtc aagatatcac tttttgtaca 3840
aatgtgctca ttctgatgta gacatatttt ttcttacatc taacaatctg tatgagtgag 3900
aatgttttgt attaataaca aagtaagtat gttctaatta taatttaagc gggtccgggg 3960
atccccgatg gggatttata cccttgggaa acgaagatgg ggaagaaatg tcctacacaa 4020
gttttcatgg cgatcctcgc ggggaacttt ttcgtcgtgg ggatagggat ggggagctaa 4080
aacccgatga ggaattcctc gttgtcatcc ccagtcacgt caactctcga ctctactatt 4140
gtctctgctg catagtctgt ggtaaactat agcctcagcc tatagcacat cagcttttct 4200
atttcagaat taagtaattc atgcagtttt atttcaacgc tcgaaaatta cacaacataa 4260
tattttttat tgaattaaaa attataaagt gcatacaaat caataaaaat atattataat 4320
taaaacatat ataaatctaa tcggagacct cgatcttatc ctcgtcttcc accacctctt 4380
tttgttttgc ttctggttcc tcttcttcgt catcaaccag accacgtcct ttttcgaaca 4440

```
tctttatggc cttggcatgg gtttatcttt cagctaggtc catatccctg gttgaatggc   4500
tctttagagt attccattgc tttaaaagct tggtcttcac taatccaccc cacaagttct   4560
tcattttaaa tgcttcactt gttgactgtt gcttgtggct tccttccctt tccccttcac   4620
cttcatcttt cgcccagccg cctttgccct atcacgccct actgatcggg gcacttcctt   4680
cttggtatct ttagtgcctc cagaactata ttcactagag acactgagtc gggttatctt   4740
attcgtagtc ccattttatc ctagaacctt gtcattgctg cctccatgac cattgcctcg   4800
tctgcttcgc tctgatgcaa cttttcttct cgaaggtagt atccattaaa cttgctcacc   4860
tcccggttgt aggtgcccta atgattttta agttgcttgg cggtttgagg atatcaaggg   4920
tcggaggtgg agttatatgt tgccgctatt tgactccaaa aacatgatcc agacttattg   4980
ttgacagggg ttgaattatt agaatgcata ttccaagaat taacctataa tataagtaaa   5040
ctacaaatat aaatattaaa taaatgagaa atgattcact caccaacttt tcctcatagt   5100
cattcatcca ttctagcctc tttggacact tttctttcgg cccaggattt tcctcggctt   5160
ggttttcaaa tccaacatac tagacatgta tgtggaattg gaggaggtgc tcatacagag   5220
gtggagcata tgcaggaggg gcatacagag gtactgagaa agaagtttga cttccatccg   5280
cagcaggtgg aggggcatac agacgtaccg aggaaaaagc ttgaattctg gcttgggaag   5340
ttggaggttg accatatgaa ggcggcaagt atgaatacag atgataggaa aaggttatgg   5400
tggtggtgga cgcgcaactg aaaatagtgc atgggggact gaagctgaaa catcagagcg   5460
acaatgtagt ggagagactc atcaaacgga ggggtttgtg acccatcgga ctacaagaga   5520
tccatgaagg tgttcaaatc tggggaccaa cccgatattg tgtgaacaga ggggagtttg   5580
gaagagagaa acgaaatgaa atggtgtgtg gaatgagctc aacccaagta gaggtactta   5640
caaagggatt ggggatgaaa tttgtgattt tttgcaattt tttatttttt ggattccaaa   5700
cgatcaaaaa caactagttg caatagctag ctgtgggggga tagatatccc ccgggtccac   5760
taagggagta aaagacctca cgaaaggccc aagggcccaa taaatcgtaa ggtcattctt   5820
ccgtgggcct ggggagaaac aaccaacaaa acagagaaga cgtaagaccg gattggtgca   5880
aacccggacg gcccacaacg tcgaacgagt aaatcgcaac agagacccga ctttcccgcg   5940
ctggagcccc catgcaacgg agccatgcga ggataagtcg gcgagggtta cgtagggata   6000
aactcaagag gttcactacc ttttagctac ttgttgttat catatccacg tgtactgccc   6060
cacggtcgag tatataaggc ctagggggca ccccttcaga acgatcgacc ctatcttact   6120
tagccaccca cagcaactct ctgtgtcttc aatccagaga gccctcttgt aaccacgctc   6180
acatactcac caggacgtag ggtgttacgc atctctaagc ggcccgaacc tgtaaatctt   6240
gtccactgtc cctcgtgtga tcggcacgaa ctgttttgct acagtcgtcg acaccgtcct   6300
actcctagaa acaccttgag gggcaacccc gggtgtgcgg ttggacccaa aacaccgaca   6360
gctggcgcgc caggtagggg gtgtgtcgac gatccaagct agctcaatgg ccatcacctt   6420
ctacagcaag atcaccatgc gtcctggatc cgtattctgc ttcgggacaa tctcatctgt   6480
agcggatgaa gagggaattc tacaccgtat cgcagatccg ccggaaaaga agactcctcc   6540
aacgaactcc gaaaatgccg gagaggcaca acctccagct cttcggaaaa agatcgtctc   6600
cggaaaggcg ggggccgagg gctcgctgac ccggaagact ccgttgtcta cttcctcgac   6660
gaaagaatgg acacggatca cgaggaagaa ggagaccggg gaaaagcaag tcgttctttc   6720
cgttcctccg gtctcaaagg agaacggaaa gaaagtcgcc gcgacagcag caccattcta   6780
ccccgacgtc ctcttcgtcg ggagagtgga gtcgcccacc gtctctgacg acgaaccgac   6840
```

```
cgcgcccgga gaagagccgc ctcaacgaga atcccgccga cggagaaacc ggcgcaggaa   6900

cgttcgacga catcacgcgg ccggagaacg ggatccggag cagcctgtct cgcgagacga   6960

ggtctcggag ataggagaaa ctccggaaga acgcgtcttc agagaacgaa ggaactcccg   7020

acgacgtgat cgccggcggg ctcaggaaca ggccgagcaa gatgcaaggc aacgccggga   7080

gaatccgctc ttcgggcgca acctaaatcc cgacttcgcc cgagctatga acacgccaag   7140

cgaagtcgga ggggtactag cttggatagc tgatggactt cctcgaactc ccgacgccga   7200

gggataccga cgcctgttca cccaggcagc caaccatctt ctacctctcg ctcacccgcc   7260

gaacgatcta cgacacgcca tcaacagtcg ccgagacgcg cgaagctcca tcaatgcttc   7320

gcgcgaacgg cggcatgaga acgagattcg ccgtcgggag gaatacgacc gggatcatgg   7380

catcccgact cagagccagg ccaccaggac tgagtcggca acagcctcaa ctggcggaac   7440

cacccgggga cggccgagga accacaatca caactcccct ccccgggaca gacatcgtcc   7500

ccgacaacag gaggacacgt gcggagtgtc cgctcttact ccacgcctta gggccatcca   7560

atggcctccc aacttcaagg tatccaatgt cgacaaatat gagcctaagc aggatccagg   7620

gggttggcta gccgtctaca ccaccgctgc tcgggctgtc ggagcatctg aggacgttat   7680

gaccgcgtat ctgcccatcg tccttgggca agatgcgcta cagtggctac gacatttacc   7740

ccgacactgc atcgacgact ggggagactt cagtcgacgt ttcaccgcca acttccagtc   7800

cctctccgac aagccagcgc aaccgtggga cctcaaatcc atcaagcgtc gggggggatga   7860

gactctccgg tcgtacctca aaaggttcca gaccatgaga aatcgcatcc ccgaggtcac   7920

ggaggcggcc gtgattgagg acttctacag aggatccaac gactcggctt ttgtccgagc   7980

catactacag aaagcgccga ctacttccga ggagctgttc cgggaagccg acctctacat   8040

caccgccgac gagcgagctc aggacctcat cggaggagcg aagcctgcac cggcagcacc   8100

acgacgcgac gcgaaccaac cacccgacaa acgctgggag aagaggcctc gcgaagaagt   8160

acacgccgcc ggaccacctg cctctcgcgc ccgaggagga cctcgtggag gcgagcgcac   8220

gctggacgac atcctcgacg cccagtgccc ataccacaag gacatgcgcc acactcttcg   8280

caactgccgg gacttcaagc actccgttgg gcatggccga cccttccaac ctctacctcc   8340

tcctccgccg aggggaggac cggatgaacc gcgacaacct catcagccgg aggagggagg   8400

aggaggagct ttcccacgcg tcgacaggga ggtcaacgtc atcttcggcg gacatgggtc   8460

gcaggagaac aaaagacaac aaaagctcaa cgaccgccag atactggtgg cgaccaccgg   8520

tcctcccgcc ccataccggt ggtcagaaca cccgatcacc ttcactcggg aagatcaatg   8580

gctcaacttc gaccatccag gcaaataccc gctcctcgtc gatccggtga tccgagagag   8640

ccgggtgaag aaggtgctag tggacggggg gagcagcatc aacatcacct tcccccggac   8700

gctccaaggc ttgggggctc acctcaaaga gctccacaag tcggacactc ctttctttgg   8760

catcgtgccg acggagggag aatacccgct ggggcacatc tacatgccgg tcaccttcgg   8820

aactccggag aactacagaa tcgagttcct gaggtttgaa gtggcgaact tcgactgcgg   8880

atacaacgcc atcattggaa gaccgggatt ggccaaattc atggccattc cgcactatac   8940

gtacatgata ctgaagatgc caggaccgca agggatcata actgtgcgcg ccgacttcca   9000

aggcgccgca gaatgtttcc gagtggccat ccaggcagcc ctcaccacca agccgccaac   9060

ggtcccctct acactggcga attctaagcc tgaggaggac ctcgccgtac cggcaaacga   9120

agctcaggcc gcgacctcta tgcggccgac tgaagaaacc aagcgaatca acctggggtt   9180
```

-continued

```
cgctgatgag cgcaagacgg ccatcatcag ctccagcttg aacgacaaat aggaaggcgc   9240
gctcgtccag ttcctgcaag ataaccgaga tgtattcgca tggcaacctg cggatatgcc   9300
gggagtccca agagaactgg ccgagcacaa gttgaaggtt tatccccagg cgaggccgat   9360
ccggcaaaag ctacgtcgtt tcacgcccga caagagagag gccatttgcg ccgagttagc   9420
tcgcttggtt gcggctggat ttattagaga agtattacac cccgagtggt tagctaaccc   9480
tgttcttgta ctcaaaaaga ataaagtgga ttggcgcatg tgcgtcgact atactgatct   9540
caacaaacac tgtcggaagg atcccttcgg gctcccgagg atagatcagg tggtggactc   9600
taccgccgga tgttctgtgc tgtcattctg agattgctat tccggatatc atcagattag   9660
tttggcaaaa gaagacgagg agaaaacggc gttcatcact ccgtttggtg ctttctgtta   9720
cacctccatg tcgttcggcc tcaaaaacgc tggagcgact tatcagagag ccattcaaac   9780
atgcttagcc aatcactggg gcaagcgtgt ggaggcttac gtagatgatg tggtgatcaa   9840
aacagagaat tcggaaaact tcatcgaaga tttacagctg gttttcaaca gcctgagaag   9900
atatagatgg aagctcaatc ctgaaaaatg tgttttcggg gtaccagcag gaaagttgct   9960
cgggtttatc gtcagccact ggggaattga ggctaatcca gataagattg aagctatcat  10020
gaagatggaa gctcctcggt cacaaaagaa ggttcagcga cttactggat gtatggcagc  10080
tctgagcaga tttatatcca ggctgggaga aaaaggttta ccattttaca agctactcaa  10140
gaaggtggat aagtttcaat ggacttcaga agcacaagaa gctctagacg cactgaagaa  10200
attcttgaca acagcaccag tactgaaacc accccggcga gctacgccga ctcaaccggc  10260
tgaagatttg ctgctgtata tctcttgcac gactcatgtg gtaagcaccg cgttggtagt  10320
cgagcgagta gaagaaggac atgcctatcc agtacaacat cctgtttatt tcatcagtga  10380
agttctaggc ccctcaaaga aaaagtatcc tcaggttcag aagctattat atgcagtact  10440
tctaactgcc cgcaagctgc gtcactactt tgacgaccac aaagtcatag tagtcactgg  10500
ttttccaata ggggacattc ttcacaacaa ggaagccatt ggccgaatag ccaagtgggc  10560
ttgcgagctg ggatcccacg acatcgagtt ccgacctcgc actgccatca aaactcaagc  10620
actggttgat ttcgtatcag agtggacaga acagcaagta ccagataatc cagaaactgc  10680
agaagtatgg cgaatgtatt ttgacggctc gctgaagctg cagggagcag gggcagggat  10740
tctcttcact gcacctggag gcgaacacct caagtacgcc ctctagttgc tattcccggc  10800
ctctaacaat gcagccgagt atgaagcttt gatacacgga ttgaacatcg ccatatcact  10860
gggcgtcaag agattgatgg tatacggaga ttctctggta gtcatcagcc agataaacaa  10920
ggaatgagat tgttcaagtg attcaatggg aaaatactgc gctgccgtcc gaaagctgga  10980
agataaattc gagggtctgg aatttcatca tatagaaaga gatcgaaaca cagcagccga  11040
cgtactgtcc aagctcggat ccggtcgaac tcaggtccca accggagtct tcgtgcaaga  11100
aattctgcag ccgagtatct caatggatca aacagaagag tgcaacgtca taaatcaacc  11160
tgagtcagac tctgatgact ggagaaggct gattattaag tacataaaga atgacgaaga  11220
accagacgac aagaactcgg cagagcgcat tgccaggcag tcggctcgct atacactcat  11280
tggggaggag ttgtacagaa ggggcgcatc aggcatcctc atgaagtgcg ttctcccgtc  11340
cactgggaaa caacttctgg aggaggtcca cgcagggcaa tgtgggatac atgcagcatc  11400
cagaacacta gtcgggaagg ttttcaggtc aggattctat tggccgacgg cgaagaacga  11460
tgcagccgag ttagttcaga gatgcgaagc ttgccaatac ttgtcaaagc aacagcacct  11520
gccagcacag caactacata ccataccagt aacctggcct ttcgcatgct ggggactgga  11580
```

tatgattgga cctttcaaga aagctcaagg gggatatact catgtattgg tggcgattga 11640
caaattcact aaatggatag aattcaagcc cattgcttct ttaacctctg ctaaagccgt 11700
ggaattcata caagacataa tattcagatt cgggataccc aacagtatca tcactgactt 11760
aggatccaac tttaccagtt cagaattctt cgacttctgc gagcaaaaga gcattcagat 11820
caagtatgca tctgtagcac atccaagagc caacgggcag gttgagcgag ccaacggaat 11880
gatattggag gcactcagga aagggtctt cgacaagaat gaaaaattcg caggaaagtg 11940
gataagagaa ttaccttatg ttgtttggag cctaagaacc caacctagcc gagccctgca 12000
tggaaacact cctttcttca tggtctatgg gtcggaggca gtgctacctg ctgatctcaa 12060
gtttggggcg ccaaggttga tcttcgaaag catagcggaa gctgaggcca ccaggctgga 12120
ggacgttgat gtacttgagg aagaacggct gaacgcggta atccaatcag cacggtacca 12180
gcagactcta aggcgctatc acgacaaggc tatgcggcaa cggttctttt cagtaggaga 12240
cctcgtcctc cgccgaattc taacgggaga gggacggcac aagttatcac ccttatggga 12300
aggacccttc ataatagcag aagtcactcg gcccggatcg tatcgcctca ctcagatgga 12360
tggcacagaa gttgggaact cctggaacat agagcacctc agaaaatttt atccctagct 12420
gtatttcaaa actgctgggg cgacaatgta ttctgtaaag tggaaatatg tcgtcaataa 12480
agagagattt caaagatact cggctcgttt acaattgact tgcattctca cttaactcgg 12540
ggtgaccact atgccctaca aacggagcaa tcggcttaag tcggcaacga cttaaggcga 12600
tgcaacatgc tcacgcttac ttaacccggg atgaccacta tgccctacaa acggagctat 12660
cggcttaagt cggcaacgac ttaaggcggt gcaacatgct cacgcttact taacttaggg 12720
tgaccactat gccctacaaa cggagcaatt ggcttaagtc ggcaacgact taaggcggtg 12780
caacatgctc acgcttactt aacttagggt gaccactatg ccctacaaac agagcaatcg 12840
gcttaagtcg gcaacgactt aaggcggtgc aacatgctca cgcttactta actcggggtg 12900
accactatgc cctacaaacg gagcaatcgg cttaagtcgg caacgactta aggcggtgca 12960
acatgctcac gcttacttaa cccgggatga ccactatgcc ctactaacgg agctatcggc 13020
taaagtcagt ggtggcttaa gccggcgcaa catactcgcg cccatataat tcaggggacg 13080
acttccatat cccgccaaca aatttcatga tcatcatgcg tcattaccac aaatttacga 13140
accaataaat tctgatacga taagagagta attatgtcat tcgaatgata aactgatgta 13200
ttttaacaaa tactcgatca tgctaaccgc gcgctcagag cacgcaaaat gtttctctat 13260
ttcgcaatgt ctttttcagg aacgaccgac gaagtaggac gattcgagga atcgggggca 13320
gcattcacgt cagcctttat gtcttcagga acaaccacgc cgggtctcct cattaagatt 13380
cgtccagcac gaatagcctt gtccatggct ttatcgcgct gggctttgag agtagtcgca 13440
gtttcttcgg caactttagc agccagccga gcagcctcta actcctgggc aatggatttc 13500
ttggaagctc ggagttcttt gatggtggca tccttcgctg atatcacttg cctaaggcgg 13560
gtcacttcgt ccgcagattc ttgcagccta caacgctgat tgtccagttc ctccattgta 13620
aagcggtgac tcctctccaa gatggtcagc gagttgttag aatcacgata caatctgtct 13680
agattgtcac gagaagcagc aaggatacgt ttttcttcct acaaacaaaa atcaactcct 13740
tcagaaatca agcaagtaat aacagcacac ggttttgtaa gttacctttt cagagtcaag 13800
ccgagcatga agagaagaac tcagggcatt ggcatcatcc aaagcagcgg agacctgatt 13860
taattcagtt tgactctgag agtacttctc ctcgaagtca gcgcaccgtt gaaccatttc 13920
agcctgctct cgggagtgtt tttcctcaag aactgcaatc tgctgagtca ttcctatcaa 13980
gaggtaatca aacaaaatga ggtcagaagg taaaacagtc cacgaacaaa ggcgaagaag 14040
aataagaaaa aagggcacta accagcgtta gttgcctcca actcggatac acgacgatga 14100
agcgacactg gattccaaca cgcaagagac gaagccactt ctggggcgga agcaccctgc 14160
gatctcagct ggctggccat cccatctacc aaagcctgat aagaagaaca gatgaacata 14220
atgacaaaag ttcacgcaac ataaagaaca agctaaaata cagcacagta cctggaggtt 14280
ggaaaagaac gaagggatcc ccaaatcagg agaaatcagc tgataaccag gcgcaaggcc 14340
accacccgaa gcagcttgca acgaaccagt aggaatcagt tcagtgcctt caacagagcc 14400
aaacgcccga tcagcgggga cgctgccctc taaaatgcct ctctggtcca aagtttgggc 14460
taccaccatg cagccagagt gtggaggtga acccacgtga acgtccatag aagtgcagga 14520
aggagaccct gctcgggcac cctcgggggc tgggtcatag ttggcactgc ccacttgagc 14580
cggatcatcc ccggcagaac cctcgggggc tgggcagtgg cttacattct tcacccgagc 14640
taagtcatcc ccagcgacac cctcgggggc tgggcatgtg tcagcaccat tcttgagatc 14700
caggctctcc gcagtaacca cctctaaggt tgacgggcct tcagccactt ccatggaacc 14760
aggacaatcc aagtcagcat cccgaccctc gagatcgcgc tctaaggtcg acgaggcacg 14820
ggatgacctc aacccagcat caggcacggc agcgcaagcc tccgttgcat catcatccac 14880
tggctctgat aacaagtcct ctgggaccat atcctcaaga gtttgatcaa agttggccag 14940
ggacagctct tgcagaccaa tgagggcaga caaagcagga gaaggaactc cactacttcc 15000
accgctggcg atgaactgcc gactgttttt ccgagttaaa ggagcttcat tttcttcctc 15060
ctcatcttcc acagtgacaa cacaagcagc acccccattg ggatcagcaa cagatggagc 15120
acccacattg ggatcagcag cagtttgggt acacccattg gggtcagcgt cagtaaggcc 15180
agttgcaggc acttcttcaa cagcaggaac taaggtaccg gcgtcctcat caaaactgga 15240
tactcgccgg aggcgtcttc tcttcttctt ttgctcatca gcagaaggct caggctgact 15300
ggttcggcta gggcgcctcg ggcgagtatt gactggtttc tggacatcca aagttgtatc 15360
aacctctgga aggggcacca ctgccaacgt accagcagga gcagcgtcgg aggaatcctc 15420
agctagcaga tcaagcatgg catttatgtc cgcatcacta gggttcaggg gcacctcaaa 15480
atggacctgc cgttcgtcat caggaatctc cccaagcgaa gcaaccaagg taccgacttc 15540
ttcagcagag gatcgcactc taaggcccaa attgccatca gtcacaggcg gatttgacac 15600
aaaaagggtg aaagctttgg gaggaggcag gttccaggcc gagtatgcca ctggagcacc 15660
aacattcgaa accttacccc tgaggatcat ttcaagtcgg cctaccaagt ccacaggagg 15720
aattctccta ttggtaaccc gagttgagtc ggctaaccct cgatacagat atgctggata 15780
ggccctgtct ttcagtggct gaatgttctt aaaaacaaag tcagtgacca cagcttcagc 15840
agttagaccc ctctctttca gcagtccaac ttcagttagc aacacacctg cctcagccac 15900
ttcctgatct gtgggagact cagtccagct cggagtgcga acgtctggct gtcttcccga 15960
ccgggggggg ggggaatttc cataattatc aactatgaac cactctagac gccatccctt 16020
aatactgtcc ttgaggggaa tctcaagata ctcagttttc cgcccgcggc gcatctccaa 16080
actggcacct ccgaccaact gatgctgtcc cccggccatc ccagggcgac aatgatacaa 16140
atacttccat aagccaaaat gcggcagcac gccaagaaag gcttcgcata agtggacgaa 16200
aatggagatt tgcagaatgg aattaggatt caaatgggtc aagttaatgt ggtagaaatc 16260
aaggaggtcg cggaaaaagg gagagatggg aaggccgagg ccgcggagaa gaaaaggagc 16320
gtaaactaca gactcgtggg tatcctctgt cgggacagta gtcccgtggc aaatccgcca 16380
agaacagagt tctcgcggag gaagaacctc gatggatacg aggtggagaa gttcagcttc 16440
ggaaatgatg gacatatggt tacctgcgaa gggcaactgg ctgttggggt cgattggagg 16500
gatcaccgca gcagacgagc tcgcagtttt cctcttgggc gccatcttga ttttcaccag 16560
cgaacagaat agggggcgaa tggcagagag gattcagaag cgggaatgca agaactaggg 16620
cacggaaagc aaaggcggct aaaagcgcag ctcttatggg atattctcga gccagatacc 16680
gtttcaaaag tgcccagtca tcacccgacg gttatttccg aaaccccagc atgccacgtg 16740
gtcatctggc agttatttcc aaaaagccga cgtgtcactt catcactcgg ttatcatcct 16800
caaaataact catgcggccg gctatcactc ggcgttgact ctaaaacgct gatttcatat 16860
tcagtcgctc ggcattacct ctaaaatgcc gacgtcacca tccagacact cggtgttgac 16920
tctaaaacgc tgattttta ttcagttgct cggcattacc actaaaaagc cgacgccgac 16980
ctccagtcac tcggcgttgc ctctaaaacg ctgatctcgt attcaatcgc tcggcattac 17040
ttctaaaatg ccgacgttaa ccttcaatca ctcggcgttg actctaaaac gctgatttta 17100
tattcagttg ctcggcatta ccactaaaaa gccgacaccg acctccagtc actcggcgtt 17160
gcctctaaaa cgctgatctc gtattcaatc gctcggcatt acttctaaaa tgccgacgtt 17220
aaccttcaat cactcggcat tgcctctaaa acgctgatct cgcattcgat cgctcggcat 17280
tacttctaaa atgccgacgt cgaccttcaa tcactcggcg ttgcctctaa agcgatgatc 17340
tcgtattcga ttgctcggta ttacttctaa aatgccgacg tcgaccttca atcgctcggc 17400
gttgcttcta aaacgccgat accgactaca agattactcg gcagctactt ctggaagcgt 17460
cagcgtgata cccaagttat tcatctactg tctcaaaaga atcagtttta taatcaagca 17520
aagcgagaca tcaagaagga gccaacgtca ttctttcatt aagggaagac aataagttta 17580
caaatcaact ctttgcgagt tgatgcttcc ctactattac tacattacat tactactact 17640
actatactat actatactac tctacattac tactacatta ttctaactac actatactaa 17700
tatctaaaga ccagcgacgc ttagccactg gccttgctgc tgctgccacc gccgccgccc 17760
ctggtgctgc ccttgctgct gccgcctctg gtgctgcccg tgctgctgcc gcctctggtg 17820
ctgcccttgc tcccgtcacc gctgccgctg cccccgccgc tgccgctgcc gtgaccatcg 17880
ccgtcgccac cgtcgtcgtc gtcgtcttcg tcgtcgtcgt catcctcgcc ctcgccgtcg 17940
tccgagtcct cctcctccga ggagaactcc gactcatccg agccctcgag cccggagcgc 18000
tcgacggccc ggatgtacgt ccagacttcc gcggcaatcc cctgggagtc gtctgaatca 18060
tcagacgacg ccgggggaga gacgggagcc agagacccct cggactcgga ggagaactcc 18120
tcctctgagt attccgagtc gccgaagtcc tccgacggag gagtcggctc gcgcttgcgt 18180
ttgttactct tgcccatggc ggaagcagac aggagagaag agaaggatgc agtaaagaac 18240
agcgaagaga tgtgaaaaaa ccagaggagc aacggcgtta tttatagaag ggaaaggcaa 18300
ccgctcacct ccaaccgtgg tcactaaaca gtcgcaaagc attcaataag cacttccacc 18360
cgtctgaaga cgcgtcagac ggctgacgcc gtttcatgca acactacacc cattgggact 18420
ccagtcaaca gcgcaaagga tatgattaca ctcgccgtcc catcacatta ctactcagaa 18480
gcagccggct aaaacactca gcgtaccaag ccgtcccttg cccacaccca ttggggggac 18540
gcccaggaat tatcagtata tttttcaaaa cggtcacatc cgtgcagggc acgcagtgaa 18600
tacctcaaga caaaaatgag atatcagtaa ggatcagagg aaagccaaat atagccagca 18660

-continued

```
atgtacaaga tatggccgac agaagcgacg tgaagactag acagagaacg tccgtcaaac  18720
gtccaatcag tcgcagaagc aaataaattg cactacctag caagatatgg atggattgca  18780
aactcggctg ctaaagacaa aatatacgct gacctctgca gcaaaatatt gatgacataa  18840
tgctgacctc caaagcataa tgcaaatagc ttcatgccaa tttttacaaa cgaaagaaag  18900
accttcgaat ggattatcct caaaaatcca tttgaaggtc gggggctaca cccattgggt  18960
gcacctccgg tgcacccccct ggattatcat tccaaaccga gatagtgccg acttctaagg  19020
cacgggacaa gattaaaata ccaatcctcg accaagatgc aggagcacaa atggagataa  19080
tttctgggga agaccttcga gtagattatt ttctaaaaat ctactcaaag gtcgggggct  19140
acacccattg ggtgcacctc cggtgcaccc aatgaagttc agaatcctgc aaatcgaaat  19200
gtcgacctct aaggcacaag cacgaaacta agcttcggtc aaatgagcga tcggagcaag  19260
agaagacagc aggaagtcat tttttggacc tgggatcttt gggttgatta cctctaaatt  19320
aacccaaaga tcgggggctt gtggtggata gatatccccc gggtccacta agggagtaaa  19380
agacctcacg aaaggcccaa gggcccaata aatggtaagg tcattcttcc gtgggcctgg  19440
ggagaaacaa ccaacaaaac agagaagacg taagaccgga ttggtgcaaa cccggacgac  19500
ccacaacgtc gaacgagtaa atcgcaacag agacccgact ttcccgcgct ggagccccca  19560
tgcaacggag ccatgcaagg ataagtcggc gagggttacg tagggataaa ctcaagaggt  19620
tcactacctt ttagctactt gttgttatca tatccacgtg tactgcccca cagtcgagta  19680
tataaggcct agggggcacc ccttcagaac gatcgaccct atcttactta gccccccaca  19740
gcaactctct gtgtcttcaa tccagagagc cctcttgtaa ccacgctcac atactcaccg  19800
ggacgtaggg tgttacgcat ctctaagcgg cccgaacctg taaatcttgt ccactgtccc  19860
tcgtgtgatc ggcacgaacc gttttgctac agtcgtcgac actgtcctac tcctagaaac  19920
accttgaggg gcaaccccgg gtgtgcggtc ggacccaaaa caccgacact agcacacgtg  19980
gaccaattga aagcccccac cttgctctcg ttcgtcgctc gttcacgcca gcgcgtcacc  20040
cacccactgc gccctctcat cctccttgcc cgagaacgtg cttcagagca ggcgagagtg  20100
gggcgatatc gcccgaggga tgcatctctc cctcctctca ccccgggcca ggctacaaca  20160
gcccccctact gcccaaccac tcgccctcgt tggcaccaac catactacca caacactcca  20220
atgcacaatt tttaatgtta gcctatattc accttagcat cacatcatat ttcttctaca  20280
aaattatatt tagaacgaaa cacgacgttt tgcttggaat tttttcgatg gagtagaaaa  20340
aatataatcc aaacaaatta cgtaaaatac gtaaaataaa aaatatagct cctaaaagtt  20400
aaaattactc atcattatca ccctcctcgt tttcttcctc gtctagtttt aattgcgtga  20460
tcaatttttt tagaaccaac ctagaccctc ctcataccag tggtggattg tttcagtaac  20520
ttggtgaact ggtcgtacaa ttttttgatt ggtttctcgt gtcactaacc ttgaataatt  20580
gcttcgttat ggttttcttc tggacaaggg actcattggt actcattcct ggtgcctaac  20640
ccttgttttg tgctcttgcc caatcacgac caatagggta tggtggtttg gcactatcgg  20700
acgatgtaga gttataatca ccctccacgt tgaggcaaga tcattttctc tcattgctag  20760
agtttgaatc accatgtcac gtgcaccact tgaattgatg atgaagagca cgccattagt  20820
ttcatcgagc ctgttgtgga agagtagcat aacattattt gatctgctcg gtaggttata  20880
cgtggccgat atttggcacc aaaaggtcaa acatttttgt tgtttccctc aaatcttttt  20940
tggtctcaaa aaggtcaaac ctttttttgg ctttccatcc ctgtccccac gaacagtcac  21000
gagtaacttt ttctcccatc cccgttcgtg tgggggaatt tatccccatg ggaaatctat  21060
```

ccctgttaga gaatgtaata tttttggggc aaggtcaaat tgataaacca atataaattg 21120
aacaaataag atttaaaatt acaagagaaa tctactttag agttgagctt gctattttat 21180
aaaaggctat gtgttgaatt tttattataa ctttaacata tcaatggatt gattttagat 21240
taagagaagt tcgtgggggc ggatatgcga ggaacaggga tggggaatgg ttcaccattc 21300
tcgtcccacg aacacgacaa ggactaaatt tttctcgttt caatctccgt ggggactaaa 21360
ttacacctat ccccgtccac taataaaggg ataccccgcg gggaattagg gatcacgtcc 21420
ccatttcaca tttttagact tctcacattg agcaacaaca aaacatttta tgaattagta 21480
gccattttac ttatctaaaa caattactat tgaatcttaa tcattttgtg caaaataaag 21540
aatgaactaa attttgggtc gggtgtgggt cacccgtagg ttgaaataaa aactcgcacc 21600
cacactcgtg aaactttggg tcagatgagg gttacacccg cggattaaaa tctctaccca 21660
tacccacacc cgtcagatcg agtacccaaa gattttgggt ttgcgggtta aattgtcatc 21720
cctagacacg agtgtgctgg aggatttgga agtttcgcaa tgcgtactta ccaagtgttt 21780
ggttctatgg attaaagttt agcatgtgtc gcattagatg attgaatgcc tattatgagt 21840
attaaatatt gtctgattat taatcaaatt acacaagtga aggctaaaca actagacaaa 21900
tttattaagc ctaattaatc tatgattagc aaatgtttat agtagcagca tcttagtgaa 21960
tcatgaacta attaggttta ataggttcgt cttaacgttt agttcttatc tatgtaatta 22020
attttataag taaactatat ttaatattcc taattagtct ccggatataa catagactaa 22080
aatttagtca gtggtgctgc tgctggctcc ttttcatttc atccgacata atgttttcct 22140
cccaatttat tgtgttgttt tgtttgtgct ttaaaaatga cttgtcctct gcttgctgta 22200
tcaaggtcgt gatgtgtgct taacttattc ccttccttcc tagctgccct tagcatttat 22260
ataggggtat ttggttacat ggactaaagt ttagtttagt ccatgtccaa ttataaaact 22320
aattacataa ctgaatacta aaataccaaa atacgagaaa aattattaaa cctaattaat 22380
ttattattag caatgtttat tgtaacatca cataagcaaa gcatagactg atttagttta 22440
ataggttcgt cttatcattt agtcttgatc tgtataatta gggtatgttt ggttcactgc 22500
ctaacttacc acactttgcc taacttttct gcctaaggtt agttcttcaa tttgaacgac 22560
taaccttagg caaagtatgg cgtagttagc cacgaaccaa acagtccctt agttttgtaa 22620
ttaaactata tttactattt ttaactagta tccaaacatt aaatgtgaca tggattaaaa 22680
tttagttagt gactttaggc ttttagagtt gagttagttg tagcttggtt tagttatttg 22740
tttgttctct tgcgtttatt taggacctct ctataatgtt ttatcacctt aatacaaatt 22800
aaaatacgca gctcttgtgt attgcaggcg tgtgtgttcc tatattttta ggctcaatta 22860
tgaaggaaat tattctcagc gagcatataa ccgttttgga ggtaaaatga actaaaagca 22920
tataggcctg cctgtttgca taagtacacc ctccgtctaa aaaagaataa aaatctcatt 22980
tcttgatgag tcaaaaaagt tcaaatttaa gaaaatatat gttacgacac gaatatttat 23040
aatgtgtaat aagtaccgct agattaattt taaaataaaa ttttcataat aaacctattt 23100
gaagatacaa gtattggtac tatttctaat aaatctaatc aaactggtgt tatatctttt 23160
ggaacaaatt tgtgctttat gtttctggtt gacgtgaatc agcttaatct tgacgaaatc 23220
taacattgtc ttttgttcgt tggcatacag gatcaacaaa aaggagagaa gcagcatcta 23280
ttgttggtaa gagcctatag tcaataccca tgttcatttc gtctaaaaga gcagaagaaa 23340
agcatatgat gaattattgc catgtcatgt ttaaaataca gaattctcaa aaacaaaaac 23400
aaaaaaaaaa acttggaatc cactaaccac tgatagcatt gtagaaaatt tcatcctccc 23460
tttgggcaat acactgatga gtttacatgc tgactagtgg tgcatttgtt ctttgccaat 23520
tgagttttta gaatgctttg cagctgaatt cacttgtgat gttttttttt gtgtgtgatg 23580
caggtgctgt tgccgttgca ttcctgtgtc tagtcattct cacatgcttc ttggcttgta 23640
gacattgttc gctgcccttc aaatcgaaga acaaaccagg gacaaggatt gagtccttcc 23700
tacagaagaa cgagagtagt atacatccga aaagatacac ctacgcggac gtgaaaagaa 23760
tgacaaaatc cttcgctgtg aagctaggcc aaggtgggtt tggtgctgta tacaaaggca 23820
gcctccacga tggccgacag gtagcagtca agatgctgaa ggacacccaa ggtgacggcg 23880
aggaattcat gaacgaggtg gctagcatca gcaggacttc tcatgtcaac gtcgtgacac 23940
ttctagggtt ttgcttgcaa gggtcgaaaa gagcactgat ctacgagtac atgcccaatg 24000
gttcgctcga aaggtatgcc ttcaccggtg acatgaacag tgagaatttg ctaacctggg 24060
aaagactatt tgacatagcg attggcacgg ccagagggct cgaataccta caccggggat 24120
gcaacactcg gatcgtgcat tttgacatca agccacacaa catcctgtta gaccaggatt 24180
tctgccctaa gatctctgac tttggactgg ccaagctatg tctgaacaaa gagagcgcta 24240
tctccattgc tggcgcaaga gggacgatag ggtatatcgc cccggaggtc tactcaaagc 24300
aatttggaac gatcagcagc aagtctgatg tctatagcta tgggatgatg gtccttgaga 24360
tggttggagc aagggacagg aatacaagcg cagatagtga ccatagcagc caatatttcc 24420
ctcagtggct ttatgaacat ttggacgact attgtgttgg tgcttccgag attaatggtg 24480
agaccacaga gctcgtgagg aagatgatag ttgtaggtct gtggtgcata caagtgattc 24540
cgactgatcg accaacaatg acgagagtcg tcgagatgtt ggaaggaagc acaagtaatc 24600
tagagttgcc acccagagtt ctcttgagct ga 24632

<210> SEQ ID NO 2
<211> LENGTH: 2004
<212> TYPE: DNA
<213> ORGANISM: Artificial Sequence
<220> FEATURE:
<223> OTHER INFORMATION: cDNA derived from Ht2 gene (SEQ ID NO: 1)

<400> SEQUENCE: 2
atggctgctc acctaccacg cctccccgtc ctcctcctcg tcctcctcgc tgcccatgtc 60
gtctccacct ccgcccatgc cgagcctcct cttccgagcc cttacagcac ctccgcccat 120
ggcgagcctc ctcttccgag cacttacaac gtctccatgt gctcggaatc gttctggtgc 180
ggcggcgtcg aaatccgcta cccgttctat cttgccaacg caaccgccga ctacagcggg 240
agctactact cctgcggcta caccgacttg agcgtttcct gcaaactcga ggtcgagggg 300
ccgacgacga catggacccc taccatccgt ctcggcggcg acaactacac cgtcaagaac 360
atcttgtacg actatcatac catctcactg gcggacagcg atgtgctcgg aggcggcgag 420
tgccccgtcg tccaccacaa cgtcagcttc gacgagacgt ggctgcacaa ccccagcgcc 480
ttcgacaacc tcaccttctt cttcggatgc cactgggggc cacgcgatac actgcctgaa 540
tttgccggca acaacatcag ctgcgccggg ttcagtactc cagctatcag cggtggaggc 600
tccttcgtgt tcaagcctga agatcttgac gaacatgcgg agcaggagtt ggcttcacac 660
tgcgacgagg ttttctccgt gccagtgaga agcgaggctc tgcagcaggc gatcgtcagc 720
aacctcagcc tcggggacgg gtacggcgag ctgcttaggc aggggatcga gttggaatgg 780
aaacggacat cggaggatca gtgtggccag tgcgaggaat cgggctccgg cggacggtgc 840

```
gcctacagcc agaagagaga attccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020

tcgctgccct tcaaatcgaa gaacaaacca gggacaagga ttgagtcctt cctacagaag   1080

aacgagagta gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaagacta   1440

tttgacatag cgattggcac ggccagaggg ctcgaatacc tacaccgggg atgcaacact   1500

cggatcgtgc attttgacat caagccacac aacatcctgt tagaccagga tttctgccct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

acgatcagca gcaagtctga tgtctatagc tatgggatga tggtccttga gatggttgga   1740

gcaagggaca ggaatacaag cgcagatagt gaccatagca gccaatattt ccctcagtgg   1800

ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggaa gcacaagtaa tctagagttg   1980

ccacccagag ttctcttgag ctga                                          2004
```

<210> SEQ ID NO 3
<211> LENGTH: 667
<212> TYPE: PRT
<213> ORGANISM: Zea mays

<400> SEQUENCE: 3

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160
```

```
Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
```

-continued

```
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 4
<211> LENGTH: 1487
<212> TYPE: DNA
<213> ORGANISM: Zea mays

<400> SEQUENCE: 4

aagtgaacct caccatcgac atcgtctggc tacgactcgc accctccggc tccaacatca      60

cattcctcta caattgcaag aagaacatta gagcatctcc agcaggtcgt gtaaatagtc     120

gtgcaaaata caatttgtac tatagattac actatttgca gtgtgaagtt taagatagag     180

agtaggataa agagtctgct ggacatatta ccctgtcctc tgtcgtggaa ctgagtgggt     240

gcccacagca acaagaagat agaagtaggt cgtacgtgtt gtcgggtggc gggatcatgt     300

gtgctgagac gtacgtatac atgtccaaat aggcaggtcg ggccgactcg gcccgagccc     360

gactaagctc ggcacggatt atgatcgtgc tggcctgacc cagattagca agcaggtcgt     420

gtcgtgcctg cccacgggta tcgagcgagg cccagacacg acacgctaag gtattaaccg     480

tgccgaaccg acccacggcc cgacgggcca aacaggtcta taatagtata tgacgtttaa     540

atgtaaaaaa tatattaaaa tatacataac gaaggtttaa accatattta ttagctctaa     600

acacctattt acacccacat caccaacaaa acaaatatgt ttactgtatt ttatactata     660

tattaagtat aatgtatgta tttgtattaa aaaaatagga acaaaattaa aaatgggtcg     720

tggcgtgttt agcctctcgt ggcgcgcgta gacccagaca caacctagtc accagaccgg     780

gccaaccagt acctgagttt cggaccgccc gaccggccgg tacaagcacg ggtgcgaggg     840

cgtggtggtg gcgccgccgg tgctggatgt acacaagaag gggggaagag aagcccgggc     900

accaccggcg gtccgcctcc ggaacggatc gctccgtcgg ttgctgcagg gcgggttcga     960

gctgaactac gacactcact ccgagcagtg cgtccgatgc tagggctccg gcggatggtg    1020

tggctaccag cgcgaggaga cgcccgccgg cgggatgaca ttcgcctgtt tctgcgacgg    1080

cggccagacc acgggccgat gcggtgccgg tatgtctttt ttttttcttc gaacaaggtg    1140

tggcatgtgt tctaccgttt caactagtaa atgattacat tgagctaggc agctagccac    1200

acattttctt gaatgatttt ctttgatgaa cctgctgttt gcttttatga cgtgaacaac    1260

ggggcctgca agctgccaca tacctaggga gactagttcg tgaccttctt tacacgtctt    1320

ctctactcgc cactgggagt tgacgccgct cggtcgtccc actttgtgac gttcaaccag    1380

agtctagaga tgtaattctc tgcgaataca ggactagttg gagctaacaa cgcagcttga    1440

cgagggtgaa cccagctcca cctcgtctac cacgtcttct cctcgcc                  1487


<210> SEQ ID NO 5
<211> LENGTH: 1979
<212> TYPE: DNA
```

<213> ORGANISM: Zea mays

<400> SEQUENCE: 5
caaagcgtag atatttttcc tatcaaatgt tgcttccagg tcacataaat gcaaatattt 60
gtggagacgt acgagtgccc attaacctca tacactgtat ctgtatgaca aaagtcccac 120
gactcactgg acgcggaaat gtcgcttgac tacgccaatt ttctaaaaag attggcagca 180
attaattggg cttatagcgg taactttggt tcgcattagt tgtaggacta gagttgaata 240
tcgatccaac tcgccgtggc acggtcgagc tcaagctagc tccgctcagc tcattaaaga 300
attcagccag agaatcagct catgtcgttt acgagtttga gctggctcgt ttagctcgtg 360
aatcataaca aaaacaacat gcacatatat acaataatat aatcaatact agttaattct 420
agactagttt aacactagaa aagagtaata atactcataa tttcacatac aatatcaatc 480
taacaccaaa ttaacatatt tcgtcacttg ttagttcatc caatcaagtg taggctttgc 540
tttactgaca aatggttgct cgttcgagct agcgatcgag cttgcttgtt aataaaccga 600
gttgagatgc tagctcaatt tgtgacaaaa ttaaaataag ccgagtcgaa acaagttaag 660
cttatgacga ttcgagcaag ctcacgagcc acaagtatta ttttttttcc agtactacct 720
aagagcatga cgtcggtatg ttttctttac cgacgatggt ggtgattttt atttcgcaat 780
gcattggaaa actggcgaca tgagttcaaa cgcaatgcaa cacactacct cccacgagct 840
ggtttttgtg cgagacagta aagaagcaaa caaatctaac cagccaaatc cttggccggg 900
caccacagac cacggcgaac aactccccct ctctcttccg tccatcttat ttcttcgccg 960
tgcgtggctc tgcttgcgcc gacggccgac ggatgagcta ctaggattac ggctagcaac 1020
tcgggacggg caccttgcac gcggtgaaca ccctgcgctt gtgcctggcg tcgacgaggc 1080
gcttcaggct ggcgtcgtcc ttgtaccggc acaggcagcc gggcccgtgg gacatgagct 1140
tggcgcagca ggcggccgtg ggcgacgcct tccccgcgaa cgcgctcgcg caggggctca 1200
gctgcgtcac gtcgcacggc gccagggccg agaagtcgcc cgcggcgcgg ccggcgagga 1260
ggaggaggac gctggccagc accgcggcga ggaagagcgc ggccggcctc atcgtcccga 1320
ccgacgatag atggtgtcac tggatatata ggtcggaccg gactagctgc gagtggacta 1380
gctgggtggg aagccacgta cgagcgtcgt cgggagcttt tttgtaggcg ccgattagtt 1440
gtgtgctatg gcggattatt agcccggcgg aaggtgaggt gagtcacggc gtaagcatgc 1500
ggcacagtcg agcgagccca gcagtgtccg ttaggttagg tgaagcacgc tgcacgcccg 1560
gtggaagggc tcaccatttg atgctttctc atcgctcatc agtcatcact atgattctag 1620
agaatatatc tagtacatat ggtgtacata ttaaatgatc atcacttatt ttagatctaa 1680
tgtctctagt tgtttgatat attttgctaa tgacaccctc caacgttggt gtgtagtggt 1740
ggaaggtgtt atttgtaaat taaatgatca actagagacg ttagatctaa aataagtggt 1800
gatgatttaa tatatgcacc atgtacacca atcttctatg tgcaccagat atgtcctcat 1860
gattctaaca gagaggtacg tgcgcatcct gcgaacgtat tgttgagttt tttttaagtt 1920
caacacatgg ttacgtcatg atcctatact attctcgaat atagatgaac aaacgggcc 1979

<210> SEQ ID NO 6
<211> LENGTH: 920
<212> TYPE: DNA
<213> ORGANISM: Zea mays

<400> SEQUENCE: 6
atggctgctc acctaccacg cctccccgtc ctcctcctcg tcctcctcgc tgcccatgtc 60

```
gtctccacct ccgcccatgc cgagcctcct cttccgagcc cttacagcac ctccgcccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga attccttggc tgcttctgca gcggagggaa ggcgggcaac    900

ccgttctgca aaccatcaag                                                920


<210> SEQ ID NO 7
<211> LENGTH: 37
<212> TYPE: DNA
<213> ORGANISM: Zea mays

<400> SEQUENCE: 7

atcaacaaaa aggagagaag cagcatctat tgttggt                              37


<210> SEQ ID NO 8
<211> LENGTH: 1047
<212> TYPE: DNA
<213> ORGANISM: Zea mays

<400> SEQUENCE: 8

gctgttgccg ttgcattcct gtgtctagtc attctcacat gcttcttggc ttgtagacat     60

tgttcgctgc ccttcaaatc gaagaacaaa ccagggacaa ggattgagtc cttcctacag    120

aagaacgaga gtagtataca tccgaaaaga tacacctacg cggacgtgaa aagaatgaca    180

aaatccttcg ctgtgaagct aggccaaggt gggtttggtg ctgtatacaa aggcagcctc    240

cacgatggcc gacaggtagc agtcaagatg ctgaaggaca cccaaggtga cggcgaggaa    300

ttcatgaacg aggtggctag catcagcagg acttctcatg tcaacgtcgt gacacttcta    360

gggttttgct tgcaagggtc gaaaagagca ctgatctacg agtacatgcc caatggttcg    420

ctcgaaaggt atgccttcac cggtgacatg aacagtgaga atttgctaac ctgggaaaga    480

ctatttgaca tagcgattgg cacggccaga gggctcgaat acctacaccg gggatgcaac    540

actcggatcg tgcattttga catcaagcca cacaacatcc tgttagacca ggatttctgc    600

cctaagatct ctgactttgg actggccaag ctatgtctga acaaagagag cgctatctcc    660

attgctggcg caagagggac gatagggtat atcgccccgg aggtctactc aaagcaattt    720

ggaacgatca gcagcaagtc tgatgtctat agctatggga tgatggtcct tgagatggtt    780

ggagcaaggg acaggaatac aagcgcagat agtgaccata gcagccaata tttccctcag    840

tggctttatg aacatttgga cgactattgt gttggtgctt ccgagattaa tggtgagacc    900
```

```
acagagctcg tgaggaagat gatagttgta ggtctgtggt gcatacaagt gattccgact    960

gatcgaccaa caatgacgag agtcgtcgag atgttggaag gaagcacaag taatctagag   1020

ttgccaccca gagttctctt gagctga                                       1047
```

```
<210> SEQ ID NO 9
<211> LENGTH: 2004
<212> TYPE: DNA
<213> ORGANISM: Artificial Sequence
<220> FEATURE:
<223> OTHER INFORMATION: cDNA of HtN1

<400> SEQUENCE: 9

atggctgctc accagcctca cctctccgtc ctcctcctcg tcctcctcgc tgcccatgtc     60

gtctccacct ccgcccatgg cgagcctcct cttccgagcc cttacaacac ctccgcccat    120

ggcgagcctc ctcttccgag cacttacaac gcctccatgt gctcgtcgtt ctggtgtggc    180

ggcgtcgaga tccgctaccc gttctatctt gccaacgcaa tcgccgacta cagcgggagc    240

tactactcct gcggctacac cgacttgagc gtttcctgcg aactcgaggt cgaggggtcg    300

ccgacgacct ggacccctac catccgtctc ggcggcggcg actacaccgt caagaacatc    360

tcctacctct acgaccagca gaccatctca ctggcggaca gagatgtgct cggaggcggc    420

ggctgccccg tcgtccgcca caacgtcagc ttcgacgaga cgtggctgca cctgcacaac    480

gccagcgcct tcgacaacct caccttcttc ttcggatgcc actgggggcc acggaataca    540

ccgcctgaat ttgccgacta caacatcagc tgcgccgggt tcaatactcc aactatcagc    600

ggtggaaggt ccttcgtgtt caagactgga gatcttgacg aacaagagga gcaggagttg    660

gctttacact gcgacgaggt ttctccgtg ccagtgagaa gagatgctct gcaggcgatc     720

gtcagcaact tcagcctcac acgggacggg tacggcgagg tgcttaggca ggggttcgag    780

ttggaatgga atcggacatc ggaggatcag tgtggccggt gcgagggatc gggctccggc    840

ggatggtgcg cctacagcca gaagagagaa ttcctgggct gcttgtgcag cggagggaag    900

gtgggcagcc cgttctgcaa accatcgaga tcaaaaagga aagaaggacc tattgttggt    960

gctgttgccg ttgcattcct gtgtctagtc attctcacat gcttcttggc ttgtagacat   1020

ggttcgctgc ccttcaaatc ggagaacaaa ccagggacaa ggattgagtc cttcctacag   1080

aagaacgaga gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaaggcta   1440

tttgacatag caattggcac ggccagaggg ctcgaatacc tacaccgggg atgcaacact   1500

cggatcgtgc attttgacat caagccacac aacatcctgt tagaccagga tttctgtcct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

ataataagca gcaagtctga tgtctatagc tatgggatga tggtccttga gatggttgga   1740

gcaagggaca ggaatacaag cgcagatagt gaccatagca gccaatattt ccctcagtgg   1800

ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920
```

cgaccaacaa tgacgagagt cgtcgagatg ttggaaggga gcacaagtaa tctagagttg 1980
ccacccagag ttctcttgag ctga 2004

<210> SEQ ID NO 10
<211> LENGTH: 667
<212> TYPE: PRT
<213> ORGANISM: Zea mays

<400> SEQUENCE: 10

Met Ala Ala His Gln Pro His Leu Ser Val Leu Leu Leu Val Leu Leu
1 5 10 15

Ala Ala His Val Val Ser Thr Ser Ala His Gly Glu Pro Pro Leu Pro
20 25 30

Ser Pro Tyr Asn Thr Ser Ala His Gly Glu Pro Pro Leu Pro Ser Thr
35 40 45

Tyr Asn Ala Ser Met Cys Ser Ser Phe Trp Cys Gly Gly Val Glu Ile
50 55 60

Arg Tyr Pro Phe Tyr Leu Ala Asn Ala Ile Ala Asp Tyr Ser Gly Ser
65 70 75 80

Tyr Tyr Ser Cys Gly Tyr Thr Asp Leu Ser Val Ser Cys Glu Leu Glu
85 90 95

Val Glu Gly Ser Pro Thr Thr Trp Thr Pro Thr Ile Arg Leu Gly Gly
100 105 110

Gly Asp Tyr Thr Val Lys Asn Ile Ser Tyr Leu Tyr Asp Gln Gln Thr
115 120 125

Ile Ser Leu Ala Asp Arg Asp Val Leu Gly Gly Gly Gly Cys Pro Val
130 135 140

Val Arg His Asn Val Ser Phe Asp Glu Thr Trp Leu His Leu His Asn
145 150 155 160

Ala Ser Ala Phe Asp Asn Leu Thr Phe Phe Phe Gly Cys His Trp Gly
165 170 175

Pro Arg Asn Thr Pro Pro Glu Phe Ala Asp Tyr Asn Ile Ser Cys Ala
180 185 190

Gly Phe Asn Thr Pro Thr Ile Ser Gly Gly Arg Ser Phe Val Phe Lys
195 200 205

Thr Gly Asp Leu Asp Glu Gln Glu Glu Gln Glu Leu Ala Leu His Cys
210 215 220

Asp Glu Val Phe Ser Val Pro Val Arg Arg Asp Ala Leu Gln Ala Ile
225 230 235 240

Val Ser Asn Phe Ser Leu Thr Arg Asp Gly Tyr Gly Glu Val Leu Arg
245 250 255

Gln Gly Phe Glu Leu Glu Trp Asn Arg Thr Ser Glu Asp Gln Cys Gly
260 265 270

Arg Cys Glu Gly Ser Gly Ser Gly Gly Trp Cys Ala Tyr Ser Gln Lys
275 280 285

Arg Glu Phe Leu Gly Cys Leu Cys Ser Gly Gly Lys Val Gly Ser Pro
290 295 300

Phe Cys Lys Pro Ser Arg Ser Lys Arg Lys Glu Gly Pro Ile Val Gly
305 310 315 320

Ala Val Ala Val Ala Phe Leu Cys Leu Val Ile Leu Thr Cys Phe Leu
325 330 335

Ala Cys Arg His Gly Ser Leu Pro Phe Lys Ser Glu Asn Lys Pro Gly
340 345 350

```
Thr Arg Ile Glu Ser Phe Leu Gln Lys Asn Glu Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Ile Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```

<210> SEQ ID NO 11
<211> LENGTH: 2004
<212> TYPE: DNA
<213> ORGANISM: Artificial Sequence
<220> FEATURE:
<223> OTHER INFORMATION: cDNA of RLK1 allele from PH99N

<400> SEQUENCE: 11

```
atggctgctc accagcctca cctctccgtc ctcctcctcg tcctcctcgc tgcccatgtc     60

gtctccacct ccgcccatgg cgagcctcct cttccgagcc cttacaacac ctccgcccat    120

ggcgagcctc ctcttccgag cacttacaac gcctccatgt gctcgtcgtt ctggtgtggc    180

ggcgtcgaga tccgctaccc gttctatctt gccaacgcaa tcgccgacta cagcgggagc    240

tactactcct gcggctacac cgacttgagc gtttcctgcg aactcgaggt cgaggggtcg    300
```

```
ccgacgacct ggacccctac catccgtctc ggcggcggcg actacaccgt caagaacatc    360

tcctacctct acgaccagca gaccatctca ctggcggaca gagatgtgct cggaggcggc    420

ggctgccccg tcgtccgcca caacgtcagc ttcgacgaga cgtggctgca cctgcacaac    480

gccagcgcct tcgacaacct caccttcttc ttcggatgcc actgggggcc acggaataca    540

ccgcctgaat ttgccgacta caacatcagc tgcgccgggt tcaatactcc aactatcagc    600

ggtggaaggt ccttcgtgtt caagactgga gatcttgacg aacaagagga gcaggagttg    660

gctttacact gcgacgaggt tttctccgtg ccagtgagaa gagatgctct gcaggcgatc    720

gtcagcaact tcagcctcac acgggacggg tacggcgagg tgcttaggca ggggttcgag    780

ttggaatgga atcggacatc ggaggatcag tgtggccggt gcgagggatc gggctccggc    840

ggatggtgcg cctacagcca gaagagagaa ttcctgggct gcttgtgcag cggagggaag    900

gtgggcagcc cgttctgcaa accatcgaga tcaaaaagga aagaaggacc tattgttggt    960

gctgttgccg ttgcattcct gtgtctagtc attctcacat gcttcttggc ttgtagacat   1020

ggttcgctgc ccttcaaatc ggagaacaaa ccagggacaa ggattgagtc cttcctacag   1080

aagaacgaga gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaaggcta   1440

tttgacatag caattggcac ggccagaggg ctcgaatacc tacaccgggg atgcaacact   1500

cggatcgtgc attttgacat caagccacac aacatcctgt tagaccagga tttctgtcct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

ataataagca gcaagtctga tgtctatagc tatgggatga tggtccttga gatggttgga   1740

gcaagggaca ggaatacaag cgcagatagt gaccatagca gccaatattt ccctcagtgg   1800

ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggga gcacaagtaa tctagagttg   1980

ccacccagag ttctcttgag ctga                                          2004
```

<210> SEQ ID NO 12
<211> LENGTH: 667
<212> TYPE: PRT
<213> ORGANISM: Zea mays

<400> SEQUENCE: 12

```
Met Ala Ala His Gln Pro His Leu Ser Val Leu Leu Leu Val Leu Leu
1               5                   10                  15

Ala Ala His Val Val Ser Thr Ser Ala His Gly Glu Pro Pro Leu Pro
            20                  25                  30

Ser Pro Tyr Asn Thr Ser Ala His Gly Glu Pro Pro Leu Pro Ser Thr
        35                  40                  45

Tyr Asn Ala Ser Met Cys Ser Ser Phe Trp Cys Gly Gly Val Glu Ile
    50                  55                  60
```

```
Arg Tyr Pro Phe Tyr Leu Ala Asn Ala Ile Ala Asp Tyr Ser Gly Ser
65                  70                  75                  80

Tyr Tyr Ser Cys Gly Tyr Thr Asp Leu Ser Val Ser Cys Glu Leu Glu
                85                  90                  95

Val Glu Gly Ser Pro Thr Thr Trp Thr Pro Thr Ile Arg Leu Gly Gly
            100                 105                 110

Gly Asp Tyr Thr Val Lys Asn Ile Ser Tyr Leu Tyr Asp Gln Gln Thr
        115                 120                 125

Ile Ser Leu Ala Asp Arg Asp Val Leu Gly Gly Gly Gly Cys Pro Val
    130                 135                 140

Val Arg His Asn Val Ser Phe Asp Glu Thr Trp Leu His Leu His Asn
145                 150                 155                 160

Ala Ser Ala Phe Asp Asn Leu Thr Phe Phe Phe Gly Cys His Trp Gly
                165                 170                 175

Pro Arg Asn Thr Pro Pro Glu Phe Ala Asp Tyr Asn Ile Ser Cys Ala
            180                 185                 190

Gly Phe Asn Thr Pro Thr Ile Ser Gly Gly Arg Ser Phe Val Phe Lys
        195                 200                 205

Thr Gly Asp Leu Asp Glu Gln Glu Glu Gln Glu Leu Ala Leu His Cys
    210                 215                 220

Asp Glu Val Phe Ser Val Pro Val Arg Arg Asp Ala Leu Gln Ala Ile
225                 230                 235                 240

Val Ser Asn Phe Ser Leu Thr Arg Asp Gly Tyr Gly Glu Val Leu Arg
                245                 250                 255

Gln Gly Phe Glu Leu Glu Trp Asn Arg Thr Ser Glu Asp Gln Cys Gly
            260                 265                 270

Arg Cys Glu Gly Ser Gly Ser Gly Gly Trp Cys Ala Tyr Ser Gln Lys
        275                 280                 285

Arg Glu Phe Leu Gly Cys Leu Cys Ser Gly Gly Lys Val Gly Ser Pro
    290                 295                 300

Phe Cys Lys Pro Ser Arg Ser Lys Arg Lys Glu Gly Pro Ile Val Gly
305                 310                 315                 320

Ala Val Ala Val Ala Phe Leu Cys Leu Val Ile Leu Thr Cys Phe Leu
                325                 330                 335

Ala Cys Arg His Gly Ser Leu Pro Phe Lys Ser Glu Asn Lys Pro Gly
            340                 345                 350

Thr Arg Ile Glu Ser Phe Leu Gln Lys Asn Glu Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
```

```
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Ile Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 13
<211> LENGTH: 2001
<212> TYPE: DNA
<213> ORGANISM: Artificial Sequence
<220> FEATURE:
<223> OTHER INFORMATION: cDNA of RLK1 allele from PH26N

<400> SEQUENCE: 13

atggctgctc acctaccacg cctccccgtc ctcctcctcg tcctcctcgc tgctcatgtc      60

gtctccacct ccgcccatgc cgagcctcct cttccgagcc cttacagcac ctccgcccat     120

ggcgagcctc ctcttccgag cacttacaac gtctccatgt gctcggaatc gttctggtgc     180

ggcggcgtcg aaatccgcta cccgttctat cttgccaacg caaccgccga ctacagcggg     240

agctactact cctgcggcta caccgacttg agcgtttcct gcaaactcga ggtcgagggg     300

ccgacgacga catggacccc taccatccgt ctcggcggcg acaactacac cgtcaagaac     360

atcttgtacg actatcatac catctcactg gcggacagcg atgtgctcgg aggcggcgag     420

tgccccgtcg tccaccacaa cgtcagcttc gacgagacgt ggctgcacaa ccccagcgcc     480

ttcgacaacc tcaccttctt cttcggatgc cactgggggc cacgcgatac actgcctgaa     540

tttgccggca acaacatcag ctgcgccggg ttcagtactc cagctatcag cggtggaggc     600

tccttcgtgt tcaagcctga agatcttgac gaacatgcgg agcaggagtt ggcttcacac     660

tgcgacgagg ttttctccgt gccagtgaga agcgaggctc tgcagcaggc gatcgtcagc     720

aacctcagcc tcggggacgg gtacggcgag ctgcttaggc aggggatcga gttggaatgg     780

aaacggacat cggaggatca gtgtggccag tgcgaggaat cgggctccgg cggacggtgc     840

gcctacagcc agaagagaga attccttggc tgcttgtgca gcggagggaa ggcgggcaac     900

ccgttctgca aaccatcaag atcaaaaagg aaagaagcat ctattgttgg tgctgttgcc     960

gttgcattcc tgtgtctagt cattctcaca tgcttcttgg cttgtagaca tggttcgctg    1020
```

```
cccttcaaat cggagaacaa accagggaca aggattgagt ccttcctaca gaagaacgag   1080

agtatacatc cgaaaagata cacctacacg gacgtgaaaa gaatgacaaa atccttcgct   1140

gtgaagctag gccaaggtgg gtttggtgct gtatacaaag gcagcctcca cgatggccga   1200

caggtagcag tcaagatgct caaggacacc caaggtgacg gcgaggaatt catgaacgag   1260

gtggctagca tcagcaggac ttctcatgtc aacgtcgtga cacttctagg gttttgcttg   1320

caagggtcga aaagagcact gatctacgag tacatgccca atggttcgct cgaaaggtat   1380

gccttcaccg gtgacatgaa cagtgagaat ttgctaacct gggaaaggct atttgacata   1440

gcaattggca cggccagagg gctcgaatac ctacaccggg gatgcaacac tcggatcgtg   1500

cattttgaca tcaagccaca caacatcctg ttagaccagg atttctgtcc taagatctct   1560

gactttggac tggccaagct atgtctgaac aaagagagcg ctatctccat tgttggcgca   1620

agagggacga tagggtatat cgccccggag gtctactcaa agcaatttgg aacaatcagc   1680

agcaagtctg atgtctatag ctatgggatg atggtccttg agatggttgg agcaagggaa   1740

aggaatacaa gcgcaagcgc agatagtgac catagcagcc aatatttccc tcagtggatt   1800

tatgaacatt tggacgacta ttgtgttggt gcttccgaga ttaatggtga gaccacagag   1860

ctcgtgagga agatgatagt tgtaggtctg tggtgcatac aagtgattcc gactgatcga   1920

ccaacaatga cgagagtcgt cgagatgttg gaagggagca cgagtaatct agagttgcca   1980

cccagagttc tcttgagctg a                                             2001
```

<210> SEQ ID NO 14
<211> LENGTH: 666
<212> TYPE: PRT
<213> ORGANISM: Zea mays

<400> SEQUENCE: 14

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
```

```
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Leu Cys Ser Gly Gly Lys Ala Gly Asn Pro Phe Cys Lys
    290                 295                 300

Pro Ser Arg Ser Lys Arg Lys Glu Ala Ser Ile Val Gly Ala Val Ala
305                 310                 315                 320

Val Ala Phe Leu Cys Leu Val Ile Leu Thr Cys Phe Leu Ala Cys Arg
                325                 330                 335

His Gly Ser Leu Pro Phe Lys Ser Glu Asn Lys Pro Gly Thr Arg Ile
            340                 345                 350

Glu Ser Phe Leu Gln Lys Asn Glu Ser Ile His Pro Lys Arg Tyr Thr
        355                 360                 365

Tyr Thr Asp Val Lys Arg Met Thr Lys Ser Phe Ala Val Lys Leu Gly
    370                 375                 380

Gln Gly Gly Phe Gly Ala Val Tyr Lys Gly Ser Leu His Asp Gly Arg
385                 390                 395                 400

Gln Val Ala Val Lys Met Leu Lys Asp Thr Gln Gly Asp Gly Glu Glu
                405                 410                 415

Phe Met Asn Glu Val Ala Ser Ile Ser Arg Thr Ser His Val Asn Val
            420                 425                 430

Val Thr Leu Leu Gly Phe Cys Leu Gln Gly Ser Lys Arg Ala Leu Ile
        435                 440                 445

Tyr Glu Tyr Met Pro Asn Gly Ser Leu Glu Arg Tyr Ala Phe Thr Gly
    450                 455                 460

Asp Met Asn Ser Glu Asn Leu Leu Thr Trp Glu Arg Leu Phe Asp Ile
465                 470                 475                 480

Ala Ile Gly Thr Ala Arg Gly Leu Glu Tyr Leu His Arg Gly Cys Asn
                485                 490                 495

Thr Arg Ile Val His Phe Asp Ile Lys Pro His Asn Ile Leu Leu Asp
            500                 505                 510

Gln Asp Phe Cys Pro Lys Ile Ser Asp Phe Gly Leu Ala Lys Leu Cys
        515                 520                 525

Leu Asn Lys Glu Ser Ala Ile Ser Ile Val Gly Ala Arg Gly Thr Ile
    530                 535                 540

Gly Tyr Ile Ala Pro Glu Val Tyr Ser Lys Gln Phe Gly Thr Ile Ser
545                 550                 555                 560

Ser Lys Ser Asp Val Tyr Ser Tyr Gly Met Met Val Leu Glu Met Val
                565                 570                 575

Gly Ala Arg Glu Arg Asn Thr Ser Ala Ser Ala Asp Ser Asp His Ser
            580                 585                 590

Ser Gln Tyr Phe Pro Gln Trp Ile Tyr Glu His Leu Asp Asp Tyr Cys
        595                 600                 605

Val Gly Ala Ser Glu Ile Asn Gly Glu Thr Thr Glu Leu Val Arg Lys
    610                 615                 620
```

```
Met Ile Val Val Gly Leu Trp Cys Ile Gln Val Ile Pro Thr Asp Arg
625                 630                 635                 640

Pro Thr Met Thr Arg Val Val Glu Met Leu Glu Gly Ser Thr Ser Asn
                645                 650                 655

Leu Glu Leu Pro Pro Arg Val Leu Leu Ser
            660                 665


<210> SEQ ID NO 15
<211> LENGTH: 2004
<212> TYPE: DNA
<213> ORGANISM: Artificial Sequence
<220> FEATURE:
<223> OTHER INFORMATION: mutant Ht2 cDNA (position 1625: G->A)

<400> SEQUENCE: 15

atggctgctc acctaccacg cctccccgtc ctcctcctcg tcctcctcgc tgcccatgtc     60

gtctccacct ccgcccatgc cgagcctcct cttccgagcc cttacagcac ctccgcccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga attccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020

tcgctgccct tcaaatcgaa gaacaaacca gggacaagga ttgagtcctt cctacagaag   1080

aacgagagta gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaagacta   1440

tttgacatag cgattggcac ggccagaggg ctcgaatacc tacaccgggg atgcaacact   1500

cggatcgtgc attttgacat caagccacac aacatcctgt tagaccagga tttctgccct   1560

aagatctctg actttggact ggccaagcta tgtctgaaca aagagagcgc tatctccatt   1620

gctgacgcaa gagggacgat agggtatatc gccccggagg tctactcaaa gcaatttgga   1680

acgatcagca gcaagtctga tgtctatagc tatgggatga tggtccttga gatggttgga   1740

gcaagggaca ggaatacaag cgcagatagt gaccatagca gccaatattt ccctcagtgg   1800
```

```
ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggaa gcacaagtaa tctagagttg   1980

ccacccagag ttctcttgag ctga                                          2004


<210> SEQ ID NO 16
<211> LENGTH: 667
<212> TYPE: PRT
<213> ORGANISM: Artificial Sequence
<220> FEATURE:
<223> OTHER INFORMATION: mutant Ht2 protein (position 542: G->D)

<400> SEQUENCE: 16

Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320
```

```
Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Asp Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```

<210> SEQ ID NO 17
<211> LENGTH: 2004
<212> TYPE: DNA
<213> ORGANISM: Artificial Sequence
<220> FEATURE:
<223> OTHER INFORMATION: mutant Ht2 cDNA (position 95: C->T)

<400> SEQUENCE: 17

```
atggctgctc acctaccacg cctccccgtc ctcctcctcg tcctcctcgc tgcccatgtc      60

gtctccacct ccgcccatgc cgagcctcct cttctgagcc cttacagcac ctccgcccat     120
```

```
ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga attccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020

tcgctgccct tcaaatcgaa gaacaaacca gggacaagga ttgagtcctt cctacagaag   1080

aacgagagta gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaagacta   1440

tttgacatag cgattggcac ggccagaggg ctcgaatacc tacaccgggg atgcaacact   1500

cggatcgtgc attttgacat caagccacac aacatcctgt tagaccagga tttctgccct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

acgatcagca gcaagtctga tgtctatagc tatgggatga tggtccttga gatggttgga   1740

gcaagggaca ggaatacaag cgcagatagt gaccatagca gccaatattt ccctcagtgg   1800

ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggaa gcacaagtaa tctagagttg   1980

ccacccagag ttctcttgag ctga                                          2004
```

<210> SEQ ID NO 18
<211> LENGTH: 667
<212> TYPE: PRT
<213> ORGANISM: Artificial Sequence
<220> FEATURE:
<223> OTHER INFORMATION: mutant Ht2 protein (position 32: P->L)

<400> SEQUENCE: 18

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Leu
```

```
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445
```

```
Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```

```
<210> SEQ ID NO 19
<211> LENGTH: 2004
<212> TYPE: DNA
<213> ORGANISM: Artificial Sequence
<220> FEATURE:
<223> OTHER INFORMATION: mutant Ht2 cDNA (position 115: G->A)

<400> SEQUENCE: 19

atggctgctc acctaccacg cctccccgtc ctcctcctcg tcctcctcgc tgcccatgtc     60

gtctccacct ccgcccatgc cgagcctcct cttccgagcc cttacagcac ctccacccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780
```

```
aaacggacat cggaggatca gtgtggccag tgcgaggaat cgggctccgg cggacggtgc    840
gcctacagcc agaagagaga attccttggc tgcttctgca gcggagggaa ggcgggcaac    900
ccgttctgca aaccatcaag atcaacaaaa aggagagaag cagcatctat tgttggtgct    960
gttgccgttg cattcctgtg tctagtcatt ctcacatgct tcttggcttg tagacattgt   1020
tcgctgccct tcaaatcgaa gaacaaacca gggacaagga ttgagtcctt cctacagaag   1080
aacgagagta gtatacatcc gaaaagatac acctacgcgg acgtgaaaag aatgacaaaa   1140
tccttcgctg tgaagctagg ccaaggtggg tttggtgctg tatacaaagg cagcctccac   1200
gatggccgac aggtagcagt caagatgctg aaggacaccc aaggtgacgg cgaggaattc   1260
atgaacgagg tggctagcat cagcaggact tctcatgtca acgtcgtgac acttctaggg   1320
ttttgcttgc aagggtcgaa aagagcactg atctacgagt acatgcccaa tggttcgctc   1380
gaaaggtatg ccttcaccgg tgacatgaac agtgagaatt tgctaacctg ggaaagacta   1440
tttgacatag cgattggcac ggccagaggg ctcgaatacc tacaccgggg atgcaacact   1500
cggatcgtgc attttgacat caagccacac aacatcctgt tagaccagga tttctgccct   1560
aagatctctg actttggact ggccaagcta tgtctgaaca aagagagcgc tatctccatt   1620
gctggcgcaa gagggacgat agggtatatc gccccggagg tctactcaaa gcaatttgga   1680
acgatcagca gcaagtctga tgtctatagc tatgggatga tggtccttga gatggttgga   1740
gcaagggaca ggaatacaag cgcagatagt gaccatagca gccaatattt ccctcagtgg   1800
ctttatgaac atttggacga ctattgtgtt ggtgcttccg agattaatgg tgagaccaca   1860
gagctcgtga ggaagatgat agttgtaggt ctgtggtgca tacaagtgat tccgactgat   1920
cgaccaacaa tgacgagagt cgtcgagatg ttggaaggaa gcacaagtaa tctagagttg   1980
ccacccagag ttctcttgag ctga                                          2004
```

<210> SEQ ID NO 20
<211> LENGTH: 667
<212> TYPE: PRT
<213> ORGANISM: Artificial Sequence
<220> FEATURE:
<223> OTHER INFORMATION: mutant Ht2 protein (position 39: A->T)

<400> SEQUENCE: 20

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Thr His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140
```

```
His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
```

```
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```

<210> SEQ ID NO 21
<211> LENGTH: 2003
<212> TYPE: DNA
<213> ORGANISM: Artificial Sequence
<220> FEATURE:
<223> OTHER INFORMATION: cDNA of RLK1 allele from A188
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t

<400> SEQUENCE: 21

```
atggctgctc acctaccacg cctccccgtc ctcctcctcg tcctcctcgc tgcccatgtc      60

gtctccacct ccgcccatgc cgagcctcct cttccgagcc cttacagcac ctccgcccat     120

ggcgagcctc ctcttccgag cacttacaac gtctccatgt gctcggaatc gttctggtgc     180

ggcggcgtcn aaatccgcta cccgttctat cttgccaacg caaccgccga ctacagcggg     240

agctactact cctgcggcta cnccgacttg agcgtttcct gcaaactcga ggtcgagggg     300

ccgacgacga catggacccc taccatccgt ctcggcggcg acaactacac cgtcaagaac     360

atcttgtacg actatcatac catctcactg gcggacagcg atgtgctcgg aggcggcgag     420

tgccccgtcg tccaccacaa cgtcagcttc gacgagacgt ggctgcacaa ccccagcgcc     480

ttcgacaacc tcaccttctt cttcggatgc cactgggggc cacgcgatac actgcctgaa     540

tttgccggca acaacatcag ctgcgccggg ttcagtactc cagctatcag cggtggaggc     600

tccttcgtgt tcaagcctga agatcttgac gaacatgcgg agcaggagtt ggcttcacac     660

tgcgacgagg ttttctccgt gccagtgaga agcgaggctc tgcagcaggc gatcgtcagc     720

aacctcagcc tcggggacgg gtacggcgag ctgcttaggc aggggatcga gttggaatgg     780

aaacggacat cggaggatca gtgtggccag tgcgaggaat cgggctccgg cggacggtgc     840

gcctacagcc agaagagaga attccttggc tgcttgtgca gcggagggaa ggcgggcaac     900

ccgttctgca aaccatcaag atcaacaaaa aggagagaag cagcatctat tgttggtgct     960

gttgccgttg cattcctgtg tctagtcatt ctcacatgct tcttggcttg tagacatggt    1020

tcgctgccct tcaaatcgga gaacaaacca gggacaagga ttgagtcctt cctacagaag    1080

aacgagagta tacatccgaa aagatacacc tacgcggacg tgaaaagaat gacaaaatcc    1140

ttcgctgtga agctaggcca aggtgggttt ggtgctgtat acaaaggcag cctccacgat    1200

ggccgacagg tagcagtcaa gatgctcaag gacacccaag gtgacggcga ggaattcatg    1260
```

```
aacgaggtgg ctagcatcag caggacttct catgtcaacg tcgtgacact tctagggttt   1320

tgcttgcaag ggtcgaaaag agcactgatc tacgagtaca tgcccaatgg ttcgctcgaa   1380

aggtatgcct tcaccggtga catgaacagt gagaatttgc taacctggga aagactattt   1440

gacatagcaa ttggcacacg gccagagggc tcgaatacct acaccgggga tgcaacactc   1500

ggatcgtgca ttttgacatc aagccacaca acatcctgtt agaccaggat ttctgcccta   1560

agatctctga ctttggactg gccaagctat gtctgaacaa agagagcgct atctccattg   1620

ctggcgcaag agggacgata gggtatatcg ccccggaggt ctactcaaag caatttggaa   1680

caataagcag caagtctgat gtctatagct atgggatgat ggtccttgag atggttggag   1740

caagggacag gaatacaagc gcagatagtg accatagcag ccaatatttc cctcagtggc   1800

tttatgagca tttggacgac tattgtgttg gtgcttccga gattaatggt gagaccacag   1860

agctcgtgag gaagatgata gttgtaggtc tgtggtgcat acaagtgatt ccgactgatc   1920

gaccaacaat gacgagagtc gtcgagatgt tggaaggaag cacaagtaat ctagagttgc   1980

cacccagagt tctcttgagc tga                                           2003
```

```
<210> SEQ ID NO 22
<211> LENGTH: 513
<212> TYPE: PRT
<213> ORGANISM: Zea mays
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid

<400> SEQUENCE: 22

Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Xaa
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Xaa Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190
```

```
Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Leu Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Gly Ser Leu Pro Phe Lys Ser Glu Asn Lys Pro Gly Thr
            340                 345                 350

Arg Ile Glu Ser Phe Leu Gln Lys Asn Glu Ser Ile His Pro Lys Arg
        355                 360                 365

Tyr Thr Tyr Ala Asp Val Lys Arg Met Thr Lys Ser Phe Ala Val Lys
    370                 375                 380

Leu Gly Gln Gly Gly Phe Gly Ala Val Tyr Lys Gly Ser Leu His Asp
385                 390                 395                 400

Gly Arg Gln Val Ala Val Lys Met Leu Lys Asp Thr Gln Gly Asp Gly
                405                 410                 415

Glu Glu Phe Met Asn Glu Val Ala Ser Ile Ser Arg Thr Ser His Val
            420                 425                 430

Asn Val Val Thr Leu Leu Gly Phe Cys Leu Gln Gly Ser Lys Arg Ala
        435                 440                 445

Leu Ile Tyr Glu Tyr Met Pro Asn Gly Ser Leu Glu Arg Tyr Ala Phe
    450                 455                 460

Thr Gly Asp Met Asn Ser Glu Asn Leu Leu Thr Trp Glu Arg Leu Phe
465                 470                 475                 480

Asp Ile Ala Ile Gly Thr Arg Pro Glu Gly Ser Asn Thr Tyr Thr Gly
                485                 490                 495

Asp Ala Thr Leu Gly Ser Cys Ile Leu Thr Ser Ser His Thr Thr Ser
            500                 505                 510

Cys
```

<210> SEQ ID NO 23
<211> LENGTH: 2001
<212> TYPE: DNA
<213> ORGANISM: Artificial Sequence
<220> FEATURE:
<223> OTHER INFORMATION: cDNA of modified RLK1 allele from A188
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t

<400> SEQUENCE: 23
atggctgctc acctaccacg cctccccgtc ctcctcctcg tcctcctcgc tgcccatgtc 60
gtctccacct ccgcccatgc cgagcctcct cttccgagcc cttacagcac ctccgcccat 120
ggcgagcctc ctcttccgag cacttacaac gtctccatgt gctcggaatc gttctggtgc 180
ggcggcgtcn aaatccgcta cccgttctat cttgccaacg caaccgccga ctacagcggg 240
agctactact cctgcggcta cnccgacttg agcgtttcct gcaaactcga ggtcgagggg 300
ccgacgacga catggacccc taccatccgt ctcggcggcg acaactacac cgtcaagaac 360
atcttgtacg actatcatac catctcactg gcggacagcg atgtgctcgg aggcggcgag 420
tgccccgtcg tccaccacaa cgtcagcttc gacgagacgt ggctgcacaa ccccagcgcc 480
ttcgacaacc tcaccttctt cttcggatgc cactgggggc cacgcgatac actgcctgaa 540
tttgccggca acaacatcag ctgcgccggg ttcagtactc cagctatcag cggtggaggc 600
tccttcgtgt tcaagcctga agatcttgac gaacatgcgg agcaggagtt ggcttcacac 660
tgcgacgagg ttttctccgt gccagtgaga agcgaggctc tgcagcaggc gatcgtcagc 720
aacctcagcc tcggggacgg gtacggcgag ctgcttaggc aggggatcga gttggaatgg 780
aaacggacat cggaggatca gtgtggccag tgcgaggaat cgggctccgg cggacggtgc 840
gcctacagcc agaagagaga attccttggc tgcttgtgca gcggagggaa ggcgggcaac 900
ccgttctgca aaccatcaag atcaacaaaa aggagagaag cagcatctat tgttggtgct 960
gttgccgttg cattcctgtg tctagtcatt ctcacatgct tcttggcttg tagacatggt 1020
tcgctgccct tcaaatcgga gaacaaacca gggacaagga ttgagtcctt cctacagaag 1080
aacgagagta tacatccgaa aagatacacc tacgcggacg tgaaaagaat gacaaaatcc 1140
ttcgctgtga agctaggcca aggtgggttt ggtgctgtat acaaaggcag cctccacgat 1200
ggccgacagg tagcagtcaa gatgctcaag gacacccaag gtgacggcga ggaattcatg 1260
aacgaggtgg ctagcatcag caggacttct catgtcaacg tcgtgacact tctagggttt 1320
tgcttgcaag ggtcgaaaag agcactgatc tacgagtaca tgcccaatgg ttcgctcgaa 1380
aggtatgcct tcaccggtga catgaacagt gagaatttgc taacctggga aagactattt 1440
gacatagcaa ttggcacggc cagagggctc gaatacctac accggggatg caacactcgg 1500
atcgtgcatt ttgacatcaa gccacacaac atcctgttag accaggattt ctgccctaag 1560
atctctgact ttggactggc caagctatgt ctgaacaaag agagcgctat ctccattgct 1620
ggcgcaagag ggacgatagg gtatatcgcc ccggaggtct actcaaagca atttggaaca 1680
ataagcagca agtctgatgt ctatagctat gggatgatgg tccttgagat ggttggagca 1740
agggacagga atacaagcgc agatagtgac catagcagcc aatatttccc tcagtggctt 1800
tatgagcatt tggacgacta ttgtgttggt gcttccgaga ttaatggtga gaccacagag 1860
ctcgtgagga agatgatagt tgtaggtctg tggtgcatac aagtgattcc gactgatcga 1920
ccaacaatga cgagagtcgt cgagatgttg gaaggaagca caagtaatct agagttgcca 1980
cccagagttc tcttgagctg a 2001

<210> SEQ ID NO 24
<211> LENGTH: 666
<212> TYPE: PRT
<213> ORGANISM: Artificial Sequence
<220> FEATURE:
<223> OTHER INFORMATION: modified RLK1 protein from A188
<220> FEATURE:
<221> NAME/KEY: misc_feature
<222> LOCATION: (64)..(64)

```
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid

<400> SEQUENCE: 24

Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Xaa
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Xaa Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Leu Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Gly Ser Leu Pro Phe Lys Ser Glu Asn Lys Pro Gly Thr
            340                 345                 350

Arg Ile Glu Ser Phe Leu Gln Lys Asn Glu Ser Ile His Pro Lys Arg
        355                 360                 365

Tyr Thr Tyr Ala Asp Val Lys Arg Met Thr Lys Ser Phe Ala Val Lys
    370                 375                 380
```

```
Leu Gly Gln Gly Gly Phe Gly Ala Val Tyr Lys Gly Ser Leu His Asp
385                 390                 395                 400

Gly Arg Gln Val Ala Val Lys Met Leu Lys Asp Thr Gln Gly Asp Gly
                405                 410                 415

Glu Glu Phe Met Asn Glu Val Ala Ser Ile Ser Arg Thr Ser His Val
            420                 425                 430

Asn Val Val Thr Leu Leu Gly Phe Cys Leu Gln Gly Ser Lys Arg Ala
        435                 440                 445

Leu Ile Tyr Glu Tyr Met Pro Asn Gly Ser Leu Glu Arg Tyr Ala Phe
    450                 455                 460

Thr Gly Asp Met Asn Ser Glu Asn Leu Leu Thr Trp Glu Arg Leu Phe
465                 470                 475                 480

Asp Ile Ala Ile Gly Thr Ala Arg Gly Leu Glu Tyr Leu His Arg Gly
                485                 490                 495

Cys Asn Thr Arg Ile Val His Phe Asp Ile Lys Pro His Asn Ile Leu
            500                 505                 510

Leu Asp Gln Asp Phe Cys Pro Lys Ile Ser Asp Phe Gly Leu Ala Lys
        515                 520                 525

Leu Cys Leu Asn Lys Glu Ser Ala Ile Ser Ile Ala Gly Ala Arg Gly
    530                 535                 540

Thr Ile Gly Tyr Ile Ala Pro Glu Val Tyr Ser Lys Gln Phe Gly Thr
545                 550                 555                 560

Ile Ser Ser Lys Ser Asp Val Tyr Ser Tyr Gly Met Met Val Leu Glu
                565                 570                 575

Met Val Gly Ala Arg Asp Arg Asn Thr Ser Ala Asp Ser Asp His Ser
            580                 585                 590

Ser Gln Tyr Phe Pro Gln Trp Leu Tyr Glu His Leu Asp Asp Tyr Cys
        595                 600                 605

Val Gly Ala Ser Glu Ile Asn Gly Glu Thr Thr Glu Leu Val Arg Lys
    610                 615                 620

Met Ile Val Val Gly Leu Trp Cys Ile Gln Val Ile Pro Thr Asp Arg
625                 630                 635                 640

Pro Thr Met Thr Arg Val Val Glu Met Leu Glu Gly Ser Thr Ser Asn
                645                 650                 655

Leu Glu Leu Pro Pro Arg Val Leu Leu Ser
            660                 665
```

<210> SEQ ID NO 25
<211> LENGTH: 47
<212> TYPE: DNA
<213> ORGANISM: Artificial Sequence
<220> FEATURE:
<223> OTHER INFORMATION: SYN14136 Primer Allele X

<400> SEQUENCE: 25
gaaggtgacc aagttcatgc tcatcttgtt cggccttttc tacacta 47

<210> SEQ ID NO 26
<211> LENGTH: 46
<212> TYPE: DNA
<213> ORGANISM: Artificial Sequence
<220> FEATURE:
<223> OTHER INFORMATION: SYN14136 Primer Allele Y

<400> SEQUENCE: 26
gaaggtcgga gtcaacggat tatcttgttc ggccttttct acactc 46

<210> SEQ ID NO 27
<211> LENGTH: 28
<212> TYPE: DNA
<213> ORGANISM: Artificial Sequence
<220> FEATURE:
<223> OTHER INFORMATION: SYN14136 Common Primer

<400> SEQUENCE: 27
agaaccaaaa attcaccagc tgtgagaa 28

<210> SEQ ID NO 28
<211> LENGTH: 36
<212> TYPE: DNA
<213> ORGANISM: Artificial Sequence
<220> FEATURE:
<223> OTHER INFORMATION: PZE-108077560 Primer Allele X

<400> SEQUENCE: 28
gaaggtgacc aagttcatgc tgcagtggcc tgcgca 36

<210> SEQ ID NO 29
<211> LENGTH: 39
<212> TYPE: DNA
<213> ORGANISM: PZE-108077560 Primer Allele Y

<400> SEQUENCE: 29
gaaggtcgga gtcaacggat tgctgcagtg gcctgcgcg 39

<210> SEQ ID NO 30
<211> LENGTH: 28
<212> TYPE: DNA
<213> ORGANISM: Artificial Sequence
<220> FEATURE:
<223> OTHER INFORMATION: PZE-108077560 Common Primer

<400> SEQUENCE: 30
agataatgag tcatcaggct atcagcaa 28

<210> SEQ ID NO 31
<211> LENGTH: 49
<212> TYPE: DNA
<213> ORGANISM: Artificial Sequence
<220> FEATURE:
<223> OTHER INFORMATION: PZE-108093423 Primer Allele X

<400> SEQUENCE: 31
gaaggtgacc aagttcatgc tgtaatccat tgtgaacata tcgctatca 49

<210> SEQ ID NO 32
<211> LENGTH: 47
<212> TYPE: DNA
<213> ORGANISM: Artificial Sequence
<220> FEATURE:
<223> OTHER INFORMATION: PZE-108093423 Primer Allele Y

<400> SEQUENCE: 32
gaaggtcgga gtcaacggat taatccattg tgaacatatc gctatcg 47

<210> SEQ ID NO 33
<211> LENGTH: 25
<212> TYPE: DNA
<213> ORGANISM: Artificial Sequence
<220> FEATURE:
<223> OTHER INFORMATION: PZE-108093423 Common Primer

<400> SEQUENCE: 33
gaaacggttc tgctgcagtt tggta 25

<210> SEQ ID NO 34
<211> LENGTH: 42
<212> TYPE: DNA
<213> ORGANISM: Artificial Sequence
<220> FEATURE:
<223> OTHER INFORMATION: MA0021 Primer Allele X

<400> SEQUENCE: 34
gaaggtgacc aagttcatgc tgagctcatc tcgtccaagc cc 42

<210> SEQ ID NO 35
<211> LENGTH: 42
<212> TYPE: DNA
<213> ORGANISM: Artificial Sequence
<220> FEATURE:
<223> OTHER INFORMATION: MA0021 Primer Allele Y

<400> SEQUENCE: 35
gaaggtcgga gtcaacggat tgagctcatc tcgtccaagc cg 42

<210> SEQ ID NO 36
<211> LENGTH: 19
<212> TYPE: DNA
<213> ORGANISM: Artificial Sequence
<220> FEATURE:
<223> OTHER INFORMATION: MA0021 Common Primer

<400> SEQUENCE: 36
cgctgcggtg ccgggtgat 19

<210> SEQ ID NO 37
<211> LENGTH: 47
<212> TYPE: DNA
<213> ORGANISM: Artificial Sequence
<220> FEATURE:
<223> OTHER INFORMATION: MA0022 Primer Allele X

<400> SEQUENCE: 37
gaaggtgacc aagttcatgc tcaccaacac aatagtcgtc caaatgt 47

<210> SEQ ID NO 38
<211> LENGTH: 46
<212> TYPE: DNA
<213> ORGANISM: Artificial Sequence
<220> FEATURE:
<223> OTHER INFORMATION: MA0022 Primer Allele Y

<400> SEQUENCE: 38
gaaggtcgga gtcaacggat taccaacaca atagtcgtcc aaatgc 46

<210> SEQ ID NO 39
<211> LENGTH: 25
<212> TYPE: DNA
<213> ORGANISM: Artificial Sequence
<220> FEATURE:
<223> OTHER INFORMATION: MA0022 Common Primer

<400> SEQUENCE: 39
cagccaatat ttccctcagt ggctt 25

<210> SEQ ID NO 40
<211> LENGTH: 47
<212> TYPE: DNA

<213> ORGANISM: Artificial Sequence
<220> FEATURE:
<223> OTHER INFORMATION: SYN4196 Primer Allele X

<400> SEQUENCE: 40
gaaggtgacc aagttcatgc tctgcactct ggaatatcta taacaga 47

<210> SEQ ID NO 41
<211> LENGTH: 47
<212> TYPE: DNA
<213> ORGANISM: Artificial Sequence
<220> FEATURE:
<223> OTHER INFORMATION: SYN4196 Primer Allele Y

<400> SEQUENCE: 41
gaaggtcgga gtcaacggat tctgcactct ggaatatcta taacagc 47

<210> SEQ ID NO 42
<211> LENGTH: 25
<212> TYPE: DNA
<213> ORGANISM: Artificial Sequence
<220> FEATURE:
<223> OTHER INFORMATION: SYN4196 Common Primer

<400> SEQUENCE: 42
tggtttatac caggaaggga cgcat 25

<210> SEQ ID NO 43
<211> LENGTH: 1395
<212> TYPE: DNA
<213> ORGANISM: Oryza sativa

<400> SEQUENCE: 43
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttaaaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccaacc caccccagtc cagccaactg gacaatagtc 600
tccacacccc cccactatca ccgtgagttg tccgcacgca ccgcacgtct cgcagccaaa 660
aaaaaaaaaa gaaagaaaaa aaagaaaaag aaaaaacagc aggtgggtcc gggtcgtggg 720
ggccggaaac gcgaggagga tcgcgagcca gcgacgaggc cggccctccc tccgcttcca 780
aagaaacgcc ccccatcgcc actatataca taccccccc tctcctccca tccccccaac 840
cctaccacca ccaccaccac cacctccacc tcctcccccc tcgctgccgg acgacgagct 900 catccccccct ccccctccgc cgccgccgcg ccggtaacca ccccgcccct atcctctttc 960
tttctccgtt ttttttttcc gtctcggtct cgatctttgg ccttggtagt ttgggtgggc 1020
gagaggcggc ttcgtgcgcg cccagatcgg tgcgcgggag gggcgggatc tcgcggctgg 1080
ggctctcgcc ggcgtggatc cggcccggat ctcgcgggga atggggctct cggatgtaga 1140
tctgcgatcc gccgttgttg ggggagatga tggggggttt aaaatttccg ccatgctaaa 1200
caagatcagg aagaggggaa aagggcacta tggtttatat ttttatatat ttctgctgct 1260
tcgtcaggct tagatgtgct agatctttct ttcttctttt tgtgggtaga atttgaatcc 1320
ctcagcattg ttcatcggta gtttttcttt tcatgatttg tgacaaatgc agcctcgtgc 1380
ggagcttttt tgtag 1395

<210> SEQ ID NO 44
<211> LENGTH: 1883
<212> TYPE: DNA
<213> ORGANISM: Brachypodium distachyon

<400> SEQUENCE: 44
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttttag catagtcaaa gtcagattgc ggcactcgct 360
catccacgga aagaattttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860

```
ctgttacttc gatgctgcag ttt                                          1883


<210> SEQ ID NO 45
<211> LENGTH: 2004
<212> TYPE: DNA
<213> ORGANISM: Artificial Sequence
<220> FEATURE:
<223> OTHER INFORMATION: mutant Ht2 cDNA (position 73: G->A)

<400> SEQUENCE: 45

atggctgctc acctaccacg cctccccgtc ctcctcctcg tcctcctcgc tgcccatgtc     60

gtctccacct ccacccatgc cgagcctcct cttccgagcc cttacagcac ctccgcccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga attccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020

tcgctgccct tcaaatcgaa gaacaaacca gggacaagga ttgagtcctt cctacagaag   1080

aacgagagta gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaagacta   1440

tttgacatag cgattggcac ggccagaggg ctcgaatacc tacaccgggg atgcaacact   1500

cggatcgtgc attttgacat caagccacac aacatcctgt tagaccagga tttctgccct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

acgatcagca gcaagtctga tgtctatagc tatgggatga tggtccttga gatggttgga   1740

gcaagggaca ggaatacaag cgcagatagt gaccatagca gccaatattt ccctcagtgg   1800

ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggaa gcacaagtaa tctagagttg   1980

ccacccagag ttctcttgag ctga                                         2004
```

<210> SEQ ID NO 46
<211> LENGTH: 667
<212> TYPE: PRT
<213> ORGANISM: Artificial Sequence
<220> FEATURE:
<223> OTHER INFORMATION: mutant Ht2 protein (position 25: A->T)

<400> SEQUENCE: 46

Met Ala Ala His Leu Pro Arg Leu Pro Val Leu Leu Leu Val Leu Leu
1 5 10 15

Ala Ala His Val Val Ser Thr Ser Thr His Ala Glu Pro Pro Leu Pro
20 25 30

Ser Pro Tyr Ser Thr Ser Ala His Gly Glu Pro Pro Leu Pro Ser Thr
35 40 45

Tyr Asn Val Ser Met Cys Ser Glu Ser Phe Trp Cys Gly Gly Val Glu
50 55 60

Ile Arg Tyr Pro Phe Tyr Leu Ala Asn Ala Thr Ala Asp Tyr Ser Gly
65 70 75 80

Ser Tyr Tyr Ser Cys Gly Tyr Thr Asp Leu Ser Val Ser Cys Lys Leu
85 90 95

Glu Val Glu Gly Pro Thr Thr Thr Trp Thr Pro Thr Ile Arg Leu Gly
100 105 110

Gly Asp Asn Tyr Thr Val Lys Asn Ile Leu Tyr Asp Tyr His Thr Ile
115 120 125

Ser Leu Ala Asp Ser Asp Val Leu Gly Gly Gly Glu Cys Pro Val Val
130 135 140

His His Asn Val Ser Phe Asp Glu Thr Trp Leu His Asn Pro Ser Ala
145 150 155 160

Phe Asp Asn Leu Thr Phe Phe Phe Gly Cys His Trp Gly Pro Arg Asp
165 170 175

Thr Leu Pro Glu Phe Ala Gly Asn Asn Ile Ser Cys Ala Gly Phe Ser
180 185 190

Thr Pro Ala Ile Ser Gly Gly Gly Ser Phe Val Phe Lys Pro Glu Asp
195 200 205

Leu Asp Glu His Ala Glu Gln Glu Leu Ala Ser His Cys Asp Glu Val
210 215 220

Phe Ser Val Pro Val Arg Ser Glu Ala Leu Gln Gln Ala Ile Val Ser
225 230 235 240

Asn Leu Ser Leu Gly Asp Gly Tyr Gly Glu Leu Leu Arg Gln Gly Ile
245 250 255

Glu Leu Glu Trp Lys Arg Thr Ser Glu Asp Gln Cys Gly Gln Cys Glu
260 265 270

Glu Ser Gly Ser Gly Gly Arg Cys Ala Tyr Ser Gln Lys Arg Glu Phe
275 280 285

Leu Gly Cys Phe Cys Ser Gly Gly Lys Ala Gly Asn Pro Phe Cys Lys
290 295 300

Pro Ser Arg Ser Thr Lys Arg Arg Glu Ala Ala Ser Ile Val Gly Ala
305 310 315 320

Val Ala Val Ala Phe Leu Cys Leu Val Ile Leu Thr Cys Phe Leu Ala
325 330 335

Cys Arg His Cys Ser Leu Pro Phe Lys Ser Lys Asn Lys Pro Gly Thr
340 345 350

Arg Ile Glu Ser Phe Leu Gln Lys Asn Glu Ser Ser Ile His Pro Lys
355 360 365

```
Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```

<210> SEQ ID NO 47
<211> LENGTH: 2004
<212> TYPE: DNA
<213> ORGANISM: Artificial Sequence
<220> FEATURE:
<223> OTHER INFORMATION: mutant Ht2 cDNA (position 301: C->T)

<400> SEQUENCE: 47

```
atggctgctc acctaccacg cctccccgtc ctcctcctcg tcctcctcgc tgcccatgtc      60

gtctccacct ccgcccatgc cgagcctcct cttccgagcc cttacagcac ctccgcccat     120

ggcgagcctc ctcttccgag cacttacaac gtctccatgt gctcggaatc gttctggtgc     180

ggcggcgtcg aaatccgcta cccgttctat cttgccaacg caaccgccga ctacagcggg     240

agctactact cctgcggcta caccgacttg agcgtttcct gcaaactcga ggtcgagggg     300

tcgacgacga catggacccc taccatccgt ctcggcggcg acaactacac cgtcaagaac     360
```

```
atcttgtacg actatcatac catctcactg gcggacagcg atgtgctcgg aggcggcgag    420
tgccccgtcg tccaccacaa cgtcagcttc gacgagacgt ggctgcacaa ccccagcgcc    480
ttcgacaacc tcaccttctt cttcggatgc cactgggggc cacgcgatac actgcctgaa    540
tttgccggca acaacatcag ctgcgccggg ttcagtactc cagctatcag cggtggaggc    600
tccttcgtgt tcaagcctga agatcttgac gaacatgcgg agcaggagtt ggcttcacac    660
tgcgacgagg ttttctccgt gccagtgaga agcgaggctc tgcagcaggc gatcgtcagc    720
aacctcagcc tcggggacgg gtacggcgag ctgcttaggc aggggatcga gttggaatgg    780
aaacggacat cggaggatca gtgtggccag tgcgaggaat cgggctccgg cggacggtgc    840
gcctacagcc agaagagaga attccttggc tgcttctgca gcggagggaa ggcgggcaac    900
ccgttctgca aaccatcaag atcaacaaaa aggagagaag cagcatctat tgttggtgct    960
gttgccgttg cattcctgtg tctagtcatt ctcacatgct tcttggcttg tagacattgt   1020
tcgctgccct tcaaatcgaa gaacaaacca gggacaagga ttgagtcctt cctacagaag   1080
aacgagagta gtatacatcc gaaaagatac acctacgcgg acgtgaaaag aatgacaaaa   1140
tccttcgctg tgaagctagg ccaaggtggg tttggtgctg tatacaaagg cagcctccac   1200
gatggccgac aggtagcagt caagatgctg aaggacaccc aaggtgacgg cgaggaattc   1260
atgaacgagg tggctagcat cagcaggact tctcatgtca acgtcgtgac acttctaggg   1320
ttttgcttgc aagggtcgaa aagagcactg atctacgagt acatgcccaa tggttcgctc   1380
gaaaggtatg ccttcaccgg tgacatgaac agtgagaatt tgctaacctg ggaaagacta   1440
tttgacatag cgattggcac ggccagaggg ctcgaatacc tacaccgggg atgcaacact   1500
cggatcgtgc attttgacat caagccacac aacatcctgt tagaccagga tttctgccct   1560
aagatctctg actttggact ggccaagcta tgtctgaaca aagagagcgc tatctccatt   1620
gctggcgcaa gagggacgat agggtatatc gccccggagg tctactcaaa gcaatttgga   1680
acgatcagca gcaagtctga tgtctatagc tatgggatga tggtccttga gatggttgga   1740
gcaagggaca ggaatacaag cgcagatagt gaccatagca gccaatattt ccctcagtgg   1800
ctttatgaac atttggacga ctattgtgtt ggtgcttccg agattaatgg tgagaccaca   1860
gagctcgtga ggaagatgat agttgtaggt ctgtggtgca tacaagtgat tccgactgat   1920
cgaccaacaa tgacgagagt cgtcgagatg ttggaaggaa gcacaagtaa tctagagttg   1980
ccacccagag ttctcttgag ctga                                            2004
```

<210> SEQ ID NO 48
<211> LENGTH: 667
<212> TYPE: PRT
<213> ORGANISM: Artificial Sequence
<220> FEATURE:
<223> OTHER INFORMATION: mutant Ht2 protein (position 101: P->S)

<400> SEQUENCE: 48

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60
```

-continued

```
Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Ser Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
```

```
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 49
<211> LENGTH: 2004
<212> TYPE: DNA
<213> ORGANISM: Artificial Sequence
<220> FEATURE:
<223> OTHER INFORMATION: mutant Ht2 cDNA (position 715: G->A)

<400> SEQUENCE: 49

atggctgctc acctaccacg cctccccgtc ctcctcctcg tcctcctcgc tgcccatgtc     60

gtctccacct ccgcccatgc cgagcctcct cttccgagcc cttacagcac ctccgcccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcatcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga attccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020
```

```
tcgctgccct tcaaatcgaa gaacaaacca gggacaagga ttgagtcctt cctacagaag   1080
aacgagagta gtatacatcc gaaaagatac acctacgcgg acgtgaaaag aatgacaaaa   1140
tccttcgctg tgaagctagg ccaaggtggg tttggtgctg tatacaaagg cagcctccac   1200
gatggccgac aggtagcagt caagatgctg aaggacaccc aaggtgacgg cgaggaattc   1260
atgaacgagg tggctagcat cagcaggact tctcatgtca acgtcgtgac acttctaggg   1320
ttttgcttgc aagggtcgaa aagagcactg atctacgagt acatgcccaa tggttcgctc   1380
gaaaggtatg ccttcaccgg tgacatgaac agtgagaatt tgctaacctg ggaaagacta   1440
tttgacatag cgattggcac ggccagaggg ctcgaatacc tacaccgggg atgcaacact   1500
cggatcgtgc attttgacat caagccacac aacatcctgt tagaccagga tttctgccct   1560
aagatctctg actttggact ggccaagcta tgtctgaaca aagagagcgc tatctccatt   1620
gctggcgcaa gagggacgat agggtatatc gccccggagg tctactcaaa gcaatttgga   1680
acgatcagca gcaagtctga tgtctatagc tatgggatga tggtccttga gatggttgga   1740
gcaagggaca ggaatacaag cgcagatagt gaccatagca gccaatattt ccctcagtgg   1800
ctttatgaac atttggacga ctattgtgtt ggtgcttccg agattaatgg tgagaccaca   1860
gagctcgtga ggaagatgat agttgtaggt ctgtggtgca tacaagtgat tccgactgat   1920
cgaccaacaa tgacgagagt cgtcgagatg ttggaaggaa gcacaagtaa tctagagttg   1980
ccacccagag ttctcttgag ctga                                           2004
```

<210> SEQ ID NO 50
<211> LENGTH: 667
<212> TYPE: PRT
<213> ORGANISM: Artificial Sequence
<220> FEATURE:
<223> OTHER INFORMATION: mutant Ht2 protein (position 239: V->I)

<400> SEQUENCE: 50

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190
```

```
Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Ile Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605
```

```
Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 51
<211> LENGTH: 2004
<212> TYPE: DNA
<213> ORGANISM: Artificial Sequence
<220> FEATURE:
<223> OTHER INFORMATION: mutant Ht2 cDNA (position 862: T->A)

<400> SEQUENCE: 51

atggctgctc acctaccacg cctccccgtc ctcctcctcg tcctcctcgc tgcccatgtc     60

gtctccacct ccgcccatgc cgagcctcct cttccgagcc cttacagcac ctccgcccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga aatccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020

tcgctgccct tcaaatcgaa gaacaaacca gggacaagga ttgagtcctt cctacagaag   1080

aacgagagta gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaagacta   1440

tttgacatag cgattggcac ggccagaggg ctcgaatacc tacaccgggg atgcaacact   1500

cggatcgtgc attttgacat caagccacac aacatcctgt tagaccagga tttctgccct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

acgatcagca gcaagtctga tgtctatagc tatgggatga tggtccttga gatggttgga   1740
```

```
gcaagggaca ggaatacaag cgcagatagt gaccatagca gccaatattt ccctcagtgg   1800

ctttatgaac atttggacga ctattgtgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggaa gcacaagtaa tctagagttg   1980

ccacccagag ttctcttgag ctga                                          2004


<210> SEQ ID NO 52
<211> LENGTH: 667
<212> TYPE: PRT
<213> ORGANISM: Artificial Sequence
<220> FEATURE:
<223> OTHER INFORMATION: mutant Ht2 protein (position 288: F->I)

<400> SEQUENCE: 52

Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Ile
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
```

```
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```

<210> SEQ ID NO 53
<211> LENGTH: 2004
<212> TYPE: DNA
<213> ORGANISM: Artificial Sequence
<220> FEATURE:
<223> OTHER INFORMATION: mutant Ht2 cDNA (position 929: A->G)

<400> SEQUENCE: 53
atggctgctc acctaccacg cctccccgtc ctcctcctcg tcctcctcgc tgcccatgtc 60

```
gtctccacct ccgcccatgc cgagcctcct cttccgagcc cttacagcac ctccgcccat    120
ggcgagcctc ctcttccgag cacttacaac gtctccatgt gctcggaatc gttctggtgc    180
ggcggcgtcg aaatccgcta cccgttctat cttgccaacg caaccgccga ctacagcggg    240
agctactact cctgcggcta caccgacttg agcgtttcct gcaaactcga ggtcgagggg    300
ccgacgacga catggacccc taccatccgt ctcggcggcg acaactacac cgtcaagaac    360
atcttgtacg actatcatac catctcactg gcggacagcg atgtgctcgg aggcggcgag    420
tgccccgtcg tccaccacaa cgtcagcttc gacgagacgt ggctgcacaa ccccagcgcc    480
ttcgacaacc tcaccttctt cttcggatgc cactgggggc cacgcgatac actgcctgaa    540
tttgccggca acaacatcag ctgcgccggg ttcagtactc cagctatcag cggtggaggc    600
tccttcgtgt tcaagcctga agatcttgac gaacatgcgg agcaggagtt ggcttcacac    660
tgcgacgagg ttttctccgt gccagtgaga agcgaggctc tgcagcaggc gatcgtcagc    720
aacctcagcc tcggggacgg gtacggcgag ctgcttaggc aggggatcga gttggaatgg    780
aaacggacat cggaggatca gtgtggccag tgcgaggaat cgggctccgg cggacggtgc    840
gcctacagcc agaagagaga attccttggc tgcttctgca gcggagggaa ggcgggcaac    900
ccgttctgca aaccatcaag atcaacaaga aggagagaag cagcatctat tgttggtgct    960
gttgccgttg cattcctgtg tctagtcatt ctcacatgct tcttggcttg tagacattgt   1020
tcgctgccct tcaaatcgaa gaacaaacca gggacaagga ttgagtcctt cctacagaag   1080
aacgagagta gtatacatcc gaaaagatac acctacgcgg acgtgaaaag aatgacaaaa   1140
tccttcgctg tgaagctagg ccaaggtggg tttggtgctg tatacaaagg cagcctccac   1200
gatggccgac aggtagcagt caagatgctg aaggacaccc aaggtgacgg cgaggaattc   1260
atgaacgagg tggctagcat cagcaggact tctcatgtca acgtcgtgac acttctaggg   1320
ttttgcttgc aagggtcgaa aagagcactg atctacgagt acatgcccaa tggttcgctc   1380
gaaaggtatg ccttcaccgg tgacatgaac agtgagaatt tgctaacctg ggaaagacta   1440
tttgacatag cgattggcac ggccagaggg ctcgaatacc tacaccgggg atgcaacact   1500
cggatcgtgc attttgacat caagccacac aacatcctgt tagaccagga tttctgccct   1560
aagatctctg actttggact ggccaagcta tgtctgaaca aagagagcgc tatctccatt   1620
gctggcgcaa gagggacgat agggtatatc gccccggagg tctactcaaa gcaatttgga   1680
acgatcagca gcaagtctga tgtctatagc tatgggatga tggtccttga gatggttgga   1740
gcaagggaca ggaatacaag cgcagatagt gaccatagca gccaatattt ccctcagtgg   1800
ctttatgaac atttggacga ctattgtgtt ggtgcttccg agattaatgg tgagaccaca   1860
gagctcgtga ggaagatgat agttgtaggt ctgtggtgca tacaagtgat tccgactgat   1920
cgaccaacaa tgacgagagt cgtcgagatg ttggaaggaa gcacaagtaa tctagagttg   1980
ccacccagag ttctcttgag ctga                                           2004
```

```
<210> SEQ ID NO 54
<211> LENGTH: 667
<212> TYPE: PRT
<213> ORGANISM: Artificial Sequence
<220> FEATURE:
<223> OTHER INFORMATION: mutant Ht2 protein (position 310: K->R)

<400> SEQUENCE: 54

Met Ala Ala His Leu Pro Arg Leu Pro Val Leu Leu Leu Val Leu Leu
1               5                   10                  15
```

```
Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Arg Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430
```

```
Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 55
<211> LENGTH: 2004
<212> TYPE: DNA
<213> ORGANISM: Artificial Sequence
<220> FEATURE:
<223> OTHER INFORMATION: mutant Ht2 cDNA (position 1289: C->T)

<400> SEQUENCE: 55

atggctgctc acctaccacg cctccccgtc ctcctcctcg tcctcctcgc tgcccatgtc      60

gtctccacct ccgcccatgc cgagcctcct cttccgagcc cttacagcac ctccgcccat     120

ggcgagcctc ctcttccgag cacttacaac gtctccatgt gctcggaatc gttctggtgc     180

ggcggcgtcg aaatccgcta cccgttctat cttgccaacg caaccgccga ctacagcggg     240

agctactact cctgcggcta caccgacttg agcgtttcct gcaaactcga ggtcgagggg     300

ccgacgacga catggacccc taccatccgt ctcggcggcg acaactacac cgtcaagaac     360

atcttgtacg actatcatac catctcactg gcggacagcg atgtgctcgg aggcggcgag     420

tgccccgtcg tccaccacaa cgtcagcttc gacgagacgt ggctgcacaa ccccagcgcc     480

ttcgacaacc tcaccttctt cttcggatgc cactgggggc cacgcgatac actgcctgaa     540

tttgccggca acaacatcag ctgcgccggg ttcagtactc cagctatcag cggtggaggc     600

tccttcgtgt tcaagcctga agatcttgac gaacatgcgg agcaggagtt ggcttcacac     660

tgcgacgagg ttttctccgt gccagtgaga agcgaggctc tgcagcaggc gatcgtcagc     720
```

aacctcagcc tcggggacgg gtacggcgag ctgcttaggc aggggatcga gttggaatgg 780
aaacggacat cggaggatca gtgtggccag tgcgaggaat cgggctccgg cggacggtgc 840
gcctacagcc agaagagaga attccttggc tgcttctgca gcggagggaa ggcgggcaac 900
ccgttctgca aaccatcaag atcaacaaaa aggagagaag cagcatctat tgttggtgct 960
gttgccgttg cattcctgtg tctagtcatt ctcacatgct tcttggcttg tagacattgt 1020
tcgctgccct tcaaatcgaa gaacaaacca gggacaagga ttgagtcctt cctacagaag 1080
aacgagagta gtatacatcc gaaaagatac acctacgcgg acgtgaaaag aatgacaaaa 1140
tccttcgctg tgaagctagg ccaaggtggg tttggtgctg tatacaaagg cagcctccac 1200
gatggccgac aggtagcagt caagatgctg aaggacaccc aaggtgacgg cgaggaattc 1260
atgaacgagg tggctagcat cagcaggatt tctcatgtca acgtcgtgac acttctaggg 1320
ttttgcttgc aagggtcgaa aagagcactg atctacgagt acatgcccaa tggttcgctc 1380
gaaaggtatg ccttcaccgg tgacatgaac agtgagaatt tgctaacctg ggaaagacta 1440
tttgacatag cgattggcac ggccagaggg ctcgaatacc tacaccgggg atgcaacact 1500
cggatcgtgc attttgacat caagccacac aacatcctgt tagaccagga tttctgccct 1560
aagatctctg actttggact ggccaagcta tgtctgaaca aagagagcgc tatctccatt 1620
gctggcgcaa gagggacgat agggtatatc gccccggagg tctactcaaa gcaatttgga 1680
acgatcagca gcaagtctga tgtctatagc tatgggatga tggtccttga gatggttgga 1740
gcaagggaca ggaatacaag cgcagatagt gaccatagca gccaatattt ccctcagtgg 1800
ctttatgaac atttggacga ctattgtgtt ggtgcttccg agattaatgg tgagaccaca 1860
gagctcgtga ggaagatgat agttgtaggt ctgtggtgca tacaagtgat tccgactgat 1920
cgaccaacaa tgacgagagt cgtcgagatg ttggaaggaa gcacaagtaa tctagagttg 1980
ccacccagag ttctcttgag ctga 2004

<210> SEQ ID NO 56
<211> LENGTH: 667
<212> TYPE: PRT
<213> ORGANISM: Artificial Sequence
<220> FEATURE:
<223> OTHER INFORMATION: mutant Ht2 protein (position 430: T->I)

<400> SEQUENCE: 56

Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val

```
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Ile Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560
```

```
Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 57
<211> LENGTH: 2004
<212> TYPE: DNA
<213> ORGANISM: Artificial Sequence
<220> FEATURE:
<223> OTHER INFORMATION: mutant Ht2 cDNA (position 1826: G->A)

<400> SEQUENCE: 57

atggctgctc acctaccacg cctccccgtc ctcctcctcg tcctcctcgc tgcccatgtc     60

gtctccacct ccgcccatgc cgagcctcct cttccgagcc cttacagcac ctccgcccat    120

ggcgagcctc ctcttccgag cacttacaac gtctccatgt gctcggaatc gttctggtgc    180

ggcggcgtcg aaatccgcta cccgttctat cttgccaacg caaccgccga ctacagcggg    240

agctactact cctgcggcta caccgacttg agcgtttcct gcaaactcga ggtcgagggg    300

ccgacgacga catggacccc taccatccgt ctcggcggcg acaactacac cgtcaagaac    360

atcttgtacg actatcatac catctcactg gcggacagcg atgtgctcgg aggcggcgag    420

tgccccgtcg tccaccacaa cgtcagcttc gacgagacgt ggctgcacaa ccccagcgcc    480

ttcgacaacc tcaccttctt cttcggatgc cactgggggc cacgcgatac actgcctgaa    540

tttgccggca acaacatcag ctgcgccggg ttcagtactc cagctatcag cggtggaggc    600

tccttcgtgt tcaagcctga agatcttgac gaacatgcgg agcaggagtt ggcttcacac    660

tgcgacgagg ttttctccgt gccagtgaga agcgaggctc tgcagcaggc gatcgtcagc    720

aacctcagcc tcggggacgg gtacggcgag ctgcttaggc aggggatcga gttggaatgg    780

aaacggacat cggaggatca gtgtggccag tgcgaggaat cgggctccgg cggacggtgc    840

gcctacagcc agaagagaga attccttggc tgcttctgca gcggagggaa ggcgggcaac    900

ccgttctgca aaccatcaag atcaacaaaa aggagagaag cagcatctat tgttggtgct    960

gttgccgttg cattcctgtg tctagtcatt ctcacatgct tcttggcttg tagacattgt   1020

tcgctgccct tcaaatcgaa gaacaaacca gggacaagga ttgagtcctt cctacagaag   1080

aacgagagta gtatacatcc gaaaagatac acctacgcgg acgtgaaaag aatgacaaaa   1140

tccttcgctg tgaagctagg ccaaggtggg tttggtgctg tatacaaagg cagcctccac   1200

gatggccgac aggtagcagt caagatgctg aaggacaccc aaggtgacgg cgaggaattc   1260

atgaacgagg tggctagcat cagcaggact tctcatgtca acgtcgtgac acttctaggg   1320

ttttgcttgc aagggtcgaa aagagcactg atctacgagt acatgcccaa tggttcgctc   1380

gaaaggtatg ccttcaccgg tgacatgaac agtgagaatt tgctaacctg ggaaagacta   1440
```

```
tttgacatag cgattggcac ggccagaggg ctcgaatacc tacaccgggg atgcaacact   1500

cggatcgtgc attttgacat caagccacac aacatcctgt tagaccagga tttctgccct   1560

aagatctctg actttggact ggccaagcta tgtctgaaca aagagagcgc tatctccatt   1620

gctggcgcaa gagggacgat agggtatatc gccccggagg tctactcaaa gcaatttgga   1680

acgatcagca gcaagtctga tgtctatagc tatgggatga tggtccttga gatggttgga   1740

gcaagggaca ggaatacaag cgcagatagt gaccatagca gccaatattt ccctcagtgg   1800

ctttatgaac atttggacga ctattatgtt ggtgcttccg agattaatgg tgagaccaca   1860

gagctcgtga ggaagatgat agttgtaggt ctgtggtgca tacaagtgat tccgactgat   1920

cgaccaacaa tgacgagagt cgtcgagatg ttggaaggaa gcacaagtaa tctagagttg   1980

ccacccagag ttctcttgag ctga                                          2004
```

<210> SEQ ID NO 58
<211> LENGTH: 667
<212> TYPE: PRT
<213> ORGANISM: Artificial Sequence
<220> FEATURE:
<223> OTHER INFORMATION: mutant Ht2 protein (position 609: C->Y)

<400> SEQUENCE: 58

```
Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255
```

-continued

```
Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Phe Cys Ser Gly Gly Lys Ala Gly Asn Pro Phe Cys Lys
    290                 295                 300

Pro Ser Arg Ser Thr Lys Arg Arg Glu Ala Ala Ser Ile Val Gly Ala
305                 310                 315                 320

Val Ala Val Ala Phe Leu Cys Leu Val Ile Leu Thr Cys Phe Leu Ala
                325                 330                 335

Cys Arg His Cys Ser Leu Pro Phe Lys Ser Lys Asn Lys Pro Gly Thr
            340                 345                 350

Arg Ile Glu Ser Phe Leu Gln Lys Asn Glu Ser Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Thr Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Tyr Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665
```